United States Patent [19]

Levitt

[11] Patent Number: 4,523,943

[45] Date of Patent: Jun. 18, 1985

[54] HERBICIDAL N-(HETEROCYCLIC)-AMINOCARBONYL THIOPHENESULFONAMIDES

[75] Inventor: George Levitt, Wilmington, Del.

[73] Assignee: E. I. Du Pont de Nemours and Company, Wilmington, Del.

[21] Appl. No.: 491,528

[22] Filed: May 4, 1983

Related U.S. Application Data

[60] Division of Ser. No. 255,226, May 4, 1981, Pat. No. 4,398,939, which is a continuation-in-part of Ser. No. 153,279, Jun. 3, 1980, abandoned, which is a continuation-in-part of Ser. No. 27,025, Apr. 4, 1979, abandoned.

[51] Int. Cl.³ .................. C07D 409/12; A01N 46/66
[52] U.S. Cl. .................................. 71/90; 544/212
[58] Field of Search ................ 544/212; 71/93, 90

[56] References Cited

U.S. PATENT DOCUMENTS

| 4,127,405 | 11/1978 | Levitt . | |
|---|---|---|---|
| 4,169,719 | 10/1979 | Levitt . | |
| 4,339,266 | 7/1982 | Levitt | 544/212 |
| 4,441,910 | 4/1984 | Shapiro | 544/212 |
| 4,443,244 | 4/1984 | Levitt | 544/212 |

Primary Examiner—John M. Ford

[57] ABSTRACT

Designated thiophenesulfonamides are useful as herbicides and in particular in the control of broadleaf weeds.

26 Claims, No Drawings

HERBICIDAL N-(HETEROCYCLIC)-AMINOCARBONYL THIOPHENESULFONAMIDES

RELATED APPLICATIONS

This application is a divisional application of U.S. Ser. No. 255,226 filed May 4, 1981 (now U.S. Pat. No. 4,398,939) which in turn is a continuation-in-part of my U.S. Ser. No. 153,279 filed June 3, 1980 (now abandoned) which in turn is a continuation-in-part of my application U.S. Ser. No. 027,025 filed Apr. 4, 1979 (now abandoned).

BACKGROUND OF THE INVENTION

This invention relates to thiophenesulfonamides and their use as agricultural chemicals and particularly as herbicides.

U.S. Pat. No. 4,127,405 teaches compounds which are useful for controlling weeds in wheat having the formula

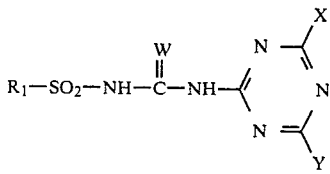

wherein $R_1$ is

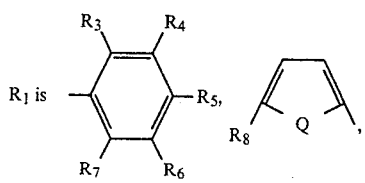

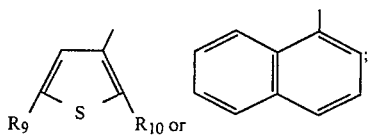

$R_3$ and $R_6$ are independently hydrogen, fluorine, chlorine, bromine, iodine, alkyl of 1–4 carbon atoms, alkoxy of 1–4 carbon atoms, nitro, trifluoromethyl, cyano, $CH_3S(O)_n-$ or $CH_3CH_2S(O)_n-$;

$R_4$ is hydrogen, fluorine, chlorine, bromine or methyl;

$R_5$ is hydrogen, fluorine, chlorine, bromine, methyl or methoxy;

$R_7$ is hydrogen, fluorine, chlorine, bromine, alkyl of 1–2 carbon atoms or alkoxy of 1–2 carbon atoms;

$R_8$ is hydrogen, methyl, chlorine or bromine;

$R_9$ and $R_{10}$ are independently hydrogen, methyl, chlorine or bromine;

W and Q are independently oxygen or sulfur;

n is 0, 1 or 2;

X is hydrogen, chlorine, bromine, methyl, ethyl, alkoxy of 1–3 carbon atoms, trifluoromethyl, $CH_3S-$ or $CH_3OCH_2-$; and Z is methyl or methoxy; or their agriculturally suitable salts; provided that:

(a) when $R_5$ is other than hydrogen, at least one of $R_3$, $R_4$, $R_6$ and $R_7$ is other than hydrogen and at least two of $R_3$, $R_4$, $R_6$ and $R_7$ must be hydrogen;

(b) when $R_5$ is hydrogen and all of $R_3$, $R_4$, $R_6$ and $R_7$ are other than hydrogen, then all of $R_3$, $R_4$, $R_6$ and $R_7$ must be either chlorine or methyl; and (c) when $R_3$ and $R_7$ are both hydrogen, at least one of $R_4$, $R_5$ or $R_6$ must be hydrogen.

French Pat. No. 1,468,747 discloses the following para-substituted phenylsulfonamides, useful as antidiabetic agents:

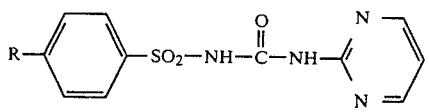

wherein R=H, halogen, $CF_3$ or alkyl.

Logemann et al. Chem. Ab., 53, 18052 g (1959), disclose a number of sulfonamides, including uracil derivatives and those having the formula:

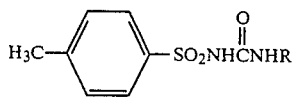

wherein R is butyl, phenyl or

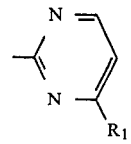

and $R_1$ is hydrogen or methyl. When tested for hypoglycemic effect in rats (oral doses of 25 mg/100 g), the compounds in which R is butyl and phenyl were most potent. The others were of low potency or inactive.

Wojciechowski, J. Acta. Polon. Pharm. 19, p. 121-5 (1962) [Chem Ab., 59 1633 e] describes the synthesis of N-[(2,6-dimethoxypyrimidin-4-yl)aminocarbonyl]-4-methylbenzenesulfonamide:

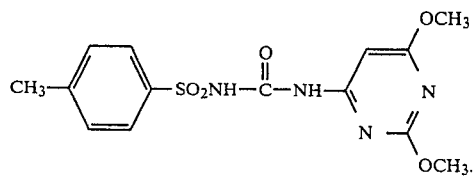

Based upon similarity to a known compound, the author predicted hypoglycemic activity for the foregoing compound.

Netherlands Pat. No. 121,788, published Sept. 15, 1966, teaches the preparation of compounds of Formula (i), and their use as general or selective herbicides,

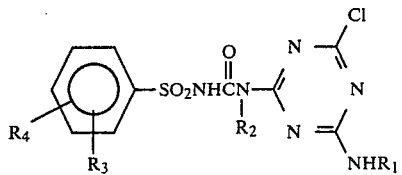

wherein

R₁ and R₂ may independently be alkyl of 1-4 carbon atoms; and

R₃ and R₄ may independently be hydrogen, chlorine or alkyl of 1-4 carbon atoms.

Compounds of Formula (ii), and their use as antidiabetic agents, are reported in *J. Drug. Res.* 6, 123 (1974),

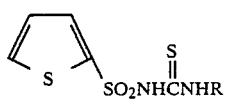

wherein R is pyridyl.

The presence of undesired vegetation causes substantial damage to useful crops, especially agricultural products that satisfy man's basic food needs, such as barley, wheat, and the like. The current population explosion and concomitant world food shortage demand improvements in the efficiency of producing these crops. Prevention or minimizing the loss of a portion of such valuable crops by killing, or inhibiting the growth of undesired vegetation is one way of improving this efficiency.

A wide variety of materials useful for killing, or inhibiting (controlling) the growth of undesired vegetation is available; such materials are commonly referred to as herbicides. The need exists, however, for still more effective herbicides that destroy or retard weeds without causing significant damage to useful crops.

SUMMARY OF THE INVENTION

This invention relates to compounds of Formula I and their agriculturally suitable salts, to agricultural compositions containing them, and to their method of use as general and selective pre- and post-emergence herbicides and as plant growth regulators.

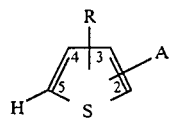

wherein

A is $SO_2N(R_3)C(O)N(R_4)R_5$;

R is $C_1$-$C_4$ alkyl, $C_3$ alkenyl, $OCH_3$, $NO_2$, Cl, Br, $SO_2NR_1R_2$ and $SO_2N(OCH_3)CH_3$;

$R_1$ and $R_2$ are independently $C_1$-$C_3$ alkyl;

$R_3$ is H or $CH_3$;

$R_4$ is H, $CH_3$ or $OCH_3$;

$R_5$ is

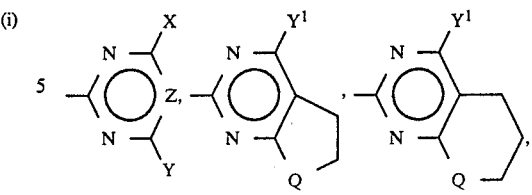

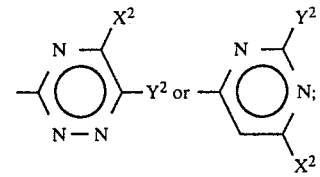

X is H, Cl, Br, $CH_3$, $CH_2CH_3$, $C_1$-$C_3$ alkoxy, $CF_3$, $SCH_3$, $CH_2OCH_3$, $OCH_2CH=CH_2$ or $OCH_2C\equiv CH$;

Y is $CH_3$ or $OCH_3$;

Z is CH, N, CCl, CBr, CCN, $CCH_3$, $CCH_2CH_3$, $CCH_2CH_2Cl$ or $CCH_2CH=CH_2$;

$Y^1$ is H, $CH_3$, $OCH_3$ or Cl;

$X^2$ and $Y^2$ are independently $CH_3$ or $OCH_3$; and

Q is O or $CH_2$; and their agricultural salts;

provided that (a) A cannot be in the 4-position of the thiophene ring; and (b) one of $R_3$ or $R_4$ must be H; and (c) when A is in the 3-position and R is in the 2-position, then R is other than Cl, Br or $CH_3$ where $R_5$ is

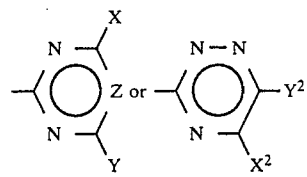

and Z is CH or N.

Preferred for their higher herbicidal activity and/or more favorable ease of synthesis are:

(1) Compounds of the generic scope wherein $R_3$ is H, and $R_4$ is H or $CH_3$;

(2) Compounds of Preferred (1) wherein Z is CH or N and Q is O;

(3) Compounds of Preferred (2) with the formula

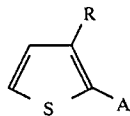

(4) Compounds of Preferred (2) with the formula

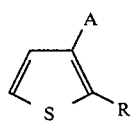

(5) Compounds of Preferred (2) with the formula

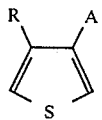

(6) Compounds of Preferred (3) wherein X is H, Cl, CH$_3$, CH$_2$CH$_3$, OCH$_3$ or OCH$_2$CH$_3$; and Y$^1$ is CH$_3$ or OCH$_3$;

(7) Compounds of Preferred (4) wherein X is H, Cl, CH$_3$, CH$_2$CH$_3$, OCH$_3$ or OCH$_2$CH$_3$; and Y$^1$ is CH$_3$ or OCH$_3$;

(8) Compounds of Preferred (5) wherein X is H, Cl, CH$_3$, CH$_2$CH$_3$, OCH$_3$ or OCH$_2$CH$_3$; and Y$^1$ is CH$_3$ or OCH$_3$;

(9) Compounds of Preferred (6) and (7) wherein R is CH$_3$, NO$_2$, Cl, Br or SO$_2$N(CH$_3$)$_2$;

(10) Compounds of Preferred (8) wherein R is CH$_3$, Cl, Br or SO$_2$N(CH$_3$)$_2$;

(11) Compounds of Preferred (9) and (10) wherein R$_5$ is

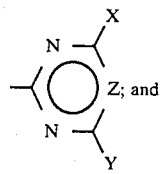

(12) Compounds of Preferred (11) wherein X is CH$_3$ or OCH$_3$, and R$_4$ is H.

Specifically Preferred for highest herbicidal activity and/or most favorable ease of synthesis are:

N-[(4-methoxy-6-methyl-2-pyrimidinyl)aminocarbonyl]-3-chloro-2-thiophenesulfonamide;

N-[(4,6-dimethyl-2-pyrimidinyl)aminocarbonyl]-3-chloro-2-thiophenesulfonamide;

N-[(4,6-dimethoxy-2-pyrimidinyl)aminocarbonyl]-3-chloro-2-thiophenesulfonamide;

N-[(4-methyl-1,3,5-triazin-2-yl)aminocarbonyl]-3-chloro-2-thiophenesulfonamide;

N-[(4,6-dimethyl-1,3,5-triazin-2-yl)aminocarbonyl]-3-chloro-2-thiophenesulfonamide;

N-[(4,6-dimethoxy-1,3,5-triazin-2-yl)aminocarbonyl]-3-chloro-2-thiophenesulfonamide;

N-[(4-methoxy-6-methyl-2-pyrimidinyl)aminocarbonyl]-3-bromo-2-thiophenesulfonamide;

N-(4,6-dimethyl-2-pyrimidinyl)aminocarbonyl]-3-bromo-2-thiophenesulfonamide;

N-(4,6-dimethoxy-2-pyrimidinyl)aminocarbonyl]-3-bromo-2-thiophenesulfonamide;

N-[(4-methoxy-6-methyl-1,3,5-triazin-2-yl)aminocarbonyl]-3-bromo-2-thiophenesulfonamide;

N-[(4,6-dimethyl-1,3,5-triazin-2-yl)aminocarbonyl]-3-bromo-2-thiophenesulfonamide;

N-[(4,6-dimethoxy-1,3,5-triazin-2-yl)aminocarbonyl]-3-bromo-2-thiophenesulfonamide;

N-[(4-methoxy-6-methyl-2-pyrimidinyl)aminocarbonyl]-3-methyl-2-thiophenesulfonamide;

N-[(4,6-dimethyl-2-pyrimidinyl)aminocarbonyl]-3-methyl-2-thiophenesulfonamide;

N-[(4,6-dimethoxy-2-pyrimidinyl)aminocarbonyl]-3-methyl-2-thiophenesulfonamide;

N-[(4-methoxy-6-methyl-1,3,5-triazin-2-yl)aminocarbonyl]-3-methyl-2-thiophenesulfonamide;

N-[(4,6-dimethyl-1,3,5-triazin-2-yl)aminocarbonyl]-3-methyl-2-thiophenesulfonamide; and N-[(4,6-dimethoxy-1,3,5-triazin-2-yl)aminocarbonyl]-3-methyl-2-thiophenesulfonamide.

This invention also relates to compounds of Formula II which are especially useful for the preparation of the compounds of Formula I

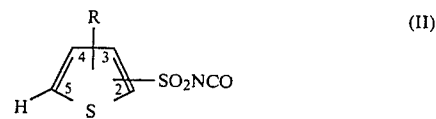

wherein

R is C$_1$–C$_4$ alkyl, C$_3$ alkenyl, OCH$_3$, NO$_2$, Cl, Br, SO$_2$NR$_1$R$_2$ or SO$_2$N(OCH$_3$)CH$_3$;

R$_1$ and R$_2$ are independently C$_1$–C$_3$ alkyl;

provided that (a) the sulfonyl isocyanate group cannot be in the 4-position of the thiophene ring; and (b) when the sulfonyl isocyanate is in the 3-position and R is in the 2-position then R is other than Cl, Br or CH$_3$.

This invention also relates to compounds of Formula III which are useful for the preparation of some compounds of Formula I.

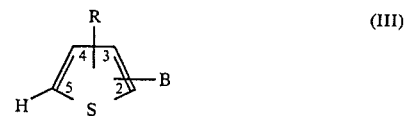

wherein

B is

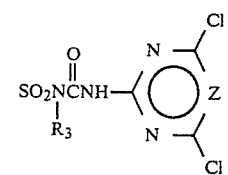

R is C$_1$–C$_4$ alkyl, C$_3$ alkenyl, OCH$_3$, NO$_2$, Cl, Br, SO$_2$NR$_1$R$_2$ or SO$_2$N(OCH$_3$)CH$_3$;

R$_1$ and R$_2$ are independently C$_1$–C$_3$ alkyl;

provided that (a) B may not be in the 4-position of the thiophene ring; and (b) when B is in the 3-position and R is in the 2-position, then R is other than Cl, Br or CH$_3$.

DETAILED DESCRIPTION

Synthesis Disclosure

The herbicidal compounds of this invention can be made by one of several routes. The nature of the substituents involved determine the preferred method of preparation. As shown in Equation 1, many compounds of Formula Ia can be prepared by combining an appropriate amine of Formula NHR$_4$R$_5$ with an appropriately substituted thiophenesulfonyl isocyanate of Formula II; R, X, Y, Z, Y$^1$ and Q being as previously defined.

Equation 1

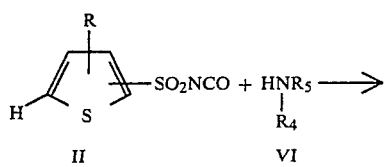

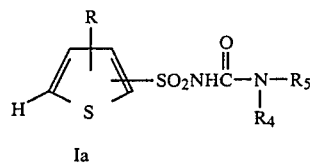

The reaction is best carried out in inert aprotic solvents such as methylene chloride, acetonitrile or tetrahydrofuran at ambient temperature and pressure. The mode of addition is not critical; however, it is often convenient to add the sulfonyl isocyanate to a stirred suspension of the aminoheterocycle. Since such isocyanates are usually liquids, or low melting solids soluble in the solvents used, their addition is more easily controlled. Time of reaction is between 1 hour and 24 hours.

The reaction is generally exothermic. In some cases, the desired product crystallizes from the reaction medium in pure form. Products soluble in the reaction mixture are isolated by evaporation of the solvent, trituration of the solid residue with solvents such as 1-chlorobutane, pentane or ethyl ether and filtration.

Compounds of Formula I can also be prepared by the method described in Equation 2.

Equation 2

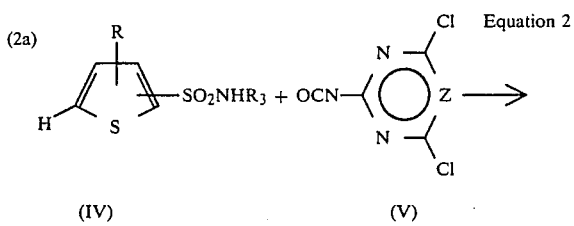

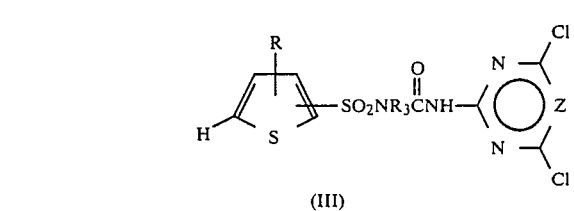

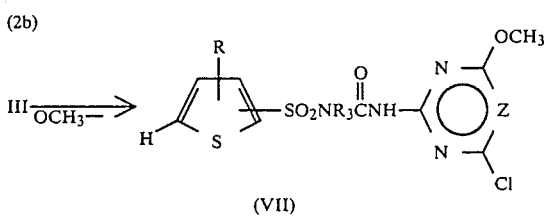

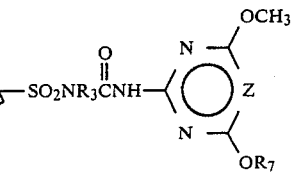

wherein R and Z are as previously defined, and $R_7$ is $C_1$-$C_3$ alkyl, $CH_2CH=CH_2$ or $CH_2C\equiv CH$.

Reaction Step (2a)

In Reaction Step (2a), a thiophenesulfonamide of Formula IV is contacted with a heterocyclic isocyanate of Formula V to yield a sulfonylurea of Formula III.

The heterocyclic isocyanates used in Reaction (2a) may be prepared according to methods described in Swiss Pat. No. 579,062, U.S. Pat. No. 3,919,228, U.S. Pat. No. 3,732,223 and Angew Chem. Int. Ed. 10, 402 (1976), the disclosures of which are herein incorporated by reference.

The thiophene sulfonamide and the heterocyclic isocyanate (V) are contacted in the presence of an inert organic solvent, for example, acetonitrile, tetrahydrofuran (THF), toluene, acetone or butanone. Optionally, a catalytic amount of a base, such as 1,4-diazabicyclo[2.2.2]octane (DABCO), potassium carbonate, sodium hydride or potassium tert-butoxide, may be added to the reaction mixture. The quantity of base constituting a catalytic amount would be obvious to one skilled in the art. The reaction mixture is preferably maintained at a temperature of about 25° to 110° C., and the product can generally be recovered by cooling and filtering the reaction mixture. For reasons of efficiency and economy, the preferred solvents are acetonitrile and THF, and the preferred temperature range is about 60° to 85° C.

Reaction Steps (2b) and (2c)

In Reaction Steps (2b) and (2c), one or two of the chlorine atoms on the pyrimidinyl or triazinyl ring of the compound of Formula III is displaced by an alcohol. Generally, this may be done by contacting the compound of Formula III with methanol or methoxide. Thus, in Reaction Step 2b, a compound of Formula III may be contacted with at least one equivalent of methanol. This reaction is sluggish, however, and it is preferred to contact the compound of Formula III with at least two equivalents of sodium methoxide in either methanol, acetonitrile, THF or dimethylformamide.

It should be noted that two equivalents of methoxide are required for Reaction Step (2b) whereas only one equivalent of methanol is needed for the same process. This difference is due to the reaction between the methoxide and the sulfonamide of Formula III. When methoxide is used, the first equivalent of base removes a proton from the sulfonamide nitrogen, and it is only the second equivalent which effects displacement of the halogen. As a result, two equivalents of methoxide are required. The resulting salt must be acidified, e.g., with sulfuric, hydrochloric or acetic acid, to yield a compound of Formula VII. Applicant, of course, does not intend to be bound by the mechanism described above.

In Reaction Step (2c) a compound of Formula VII, is contacted with either one equivalent of alkanol, $R_7OH$, or with two equivalents of alkoxide, $R_7O^-$ where $R_7$ is as described above.

When $R_7=CH_3$, Reaction Steps (2b) and (2c) may be combined. Thus, a compound of Formula III may be contacted either with at least two equivalents of methanol, or with at least three equivalents of methoxide. In Reaction Step 2b, certain reaction conditions will favor displacement of only one chlorine atom. These conditions are the use of low temperatures and the slow addition of the stoichiometric amount of alkoxide or alkoxide-generating base to the medium containing the compound of Formula III.

Both Reaction Steps (2b) and (2c) are preferably run at temperatures within the range of about $-10°$ to $80°$ C., the range of about $0°$ to $25°$ C. being more preferred. Reaction Steps (2b) and (2c) are more sluggish when alkanol is used instead of alkoxide, and more drastic conditions are required for the reaction to go to completion. Thus, higher temperatures, up to and including the boiling point of the alkanol itself, are required.

Alternatively, certain compounds of structure I may also be prepared according to Equation 3:

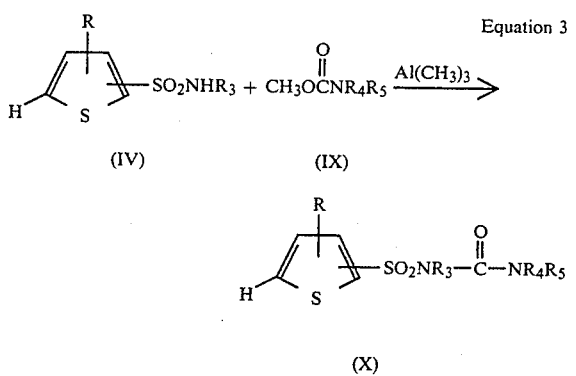

wherein R, $R_3$, $R_4$ and $R_5$ are as previously defined.

The reaction of Equation 3 is best carried out in an inert solvent such as methylene chloride at $10°-45°$ C. and ambient pressure. The preferred mode of addition is to add trimethylaluminum to a solution or slurry of the sulfonamide (IV), a mildly exothermic reaction occurs accompanied by the evolution of gas. The addition of the heterocyclic carbamate (IX) is then made and the mixture is stirred at ambient to reflux temperature for 6 to 48 hours. The addition of aqueous acid such as dilute hydrochloric or acetic acid removes inorganic salts from the product contained in the organic phase. Evaporation of the methylene chloride yields the crude product which can be purified by recrystallization or column chromatography.

Carbamyl chlorides (IXa) of the heterocyclicamines (where $R_4$ is not H) can react with alkali metal salts of thiophenesulfonamides (IVa) as shown in Equation 4.

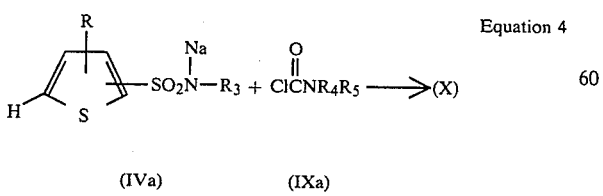

The reaction of Equation 4 is best carried out by adding a slurry or solution of the metal salt (IVa) to a solution of the chloroformate using inert solvents such as tetrahydrofuran, ethyl ether or dimethylformamide. The reaction mixture is stirred for 6 to 48 hours at $0°$ C. to reflux. Isolation of the desired product (X) is carried out by filtering off the inorganic salt by-product and evaporation of the solvent. Purification of the product is carried out as described for Equation 3.

The intermediates (IX) and (IXa) can be prepared by the reaction of the appropriate heteroamines with sodium hydride or similar alkali metal hydride in an inert solvent such as tetrahydrofuran, acetonitrile, or ether at ambient temperature to reflux followed by addition of the resulting solution or slurry to an excess of methyl chloroformate in the same solvent to prepare the carbamate (IX) or an excess of phosgene to obtain the carbamyl chloride (IXa). After removal of the precipitated salt, the solvent is removed by evaporation to leave the desired intermediate (IX or IXa) as a residue. This crude product can be used without further purification.

Carbamates (XI) or carbamyl chlorides (XIa) prepared from sulfonamides of structure IV can react with heterocyclicamines (VI) according to Equation 5 to yield compounds of structure (X).

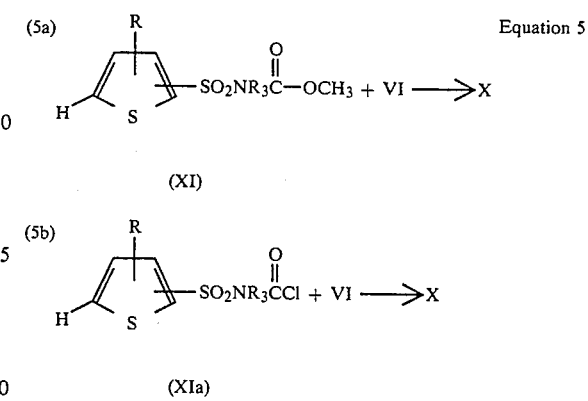

The method of Equation 5 is especially useful where $R_3$ is $CH_3$. It is carried out by adding the preformed sulfonamide derivatives (XI or XIa) to an alkali metal salt of the heterocyclicamine (VI) prepared as previously described, in an inert solvent such as used for Equation 3 at $0°$ C. to reflux during 6 to 48 hours. The isolation and purification of the product can be performed also as described above.

The sulfonyl isocyanates (II) used in Equation 1 are novel compounds. These can be prepared as shown in Equations 6 and 7.

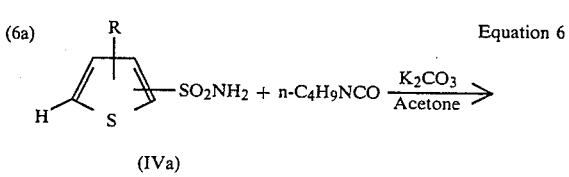

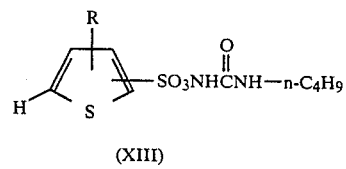

(6b)

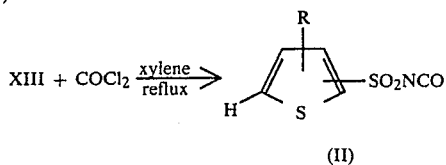

(II)

The reaction of Equation 6a is best carried out by combining equivalent amounts of the sulfonamide, the alkyl isocyanate ($C_4$–$C_{10}$ alkyl) and potassium carbonate in a polar solvent such as acetone and stirring for 1–24 hours between ambient and reflux temperature. The product is isolated by pouring the mixture into ice-water, adjusting the pH to about 2 and isolating the product (Formula XIII) by filtration or extraction into methylene chloride.

The product from Equation 6a is dried thoroughly, placed in an aprotic organic solvent (b.p. 120°–180°) such as xylene or chlorobenzene and heated to reflux under a dry ice cooled condenser. Phosgene is passed into the mixture until an excess is present whereupon the reflux temperature drops to 120° and remains at 120° without further addition of phosgene.

Alternatively, these sulfonyl isocyanates can be prepared by combining an alkyl isocyanate ($C_4$–$C_{10}$) with the thiophenesulfonamide (Formula IVa) in an inert solvent as above and contacting this mixture with phosgene at 120°–150°. A catalytic amount of a tertiary amine such as triethylamine, pyridine, or 1,4-diazabicyclo[2,2,2]octane can be used to shorten the reaction time. An additional method involves the reaction of thionyl chloride with a sulfonamide of Formula IVa and reaction of the resultant intermediate (XIV) with phosgene according to Equation 7.

(7a)                                          Equation 7

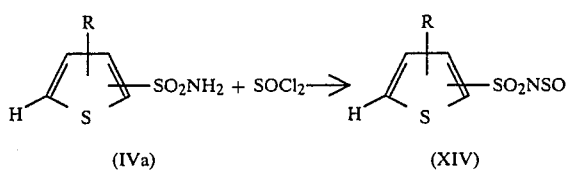

(IVa)                          (XIV)

(7b)

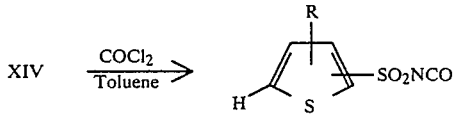

The reaction of the sulfonamide with thionyl chloride can be carried out in excess thionyl chloride, using the latter as the solvent. The excess thionyl chloride is removed by distillation to yield the intermediate (XIV). This product is placed in an inert, aprotic solvent such as toluene, xylene or chlorobenzene and the mixture is reacted with phosgene at 80°–140° to yield the desired sulfonyl isocyanate.

Precursors to the required sulfonyl chlorides and sulfonamides are prepared by a variety of synthetic routes depending on the chemical properties of R and its position on the thiophene ring.

Direct sulfonation or chlorosulfonation to sulfonic acid or sulfonyl chloride derivatives can be carried out according to references cited in "Thiophene and its Derivatives," H. D. Hartough, Interscience, New York, 1952. The structure of sulfonation products of 3-alkyl thiophenes has been reported as uncertain. Nuclear magnetic resonance studies indicate the chlorosulfonation occurs predominantly at the 2- rather than the 5-position.

Sulfonic acids are readily converted to sulfonyl chlorides, using methods well known in the art, by chlorinating agents such as phosphorus pentachloride, phosphorus oxychloride or thionyl chloride. A mixture of sulfuryl chloride in dimethylformamide can also be used to prepare thiophenesulfonyl chlorides of active thiophene intermediates according to the method of E. Testa et al., *Helv. Chim. Acta.*, 47, 766 (1963).

Other intermediates can be prepared via lithiation reactions. A review of this chemistry appears in Organic Reactions, Vol. 26., Gschwind, H. W. and Rodriguez, H. R., John Wiley and Sons, Inc., New York, 1979. Examples of the application of this chemistry to the preparation of intermediates used here is shown in the following equations.

Equation 8 shows the preparation of sulfamyl thiophene sulfonamides via lithiated intermediates.

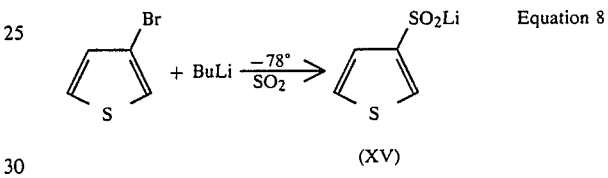

(XV)

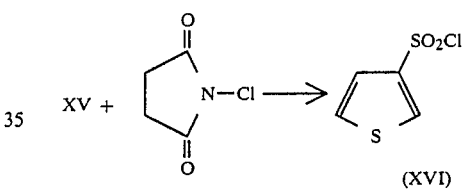

(XVI)

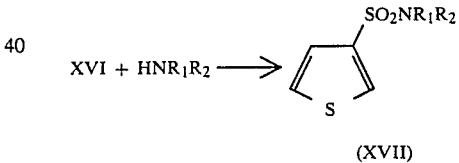

(XVII)

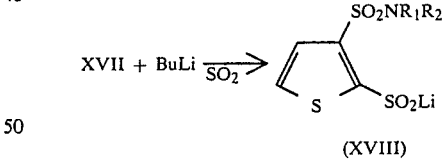

(XVIII)

As shown in Equation 8, 3-bromothiophene is converted to 3-lithiothiophene at −78° in an inert solvent such as tetrahydrofuran and the mixture is then contacted with sulfur dioxide. The resultant lithio sulfinate is stirred at room temperature in acetic acid or aqueous 2-propanol with N-chlorosuccinimide to yield the 3-thiophenesulfonyl chloride (XVI). This product is then contacted with an amine, $HNR_1R_2$ wherein $R_1$ and $R_2$ are as previously defined. The 3-thiophenesulfonamide (XVII), thus formed is reacted with butyl lithium at −40° to 0° C. followed by sulfur dioxide to form the lithio 3-sulfamyl-2-thiophenesulfinate (XVIII) which is converted to the sulfonyl chloride as described above. Conversion of this sulfonyl chloride to the sulfonamide and sulfonyl isocyanate is carried out as previously described.

The synthesis of other intermediates via lithiation is shown in Equation 9, wherein $R_6$ is optionally Cl, Br, $C_1$–$C_4$ alkyl, $C_3$ alkenyl or $OCH_3$.

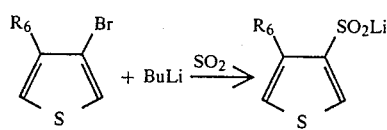

Equation 9

(XIX)

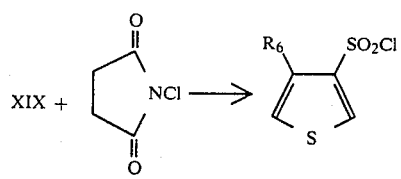

The reactions described in Equation 9 are carried out in the same manner as those described in Equation 8 as would be expected by one skilled in the art. Displacement of activated halogen atoms from the thiophene nucleus by benzyl mercaptan and chlorination of the resulting product is also a useful route to intermediates for compounds of this invention as illustrated by Equation 10.

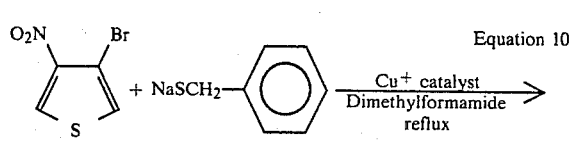

Equation 10

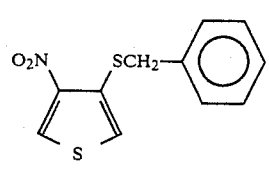

(XX)

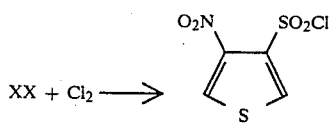

(XXI)

The reaction of benzyl mercaptan with a halothiophene, wherein the halo atom is susceptible to replacement by a nucleophile, is best carried out in an inert polar, high boiling solvent such as dimethylformamide or N-methylpyrrolidone at reflux in the presence of a copper catalyst over six to forty eight hours. The thioether intermediate (XX) is converted to the sulfonyl chloride (XXI) by passing chlorine gas into aqueous hydrochloric acid or acetic acid solution or suspension of (XX).

Disulfides such as structure XXII, reported by Henriksen and Autruys, *Acta. Chem. Scands.*, 24, 2629 (1970), are also useful intermediates for conversion to sulfonyl chlorides as shown in Equation 11.

Equation 11

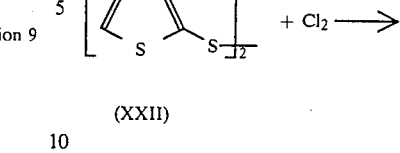

(XXII)

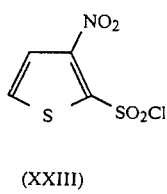

(XXIII)

The chlorination shown in Equation 11 is carried out in the same manner as described for the chlorination of structure XX.

Alternatively, the diazotization reaction of thiophene amines to sulfonyl chlorides such as structure XXIV shown in Equation 12 are carried out according to the general procedure of H. L. Yale and F. Sowinski, *J. Org. Chem.*, 25, 1824 (1960).

Equation 12

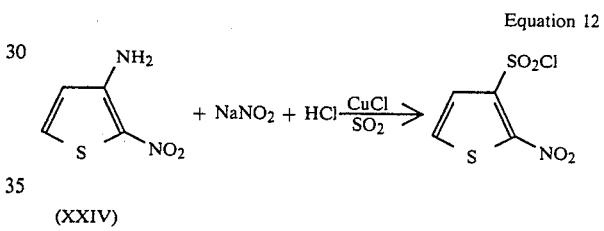

(XXIV)

The heterocyclicamine intermediates $R_4R_5NH$ in which $R_4$ is $CH_3$ may be prepared by the following procedure, or by modifications thereof:

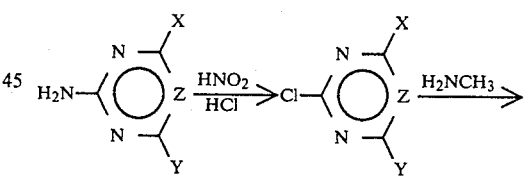

(XXVII)   (XXVIII)

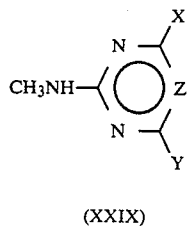

(XXIX)

A solution of the amine (XXVII) in concentrated hydrochloric acid is treated with an aqueous sodium nitrite solution and the chloro compound (XXXIV) is isolated in the usual manner by filtration of the acidic solution (see for example, Bee and Rose, *J. Chem. Soc. C.*, 2051 (1966) for the case in which Z is CH and X and Y are $OCH_3$). Displacement of the chlorine may be accomplished by heating with an excess of methylamine in water to obtain the methylaminoheterocycle (XXIX).

N-Methoxyaminoheterocycles can be prepared by procedures reported in the literature [see, for example, Belgian Pat. No. 618,563 and J. T. Shaw, et. al., *J. Org. Chem.*, 27, 2054 (1962)] and illustrated below:

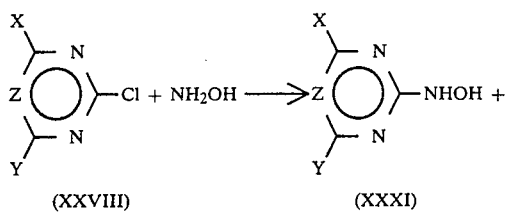

(XXVIII)    (XXXI)

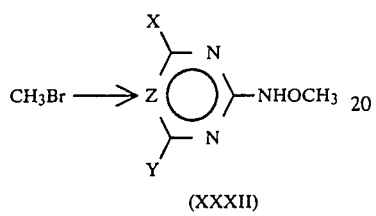

(XXXII)

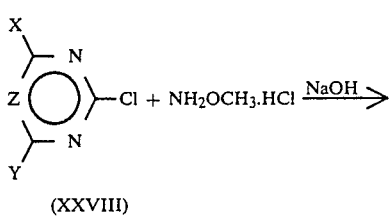

(XXVIII)

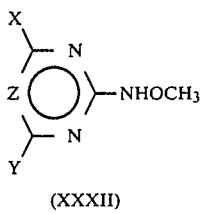

(XXXII)

Chloro compound (XXVIII) is reacted with hydroxylamine to form derivative (XXXI) which may be alkylated with methyl bromide to afford the N-methoxy heterocyclic amine (XXXII). This compound may alternately be prepared in one step by the treatment of (XXVIII) and o-methyl hydroxylamine hydrochloride with an alkali metal hydroxide such as sodium hydroxide.

Heterocyclic isocyanates of Formula V may be prepared according to methods described in Swiss Pat. No. 579,062, U.S. Pat. No. 3,919,228, U.S. Pat. No. 3,732,233 and *Angew. Chem. Ing. Ed.*, 10, 402 (1976), the disclosures of which are herein incorporated by reference.

The synthesis of heterocyclic amine derivatives has been reviewed in "The Chemistry of Heterocyclic Compounds," a series published by Interscience Publ., New York and London. 2-Aminopyrimidines are described by D. J. Brown in "The Pyrimidines", Vol. XVI of the above series. The 2-amino-1,3,5-triazines are reviewed in "s-Triazines and Derivatives," Vol. XIII of the same series. The synthesis of triazines is also described by F. C. Schaefer, U.S. Pat. No. 3,154,547 and K. R. Huffman and F. C. Schaefer, *J. Org. Chem.*, 28, 1812-1821 (1963). The synthesis of the bicyclic heterocyclic amines (XXV) and (XXVI) wherein $Y^1$ is as previously defined is described in the unexamined European Pat. No. 15-683, published Sept. 17, 1980.

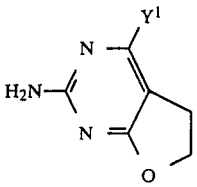 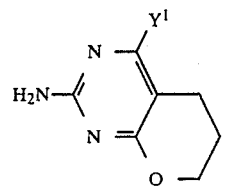

XXV    XXVI

In the following examples, unless otherwise indicated, all parts are by weight and temperatures in °C.

EXAMPLE 1

3-Bromo-4-methylthiophene

To 84 g of 3,4-dibromothiophene in 300 ml of anhydrous ethyl ether under nitrogen at −75° C. was added dropwise 217 ml of 1.6M butyl lithium in hexane during 50 minutes. After the addition was complete, the mixture was stirred for 30 minutes at −70° C. to −75° C. and then 53 g of dimethyl sulfate was added cautiously, dropwise. When half of the addition was completed, the temperature rose suddenly to −50° C. whereupon the addition was stopped and the mixture cooled again to −75° C.; the addition of dimethyl sulfate was resumed keeping the temperature at below −70° C. After the completion of the addition, which required 45 minutes, the mixture was stirred for two and one half hours at −75°, allowed to warm to ambient temperature and stirred for 18 hours. The mixture was then filtered and the filtrate evaporated to yield an oil. This oil was taken up in methylene chloride, washed with 100 ml of 1N aqueous sodium hydroxide, dried over sodium sulfate, concentrated in vacuo and the product distilled at 68°-72° under 15 mm mercury pressure, $n_D^{25}$ 1.5610.

EXAMPLE 2

Lithium 4-methyl-3-thiophenesulfinate

To 30 g of 3-bromo-4-methylthiophene in 150 ml of anhydrous ethyl ether under nitrogen at −70° to −75° C. was added, cautiously, during 30 minutes 111 ml of 1.6M butyl lithium in hexane. The mixture was stirred for an additional thirty minutes and then 30 ml of liquified sulfur dioxide was added at such a rate that the temperature of the reaction mixture was maintained below −70° C. Upon completion of the addition, the mixture was stirred for an additional 90 minutes at −75° C. and then allowed to stand overnight at room temperature. The resulting precipitate was filtered and washed with ethyl ether, dried in air and in vacuo under nitrogen to yield 30 g of the desired salt, m.p. >250° C.

EXAMPLE 3

4-Methyl-3-thiophenesulfonamide

To 34 g of lithium 4-methyl-3-thiophenesulfinate in 220 ml of water cooled to 10° C. was added a suspension of 26.7 g of N-chlorosuccinimide in 80 ml of 2-propanol portionwise during 5 minutes. An additional 75 ml of 2-propanol was added to dissolve the reagents and the mixture was stirred for 70 minutes at 20° C. A large excess (1 liter) of water was then added and the mixture was extracted with methylene chloride 3 times. The methylene chloride portions were combined, dried over sodium sulfate and the solvent removed in vacuo to yield 4-methyl-3-thiophenesulfonyl chloride. This product was dissolved in 100 ml of tetrahydrofuran and 70 ml of concentrated aqueous ammonia was then added, and the mixture stirred overnight. Concentration of the resultant solution in vacuo and dilution of the residue with water yielded a solid which was filtered, washed with water and stirred with hot 1-chlorobutane, cooled and filtered to yield 14 g of the desired solid compound, m.p. 73°–85°.

EXAMPLE 4

N-Butylaminocarbonyl-4-methyl-3-thiophenesulfonamide

4-Methyl-3-thiophenesulfonamide (22 g), 125 ml of methyl ethyl ketone, 16.6 g of potassium carbonate and 14.3 g of butyl isocyanate was stirred at reflux for six hours, allowed to stand overnight and then evaporated to a syrup. Water (150 ml) was added to the residue and the mixture was filtered to remove a small amount of solid. The filtrate was acidified, cooled and the resulting intermediate was filtered off. It melted at 126°–131° C.

EXAMPLE 5

4-Methyl-3-thiophenesulfonyl isocyanate

A mixture of 18.8 g of N-butylaminocarbonyl-4-methyl-3-thiophenesulfonamide, 0.3 g of 1,4-diaza-[2.2.2.]bicyclooctane and 100 ml of dry xylenes was heated to reflux (136° C.) and 7.4 g of phosgene was then added at a rate to maintain the temperature at above 125°. The mixture was refluxed for three and one half hours after the addition was completed. It was then cooled, filtered and concentrated in vacuo to yield a dark oil, (15 g) which showed absorption in the infrared spectrum at 2250 cm$^{-1}$. This intermediate was used without further purification.

EXAMPLE 6

N-[(4,6-Dimethoxypyrimidin-2-yl)aminocarbonyl]-4-methyl-3-thiophenesulfonamide

A solution of 2 g of 4-methyl-3-thiophenesulfonyl isocyanate in 5 ml of dry acetonitrile was added to 1.5 g of 2amino-4,6-dimethoxypyrimidine in 20 ml of acetonitrile with stirring. The mixture was stirred for 16 hours at ambient temperature and filtered to yield 1.5 g of the desired product, m.p. 175°–178°.

EXAMPLE 7

N-[(4,6-Dimethoxy-1,3,5-triazin-2-yl)aminocarbonyl]-4-methyl-3-thiophenesulfonamide A solution of 2 g of 4-methyl-3-thiophenesulfonyl isocyanate was added to a suspension of 1.5 g of 2-amino-4,6-dimethoxy-1,3,5-triazine in 20 ml of tetrahydrofuran and the resulting mixture stirred for 16 hours at ambient temperature. The precipitate thus obtained was filtered off and recrystallized to yield 1.5 g of the desired product, m.p. 154°–156°.

EXAMPLE 8

4-Bromo-N-[(4-methoxy-6-methyl-1,3,5-triazin-2-yl)aminocarbonyl]-3-thiophenesulfonamide To 1.1 g of 2-amino-4-methoxy-6-methyl-1,3,5-triazine in 20 ml of tetrahydrofuran was added 2 g of 4-bromo-3-thiophenesulfonyl isocyanate in 5 ml of tetrahydrofuran. The mixture was then stirred and warmed on a steam bath for 15 minutes and allowed to stir at ambient temperature for 70 hours. It was then heated to reflux for 2 hours, cooled to 10° C., filtered and the filtrate evaporated. The residual oil was triturated to yield the desired product as a solid which after recrystallization from acetonitrile melted at 180°–183°, yield 1.5 g.

Anal. Calcd. for: C, 29.4; H. 2.5; N, 17.3; Found: C, 29.8; H. 2.3; N, 17.3.

EXAMPLE 9

N-(Butylaminocarbonyl)-4-nitrothiophene-2-sulfonamide

A stirred suspension of 10 g of 4-nitrothiophene-2-sulfonamide, 6 g of n-butyl isocyanate and 7 g of anhydrous potassium carbonate in 100 ml of acetone was heated to reflux for 3 hours. The resultant viscous mixture was poured into ice-water and the pH adjusted to 2 by the addition of concentrated hydrochloric acid. The resulting tarry precipitate thus obtained was extracted into methylene chloride, separated from the aqueous phase, dried over magnesium sulfate, filtered and concentrated in-vacuo. The residue which showed absorption peaks by NMR at 0.7 to 1.7 (multiplet), consistent for butyl and at 8.3 and 8.5, consistent for the thiophene ring was used without further purification in the following example.

EXAMPLE 10

4-Nitrothiophene-2-sulfonyl isocyanate

N-Butylaminocarbonyl-4-nitrothiophenesulfonamide from the preceeding example was stirred in 100 ml of xylene in a round bottom flask equipped with a dry ice condenser, gas inlet tube, thermometer and stirrer. When the temperature of the mixture reached 130° phosgene was passed in until the temperature went down to 120°. The phosgene addition was stopped until the temperature returned to 130° and the phosgene addition was resumed. This cycling was continued until the reflux temperature would not rise above 120° with the phosgene off, indicating an excess of phosgene in the reaction mixture. After cooling, the mixture was filtered and the filtrate concentrated in vacuo to yield 4.8 g of the desired sulfonyl isocyanate as an oil. It showed an infrared absorption peak at 2200 cm$^{-1}$, consistent for the desired sulfonyl isocyanate.

EXAMPLE 11

3-Methyl-2-thiophenesulfonyl isocyanate

Method A

A mixture of 9 g of 3-methyl-2-thiophenesulfonamide and 100 ml of thionyl chloride was refluxed with stirring overnight. The unreacted thionyl chloride was then distilled off in-vacuo leaving an oil residue, which was dissolved in toluene, heated to reflux and treated with a slow stream of phosgene gas while maintaining the temperature at above 90° C. After eight hours, 0.5 g of pyridine was added and the phosgenation was continued for four more hours. Evaporation of the toluene in-vacuo yielded an oil residue, which showed an absorption peak by infrared analysis at 2200 cm$^{-1}$ consistent for the desired sulfonyl isocyanate. This product was used without further purification.

Method B

In this procedure, N-(butylaminocarbonyl)-3-methyl-2-thiophenesulfonamide is prepared, isolated and treated with phosgene to yield the desired sulfonyl isocyanate.

To 150 ml of acetone and 3-methyl-2-thiophenesulfonamide was added 11 g of n-butyl isocyanate and 14 g of anhydrous potassium carbonate. After stirring at ambient temperature for 24 hours, the mixture was concentrated to ⅔ of its volume and poured into ice-water. The pH was adjusted to 3 by the addition of hydrochloric acid and the solid thus obtained was filtered, air dried and triturated with 1-chlorobutane to yield 10.6 g of N-(butylaminocarbonyl)-3-methyl-2-thiophenesulfonamide melting at 144°–146°. It showed absorption peaks by NMR (60 MC) at 2.6 δ (singlet, CH₃), 1–1.8 δ (mult., C₃H₇), 3.42 δ (trip., N—CH₂— of butyl) and at 7.1 δ and 7.7 δ (2 doublets for CH's of thiophene) consistent for the desired structure.

Nine grams of the above product was dissolved in xylene at 135° C. and phosgene was passed into the solution until the temperature dropped to 120°. The phosgene addition was continued and the product worked up as described for Example 2. The product thus obtained showed an infrared absorption peak at 2200 cm$^{-1}$, consistent for the desired sulfonyl isocyanate.

EXAMPLE 12

N-[(4-Methoxy-6-methyl-2-pyrimidinyl)aminocarbonyl]-4-nitrothiophene-2-sulfonamide To 1.4 g of 2-amino-4-methoxy-6-methylpyrimidine in 25 ml of anhydrous acetonitrile was added 2.4 g of 4-nitrothiophene-2-sulfonyl isocyanate with stirring at ambient temperature. After stirring for sixteen hours, the mixture was filtered and the precipitate washed with 1-chlorobutane. It melted at 155° with decomposition and showed an infrared absorption spectrum with peaks at 1700, 1620 and 1570 cm$^{-1}$ consistent for the desired structure.

EXAMPLE 13

N-[(4-Methoxy-6-methyl-1,3,5-triazin-2-yl)aminocarbonyl]-4-nitrothiophene-2-sulfonamide To 1.4 g of 2-amino-4methoxy-6-methyl-1,3,5-triazine suspended in 25 ml of anhydrous acetonitrile with stirring at ambient temperature was added 2.4 g of 4-nitrothiophene-2-sulfonyl isocyanate. After stirring for sixteen hours at ambient temperature, the product which was present as a precipitate was removed by filtration and washed with 1-chlorobutane. It melted at 188° with decomposition and showed infrared absorption spectrum peaks at 1740, 1600 and 1560 cm$^{-1}$ consistent for the desired aminocarbonylsulfonamide structure.

By applying the methods described in Equations 1–12 and Examples 1–13, the compounds of Tables I–VIII-a can be prepared by one skilled in the art.

TABLE I

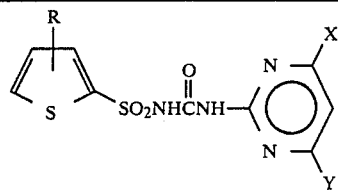

| R | X | Y |
|---|---|---|
| 3-CH₃ | CH₃ | CH₃ |
| 3-CH₃ | OCH₃ | CH₃ |

TABLE I-continued

| R | X | Y |
|---|---|---|
| 3-CH₃ | OCH₃ | OCH₃ |
| 3-Cl | CH₃ | CH₃ |
| 3-Cl | OCH₃ | CH₃ |
| 3-Cl | OCH₃ | OCH₃ |
| 3-Br | CH₃ | CH₃ |
| 3-Br | OCH₃ | CH₃ |
| 3-Br | OCH₃ | OCH₃ |
| 3-NO₂ | CH₃ | CH₃ |
| 3-NO₂ | OCH₃ | CH₃ |
| 3-NO₂ | OCH₃ | OCH₃ |
| 3-SO₂N(CH₃)₂ | CH₃ | CH₃ |
| 3-SO₂N(CH₃)₂ | OCH₃ | CH₃ |
| 3-SO₂N(CH₃)₂ | OCH₃ | OCH₃ |
| 3-OCH₃ | CH₃ | CH₃ |
| 3-OCH₃ | OCH₃ | CH₃ |
| 3-OCH₃ | OCH₃ | OCH₃ |
| 3-CH₂CH₃ | CH₃ | CH₃ |
| 3-CH₂CH₃ | OCH₃ | CH₃ |
| 3-CH₂CH₃ | OCH₃ | OCH₃ |
| 3-CH(CH₃)₂ | CH₃ | CH₃ |
| 3-CH(CH₃)₂ | OCH₃ | CH₃ |
| 3-CH(CH₃)₂ | OCH₃ | OCH₃ |
| 3-CH₂CH(CH₃)₂ | CH₃ | CH₃ |
| 3-CH₂CH(CH₃)₂ | OCH₃ | CH₃ |
| 3-CH₂CH(CH₃)₂ | OCH₃ | OCH₃ |
| 3-SO₂N(CH₃)[CH(CH₃)₂] | CH₃ | CH₃ |
| 3-SO₂N(CH₃)[CH(CH₃)₂] | OCH₃ | CH₃ |
| 3-SO₂N(CH₃)[CH(CH₃)₂] | OCH₃ | OCH₃ |
| 3-SO₂N(OCH₃)CH₃ | CH₃ | CH₃ |
| 3-SO₂N(OCH₃)CH₃ | OCH₃ | CH₃ |
| 3-SO₂N(OCH₃)CH₃ | OCH₃ | OCH₃ |
| 3-CH₂CH=CH₂ | CH₃ | CH₃ |
| 3-CH₂CH=CH₂ | OCH₃ | CH₃ |
| 3-CH₂CH=CH₂ | OCH₃ | OCH₃ |
| 3-CH₃ | H | CH₃ |
| 3-CH₃ | Cl | CH₃ |
| 3-CH₃ | Br | CH₃ |
| 3-CH₃ | CH₂CH₃ | CH₃ |
| 3-CH₃ | OCH₂CH₃ | CH₃ |
| 3-CH₃ | OCH₂CH₂CH₃ | CH₃ |
| 3-CH₃ | CF₃ | CH₃ |
| 3-CH₃ | SCH₃ | CH₃ |
| 3-CH₃ | CH₂OCH₃ | CH₃ |
| 3-Cl | CH₂OCH₃ | CH₃ |
| 3-Br | CH₂OCH₃ | CH₃ |
| 3-NO₂ | CH₂OCH₃ | CH₃ |
| 3-SO₂N(CH₃)₂ | CH₂OCH₃ | CH₃ |
| 3-CH₃ | CH₂OCH₃ | OCH₃ |
| 3-Cl | CH₂OCH₃ | OCH₃ |
| 3-Br | CH₂OCH₃ | OCH₃ |
| 3-NO₂ | CH₂OCH₃ | OCH₃ |
| 3-SO₂N(CH₃)₂ | CH₂OCH₃ | OCH₃ |
| 3-CH₃ | OCH₂CH=CH₂ | CH₃ |
| 3-CH₃ | OCH₂C≡CH | CH₃ |
| 3-NO₂ | OCH₂CH=CH₂ | CH₃ |
| 3-SO₂N(CH₃)₂ | OCH₂CH=CH₂ | CH₃ |
| 3-Cl | OCH₂CH=CH₂ | CH₃ |
| 3-Br | OCH₂CH=CH₂ | CH₃ |
| 4-CH₃ | CH₃ | CH₃ |
| 4-CH₃ | OCH₃ | CH₃ |
| 4-CH₃ | OCH₃ | OCH₃ |
| 4-Cl | CH₃ | CH₃ |
| 4-Cl | OCH₃ | CH₃ |
| 4-Cl | OCH₃ | OCH₃ |
| 4-Br | CH₃ | CH₃ |
| 4-Br | OCH₃ | CH₃ |
| 4-Br | OCH₃ | OCH₃ |
| 4-NO₂ | CH₃ | CH₃ |
| 4-NO₂ | OCH₃ | CH₃ |
| 4-NO₂ | OCH₃ | OCH₃ |
| 4-SO₂N(CH₃)₂ | CH₃ | CH₃ |

TABLE I-continued

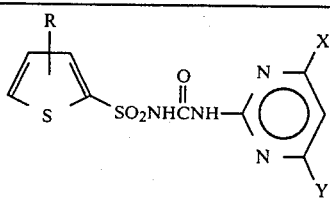

| R | X | Y |
|---|---|---|
| 4-SO₂N(CH₃)₂ | OCH₃ | CH₃ |
| 4-SO₂N(CH₃)₂ | OCH₃ | OCH₃ |
| 4-OCH₃ | CH₃ | CH₃ |
| 4-OCH₃ | OCH₃ | CH₃ |
| 4-OCH₃ | OCH₃ | OCH₃ |
| 4-CH₂CH₃ | CH₃ | CH₃ |
| 4-CH₂CH₃ | OCH₃ | CH₃ |
| 4-CH₂CH₃ | OCH₃ | OCH₃ |
| 4-CH(CH₃)₂ | CH₃ | CH₃ |
| 4-CH(CH₃)₂ | OCH₃ | CH₃ |
| 4-CH(CH₃)₂ | OCH₃ | OCH₃ |
| 4-CH₂CH(CH₃)₂ | CH₃ | CH₃ |
| 4-CH₂CH(CH₃)₂ | OCH₃ | CH₃ |
| 4-CH₂CH(CH₃)₂ | OCH₃ | OCH₃ |
| 4-SO₂N(CH₃)[CH(CH₃)₂] | CH₃ | CH₃ |
| 4-SO₂N(CH₃)[CH(CH₃)₂] | OCH₃ | CH₃ |
| 4-SO₂N(CH₃)[CH(CH₃)₂] | OCH₃ | OCH₃ |
| 4-SO₂N(OCH₃)CH₃ | CH₃ | CH₃ |
| 4-SO₂N(OCH₃)CH₃ | OCH₃ | CH₃ |
| 4-SO₂N(OCH₃)CH₃ | OCH₃ | OCH₃ |
| 4-CH₂CH=CH₂ | CH₃ | CH₃ |
| 4-CH₂CH=CH₂ | OCH₃ | CH₃ |
| 4-CH₂CH=CH₂ | OCH₃ | OCH₃ |
| 4-CH₃ | H | CH₃ |
| 4-CH₃ | Cl | CH₃ |
| 4-CH₃ | Br | CH₃ |
| 4-CH₃ | CH₂CH₃ | CH₃ |
| 4-CH₃ | OCH₂CH₃ | CH₃ |
| 4-CH₃ | OCH₂CH₂CH₃ | CH₃ |
| 4-CH₃ | CF₃ | CH₃ |
| 4-CH₃ | SCH₃ | CH₃ |
| 4-CH₃ | CH₂OCH₃ | CH₃ |
| 4-Cl | CH₂OCH₃ | CH₃ |
| 4-Br | CH₂OCH₃ | CH₃ |
| 4-NO₂ | CH₂OCH₃ | CH₃ |
| 4-SO₂N(CH₃)₂ | CH₂OCH₃ | CH₃ |
| 4-CH₃ | CH₂OCH₃ | OCH₃ |
| 4-Cl | CH₂OCH₃ | OCH₃ |
| 4-Br | CH₂OCH₃ | OCH₃ |
| 4-NO₂ | CH₂OCH₃ | OCH₃ |
| 4-SO₂N(CH₃)₂ | CH₂OCH₃ | OCH₃ |
| 4-CH₃ | OCH₂CH=CH₂ | CH₃ |
| 4-CH₃ | OCH₂C≡CH | CH₃ |
| 4-NO₂ | OCH₂CH=CH₂ | CH₃ |
| 4-SO₂N(CH₃)₂ | OCH₂CH=CH₂ | CH₃ |
| 4-Cl | OCH₂CH=CH₂ | CH₃ |
| 4-Br | OCH₂CH=CH₂ | CH₃ |

TABLE I-a

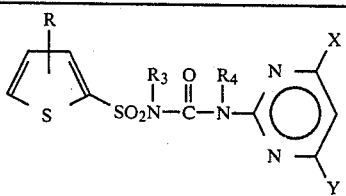

| R | R₃ | R₄ | X | Y |
|---|---|---|---|---|
| 3-CH₃ | H | CH₃ | CH₃ | CH₃ |
| 3-CH₃ | H | CH₃ | OCH₃ | CH₃ |
| 3-CH₃ | H | CH₃ | OCH₃ | OCH₃ |
| 3-CH₃ | CH₃ | CH₃ | CH₃ | OCH₃ |
| 3-Cl | H | CH₃ | CH₃ | CH₃ |
| 3-Cl | H | CH₃ | CH₃ | OCH₃ |
| 3-Cl | H | CH₃ | OCH₃ | OCH₃ |
| 3-Cl | CH₃ | CH₃ | OCH₃ | OCH₃ |
| 3-Br | H | CH₃ | CH₃ | CH₃ |

TABLE I-a-continued

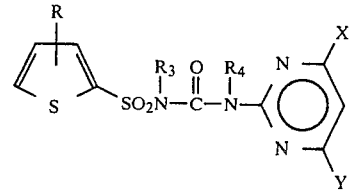

| R | R₃ | R₄ | X | Y |
|---|---|---|---|---|
| 3-Br | H | CH₃ | OCH₃ | CH₃ |
| 3-Br | H | CH₃ | OCH₃ | OCH₃ |
| 3-Br | CH₃ | CH₃ | OCH₃ | CH₃ |
| 3-NO₂ | H | CH₃ | CH₃ | CH₃ |
| 3-NO₂ | H | CH₃ | OCH₃ | CH₃ |
| 3-NO₂ | H | CH₃ | OCH₃ | OCH₃ |
| 3-NO₂ | CH₃ | CH₃ | OCH₃ | CH₃ |
| 3-SO₂N(CH₃)₂ | H | CH₃ | OCH₃ | CH₃ |
| 3-SO₂N(CH₃)₂ | H | CH₃ | OCH₃ | CH₃ |
| 3-SO₂N(CH₃)₂ | CH₃ | CH₃ | OCH₃ | OCH₃ |
| 3-CH(CH₃)₂ | H | CH₃ | CH₃ | CH₃ |
| 3-CH(CH₃)₂ | H | CH₃ | OCH₃ | CH₃ |
| 3-CH(CH₃)₂ | H | CH₃ | OCH₃ | OCH₃ |
| 3-(CH₂)₃CH₃ | H | CH₃ | CH₃ | CH₃ |
| 3-(CH₂)₃CH₃ | H | CH₃ | OCH₃ | OCH₃ |
| 3-(CH₂)₃CH₃ | CH₃ | CH₃ | OCH₃ | OCH₃ |
| 3-SO₂N(CH₃)(C₂H₅) | H | CH₃ | CH₃ | OCH₃ |
| 3-SO₂N(CH₃)(C₂H₅) | H | CH₃ | CH₃ | CH₃ |
| 3-SO₂N(CH₃)(C₂H₅) | H | CH₃ | OCH₃ | OCH₃ |
| 3-SO₂N(OCH₃)CH₃ | H | CH₃ | CH₃ | CH₃ |
| 3-SO₂N(OCH₃)CH₃ | H | CH₃ | OCH₃ | CH₃ |
| 3-SO₂N(OCH₃)CH₃ | H | CH₃ | OCH₃ | OCH₃ |
| 3-CH₃ | H | OCH₃ | CH₃ | CH₃ |
| 3-CH₃ | H | OCH₃ | OCH₃ | OCH₃ |
| 3-CH₃ | H | OCH₃ | CH₃ | OCH₃ |
| 3-CH₃ | CH₃ | OCH₃ | OCH₃ | CH₃ |
| 3-CH₃ | H | OCH₃ | Cl | CH₃ |
| 3-CH₃ | H | OCH₃ | Br | CH₃ |
| 3-CH₃ | H | OCH₃ | CH₂CH₃ | CH₃ |
| 3-CH₃ | H | OCH₃ | OCH₂CH₃ | CH₃ |
| 3-CH₃ | H | OCH₃ | OCH₂CH₂CH₃ | CH₃ |
| 3-CH₃ | H | OCH₃ | CF₃ | CH₃ |
| 3-CH₃ | H | OCH₃ | SCH₃ | CH₃ |
| 3-CH₃ | H | OCH₃ | CH₂OCH₃ | CH₃ |
| 3-Cl | H | OCH₃ | CH₂OCH₃ | OCH₃ |
| 3-Br | H | OCH₃ | CH₂OCH₃ | OCH₃ |
| 3-NO₂ | H | OCH₃ | CH₂OCH₃ | OCH₃ |
| 3-SO₂N(CH₃)₂ | H | OCH₃ | CH₂OCH₃ | OCH₃ |
| 3-OCH₃ | H | OCH₃ | CH₂OCH₃ | OCH₃ |
| 3-CH₂CH=CH₂ | H | CH₃ | OCH₃ | CH₃ |
| 3-NO₂ | H | CH₃ | OCH₂CH=CH₂ | CH₃ |
| 3-Br | H | CH₃ | OCH₂CH=CH₂ | CH₃ |
| 3-SO₂N(CH₃)₂ | H | CH₃ | OCH₂C≡CH | CH₃ |
| 4-CH₃ | H | CH₃ | CH₃ | CH₃ |
| 4-CH₃ | H | CH₃ | OCH₃ | CH₃ |
| 4-CH₃ | H | CH₃ | OCH₃ | OCH₃ |
| 4-CH₃ | CH₃ | CH₃ | CH₃ | OCH₃ |
| 4-Cl | H | CH₃ | CH₃ | CH₃ |
| 4-Cl | H | CH₃ | CH₃ | OCH₃ |
| 4-Cl | H | CH₃ | OCH₃ | OCH₃ |
| 4-Br | H | CH₃ | CH₃ | CH₃ |
| 4-Br | H | CH₃ | OCH₃ | CH₃ |
| 4-Br | H | CH₃ | OCH₃ | OCH₃ |
| 4-Br | CH₃ | CH₃ | CH₃ | CH₃ |
| 4-NO₂ | H | CH₃ | CH₃ | CH₃ |
| 4-NO₂ | H | CH₃ | OCH₃ | CH₃ |

TABLE I-a-continued

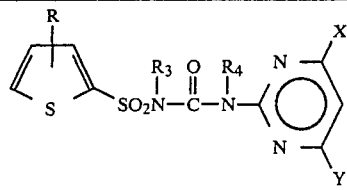

| R | $R_3$ | $R_4$ | X | Y |
|---|---|---|---|---|
| 4-NO$_2$ | H | CH$_3$ | OCH$_3$ | OCH$_3$ |
| 4-NO$_2$ | CH$_3$ | CH$_3$ | OCH$_3$ | CH$_3$ |
| 4-SO$_2$N(CH$_3$)$_2$ | H | CH$_3$ | OCH$_3$ | OCH$_3$ |
| 4-SO$_2$N(CH$_3$)$_2$ | H | CH$_3$ | OCH$_3$ | CH$_3$ |
| 4-SO$_2$N(CH$_3$)$_2$ | CH$_3$ | CH$_3$ | OCH$_3$ | CH$_3$ |
| 4-CH(CH$_3$)$_2$ | H | CH$_3$ | CH$_3$ | CH$_3$ |
| 4-CH(CH$_3$)$_2$ | H | CH$_3$ | OCH$_3$ | CH$_3$ |
| 4-CH(CH$_3$)$_2$ | H | CH$_3$ | OCH$_3$ | OCH$_3$ |
| 4-(CH$_2$)$_3$CH$_3$ | H | CH$_3$ | CH$_3$ | OCH$_3$ |
| 4-(CH$_2$)$_3$CH$_3$ | H | CH$_3$ | OCH$_3$ | OCH$_3$ |
| 4-(CH$_2$)$_3$CH$_3$ | CH$_3$ | CH$_3$ | OCH$_3$ | OCH$_3$ |
| 4-SO$_2$N(CH$_3$)(C$_2$H$_5$) | H | CH$_3$ | CH$_3$ | OCH$_3$ |
| 4-SO$_2$N(CH$_3$)(C$_2$H$_5$) | H | CH$_3$ | CH$_3$ | CH$_3$ |
| 4-SO$_2$N(CH$_3$)(C$_2$H$_5$) | H | CH$_3$ | OCH$_3$ | OCH$_3$ |
| 4-SO$_2$N(OCH$_3$)CH$_3$ | H | CH$_3$ | CH$_3$ | CH$_3$ |
| 4-SO$_2$N(OCH$_3$)CH$_3$ | H | CH$_3$ | OCH$_3$ | CH$_3$ |
| 4-SO$_2$N(OCH$_3$)CH$_3$ | H | CH$_3$ | OCH$_3$ | OCH$_3$ |
| 4-CH$_3$ | H | CH$_3$ | OCH$_3$ | CH$_3$ |
| 4-CH$_3$ | H | CH$_3$ | OCH$_3$ | OCH$_3$ |
| 4-CH$_3$ | H | CH$_3$ | OCH$_3$ | OCH$_3$ |
| 4-CH$_3$ | CH$_3$ | CH$_3$ | OCH$_3$ | CH$_3$ |
| 4-CH$_3$ | H | CH$_3$ | OCH$_3$ | Cl |
| 4-CH$_3$ | H | CH$_3$ | OCH$_3$ | Br |
| 4-CH$_3$ | H | CH$_3$ | OCH$_3$ | CH$_2$CH$_3$ |
| 4-CH$_3$ | H | CH$_3$ | OCH$_3$ | OCH$_2$CH$_3$ |
| 4-CH$_3$ | H | CH$_3$ | OCH$_3$ | OCH$_2$CH$_2$CH$_3$ |
| 4-CH$_3$ | H | CH$_3$ | OCH$_3$ | CF$_3$ |
| 4-CH$_3$ | H | CH$_3$ | OCH$_3$ | SCH$_3$ |
| 4-CH$_3$ | H | CH$_3$ | OCH$_3$ | CH$_2$OCH$_3$ |
| 4-Cl | H | CH$_3$ | OCH$_3$ | CH$_2$OCH$_3$ |
| 4-Br | H | CH$_3$ | OCH$_3$ | CH$_2$OCH$_3$ |
| 4-NO$_2$ | H | CH$_3$ | OCH$_3$ | CH$_2$OCH$_3$ |
| 4-SO$_2$N(CH$_3$)$_2$ | H | CH$_3$ | OCH$_3$ | CH$_2$OCH$_3$ |
| 4-OCH$_3$ | H | CH$_3$ | OCH$_3$ | CH$_2$OCH$_3$ |
| 4-CH$_2$CH=CH$_2$ | H | CH$_3$ | OCH$_3$ | CH$_3$ |
| 4-NO$_2$ | H | CH$_3$ | OCH$_2$CH=CH$_2$ | CH$_3$ |
| 4-Br | H | CH$_3$ | OCH$_2$CH=CH$_2$ | CH$_3$ |
| 4-SO$_2$N(CH$_3$)$_2$ | H | CH$_3$ | OCH$_2$C≡CH | CH$_3$ |

TABLE II

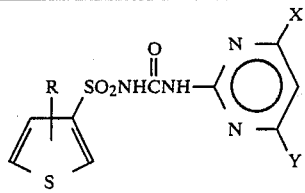

| R | X | Y |
|---|---|---|
| 2-NO$_2$ | CH$_3$ | CH$_3$ |
| 2-NO$_2$ | OCH$_3$ | CH$_3$ |

TABLE II-continued

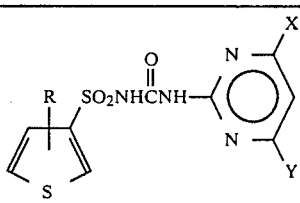

| R | X | Y |
|---|---|---|
| 2-NO$_2$ | OCH$_3$ | OCH$_3$ |
| 2-SO$_2$N(CH$_3$)$_2$ | CH$_3$ | CH$_3$ |
| 2-SO$_2$N(CH$_3$)$_2$ | OCH$_3$ | CH$_3$ |
| 2-SO$_2$N(CH$_3$)$_2$ | OCH$_3$ | OCH$_3$ |
| 2-OCH$_3$ | CH$_3$ | CH$_3$ |
| 2-OCH$_3$ | OCH$_3$ | CH$_3$ |
| 2-OCH$_3$ | OCH$_3$ | OCH$_3$ |
| 2-CH$_2$CH$_3$ | CH$_3$ | CH$_3$ |
| 2-CH$_2$CH$_3$ | OCH$_3$ | CH$_3$ |
| 2-CH$_2$CH$_3$ | OCH$_3$ | OCH$_3$ |
| 2-CH(CH$_3$)$_2$ | CH$_3$ | CH$_3$ |
| 2-CH(CH$_3$)$_2$ | OCH$_3$ | CH$_3$ |
| 2-CH(CH$_3$)$_2$ | OCH$_3$ | OCH$_3$ |
| 2-CH$_2$CH(CH$_3$)$_2$ | CH$_3$ | CH$_3$ |
| 2-CH$_2$CH(CH$_3$)$_2$ | OCH$_3$ | CH$_3$ |
| 2-CH$_2$CH(CH$_3$)$_2$ | OCH$_3$ | OCH$_3$ |
| 2-SO$_2$N(CH$_3$)[CH(CH$_3$)$_2$] | CH$_3$ | CH$_3$ |
| 2-SO$_2$N(CH$_3$)[CH(CH$_3$)$_2$] | OCH$_3$ | CH$_3$ |
| 2-SO$_2$N(CH$_3$)[CH(CH$_3$)$_2$] | OCH$_3$ | OCH$_3$ |
| 2-SO$_2$N(OCH$_3$)CH$_3$ | CH$_3$ | CH$_3$ |
| 2-SO$_2$N(OCH$_3$)CH$_3$ | OCH$_3$ | CH$_3$ |
| 2-SO$_2$N(OCH$_3$)CH$_3$ | OCH$_3$ | OCH$_3$ |
| 2-CH$_2$CH=CH$_2$ | CH$_3$ | CH$_3$ |
| 2-CH$_2$CH=CH$_2$ | OCH$_3$ | CH$_3$ |
| 2-CH$_2$CH=CH$_2$ | OCH$_3$ | OCH$_3$ |
| 2-CH(CH$_3$)$_2$ | H | CH$_3$ |
| 2-CH(CH$_3$)$_2$ | Cl | CH$_3$ |
| 2-CH(CH$_3$)$_2$ | Br | CH$_3$ |
| 2-CH(CH$_3$)$_2$ | CH$_2$CH$_3$ | CH$_3$ |
| 2-CH(CH$_3$)$_2$ | OCH$_2$CH$_3$ | CH$_3$ |
| 2-CH(CH$_3$)$_2$ | OCH$_2$CH$_2$CH$_3$ | CH$_3$ |
| 2-CH(CH$_3$)$_2$ | CF$_3$ | CH$_3$ |
| 2-CH(CH$_3$)$_2$ | SCH$_3$ | CH$_3$ |
| 2-NO$_2$ | CH$_2$OCH$_3$ | CH$_3$ |
| 2-SO$_2$N(CH$_3$)$_2$ | CH$_2$OCH$_3$ | CH$_3$ |
| 2-NO$_2$ | CH$_2$OCH$_3$ | OCH$_3$ |
| 2-SO$_2$N(CH$_3$)$_2$ | CH$_2$OCH$_3$ | OCH$_3$ |
| 2-CH(CH$_3$)$_2$ | OCH$_2$CH=CH$_2$ | CH$_3$ |
| 2-CH$_3$(CH$_3$)$_2$ | OCH$_2$C≡CH | CH$_3$ |
| 2-NO$_2$ | OCH$_2$CH=CH$_2$ | CH$_3$ |
| 2-SO$_2$N(CH$_3$)$_2$ | OCH$_2$CH=CH$_2$ | CH$_3$ |
| 4-CH$_3$ | CH$_3$ | CH$_3$ |
| 4-CH$_3$ | OCH$_3$ | CH$_3$ |
| 4-CH$_3$ | OCH$_3$ | OCH$_3$ |
| 4-Cl | CH$_3$ | CH$_3$ |
| 4-Cl | OCH$_3$ | CH$_3$ |
| 4-Cl | OCH$_3$ | OCH$_3$ |
| 4-Br | CH$_3$ | CH$_3$ |
| 4-Br | OCH$_3$ | CH$_3$ |
| 4-Br | OCH$_3$ | OCH$_3$ |
| 4-NO$_2$ | CH$_3$ | CH$_3$ |
| 4-NO$_2$ | OCH$_3$ | CH$_3$ |
| 4-NO$_2$ | OCH$_3$ | OCH$_3$ |
| 4-SO$_2$N(CH$_3$)$_2$ | CH$_3$ | CH$_3$ |
| 4-SO$_2$N(CH$_3$)$_2$ | OCH$_3$ | CH$_3$ |
| 4-SO$_2$N(CH$_3$)$_2$ | OCH$_3$ | OCH$_3$ |
| 4-OCH$_3$ | CH$_3$ | CH$_3$ |
| 4-OCH$_3$ | OCH$_3$ | CH$_3$ |
| 4-OCH$_3$ | OCH$_3$ | OCH$_3$ |
| 4-CH$_2$CH$_3$ | CH$_3$ | CH$_3$ |
| 4-CH$_2$CH$_3$ | OCH$_3$ | CH$_3$ |
| 4-CH$_2$CH$_3$ | OCH$_3$ | OCH$_3$ |
| 4-CH(CH$_3$)$_2$ | CH$_3$ | CH$_3$ |
| 4-CH(CH$_3$)$_2$ | OCH$_3$ | CH$_3$ |
| 4-CH(CH$_3$)$_2$ | OCH$_3$ | OCH$_3$ |
| 4-CH$_2$CH(CH$_3$)$_2$ | CH$_3$ | CH$_3$ |
| 4-CH$_2$CH(CH$_3$)$_2$ | OCH$_3$ | CH$_3$ |
| 4-CH$_2$CH(CH$_3$)$_2$ | OCH$_3$ | OCH$_3$ |
| 4-SO$_2$N(CH$_3$)[CH(CH$_3$)$_2$] | CH$_3$ | CH$_3$ |
| 4-SO$_2$N(CH$_3$)[CH(CH$_3$)$_2$] | OCH$_3$ | CH$_3$ |
| 4-SO$_2$N(CH$_3$)[CH(CH$_3$)$_2$] | OCH$_3$ | OCH$_3$ |

TABLE II-continued structure: thiophene-R with SO2NHC(O)NH-pyrimidine(X,Y)

| R | X | Y |
|---|---|---|
| 4-SO2N(OCH3)CH3 | CH3 | CH3 |
| 4-SO2N(OCH3)CH3 | OCH3 | CH3 |
| 4-SO2N(OCH3)CH3 | OCH3 | OCH3 |
| 4-CH2CH=CH2 | CH3 | CH3 |
| 4-CH2CH=CH2 | OCH3 | CH3 |
| 4-CH2CH=CH2 | OCH3 | OCH3 |
| 4-CH3 | H | CH3 |
| 4-CH3 | Cl | CH3 |
| 4-CH3 | Br | CH3 |
| 4-CH3 | CH2CH3 | CH3 |
| 4-CH3 | OCH2CH3 | CH3 |
| 4-CH3 | OCH2CH2CH3 | CH3 |
| 4-CH3 | CF3 | CH3 |
| 4-CH3 | SCH3 | CH3 |
| 4-CH3 | CH2OCH3 | CH3 |
| 4-Cl | CH2OCH3 | CH3 |
| 4-Br | CH2OCH3 | CH3 |
| 4-NO2 | CH2OCH3 | CH3 |
| 4-SO2N(CH3)2 | CH2OCH3 | CH3 |
| 4-CH3 | CH2OCH3 | OCH3 |
| 4-Cl | CH2OCH3 | OCH3 |
| 4-Br | CH2OCH3 | OCH3 |
| 4-NO2 | CH2OCH3 | OCH3 |
| 4-SO2N(CH3)2 | CH2OCH3 | OCH3 |
| 4-CH3 | OCH2CH=CH2 | CH3 |
| 4-CH3 | OCH2C≡CH | CH3 |
| 4-NO2 | OCH2CH=CH2 | CH3 |
| 4-SO2N(CH3)2 | OCH2CH=CH2 | CH3 |
| 4-Cl | OCH2CH=CH2 | CH3 |
| 4-Br | OCH2CH=CH2 | CH3 |

TABLE II-a structure: thiophene-R with SO2N(R3)C(O)N(R4)-pyrimidine(X,Y)

| R | R3 | R4 | X | Y |
|---|---|---|---|---|
| 2-CH3 | H | CH3 | CH3 | CH3 |
| 2-CH3 | H | CH3 | OCH3 | CH3 |
| 2-CH3 | H | CH3 | OCH3 | OCH3 |
| 2-CH3 | CH3 | CH3 | CH3 | OCH3 |
| 2-Cl | H | CH3 | CH3 | CH3 |
| 2-Cl | H | CH3 | CH3 | OCH3 |
| 2-Cl | H | CH3 | OCH3 | OCH3 |
| 2-Cl | CH3 | CH3 | OCH3 | OCH3 |
| 2-Br | H | CH3 | CH3 | CH3 |
| 2-Br | H | CH3 | OCH3 | CH3 |
| 2-Br | H | CH3 | OCH3 | OCH3 |
| 2-Br | CH3 | CH3 | OCH3 | CH3 |
| 2-NO2 | H | CH3 | CH3 | CH3 |
| 2-NO2 | H | CH3 | OCH3 | CH3 |
| 2-NO2 | H | CH3 | OCH3 | OCH3 |
| 2-NO2 | CH3 | CH3 | OCH3 | CH3 |
| 2-SO2N(CH3)2 | H | CH3 | CH3 | CH3 |
| 2-SO2N(CH3)2 | H | CH3 | OCH3 | CH3 |
| 2-SO2N(CH3)2 | H | CH3 | OCH3 | OCH3 |
| 2-CH(CH3)2 | H | CH3 | CH3 | CH3 |
| 2-CH(CH3)2 | H | CH3 | OCH3 | CH3 |
| 2-CH(CH3)2 | H | CH3 | OCH3 | OCH3 |
| 2-(CH2)3CH3 | H | CH3 | CH3 | OCH3 |
| 2-(CH2)3CH3 | H | CH3 | OCH3 | OCH3 |
| 2-(CH2)3CH3 | CH3 | CH3 | OCH3 | OCH3 |

TABLE II-a-continued

| R | R3 | R4 | X | Y |
|---|---|---|---|---|
| 2-SO2N(CH3)(C2H5) | H | CH3 | CH3 | OCH3 |
| 2-SO2N(CH3)(C2H5) | H | CH3 | CH3 | CH3 |
| 2-SO2N(CH3)(C2H5) | H | CH3 | OCH3 | OCH3 |
| 2-SO2N(OCH3)CH3 | H | CH3 | CH3 | CH3 |
| 2-SO2N(OCH3)CH3 | H | CH3 | OCH3 | CH3 |
| 2-SO2N(OCH3)CH3 | H | CH3 | OCH3 | OCH3 |
| 2-CH3 | H | OCH3 | CH3 | CH3 |
| 2-CH3 | H | OCH3 | OCH3 | OCH3 |
| 2-CH3 | H | OCH3 | CH3 | OCH3 |
| 2-CH3 | CH3 | OCH3 | OCH3 | CH3 |
| 2-CH3 | H | OCH3 | Cl | CH3 |
| 2-CH3 | H | OCH3 | Br | CH3 |
| 2-CH3 | H | OCH3 | CH2CH3 | CH3 |
| 2-CH3 | H | OCH3 | OCH2CH3 | CH3 |
| 2-CH3 | H | OCH3 | OCH2CH2CH3 | CH3 |
| 2-CH3 | H | OCH3 | CF3 | CH3 |
| 2-CH3 | H | OCH3 | SCH3 | CH3 |
| 2-CH3 | H | OCH3 | CH2OCH3 | CH3 |
| 2-Cl | H | OCH3 | CH2OCH3 | OCH3 |
| 2-Br | H | OCH3 | CH2OCH3 | OCH3 |
| 2-NO2 | H | OCH3 | CH2OCH3 | OCH3 |
| 2-SO2N(CH3)2 | H | OCH3 | CH2OCH3 | OCH3 |
| 2-OCH3 | H | OCH3 | CH2OCH3 | OCH3 |
| 2-CH2CH=CH2 | H | CH3 | OCH3 | CH3 |
| 2-NO2 | H | CH3 | OCH2CH=CH2 | CH3 |
| 2-Br | H | CH3 | OCH2CH=CH2 | CH3 |
| 2-SO2N(CH3)2 | H | CH3 | OCH2C≡CH | CH3 |

TABLE III structure: thiophene-R with SO2NHCNH-pyrazine(X,Y)

| R | X | Y |
|---|---|---|
| 3-CH3 | CH3 | CH3 |
| 3-CH3 | OCH3 | CH3 |
| 3-CH3 | OCH3 | OCH3 |
| 3-Cl | CH3 | CH3 |
| 3-Cl | OCH3 | CH3 |
| 3-Cl | OCH3 | OCH3 |
| 3-Br | CH3 | CH3 |
| 3-Br | OCH3 | CH3 |
| 3-Br | OCH3 | OCH3 |
| 3-NO2 | CH3 | CH3 |
| 3-NO2 | OCH3 | CH3 |
| 3-NO2 | OCH3 | OCH3 |
| 3-SO2N(CH3)2 | CH3 | CH3 |

TABLE III-continued

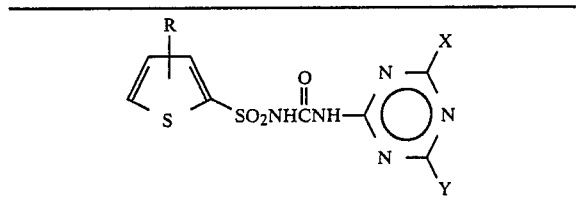

| R | X | Y |
|---|---|---|
| 3-SO2N(CH3)2 | OCH3 | CH3 |
| 3-SO2N(CH3)2 | OCH3 | OCH3 |
| 3-OCH3 | CH3 | CH3 |
| 3-OCH3 | OCH3 | CH3 |
| 3-OCH3 | OCH3 | OCH3 |
| 3-CH2CH3 | CH3 | CH3 |
| 3-CH2CH3 | OCH3 | CH3 |
| 3-CH2CH3 | OCH3 | OCH3 |
| 3-CH(CH3)2 | CH3 | CH3 |
| 3-CH(CH3)2 | OCH3 | CH3 |
| 3-CH(CH3)2 | OCH3 | OCH3 |
| 3-CH2CH(CH3)2 | CH3 | CH3 |
| 3-CH2CH(CH3)2 | OCH3 | CH3 |
| 3-CH2CH(CH3)2 | OCH3 | OCH3 |
| 3-SO2N(CH3)[CH(CH3)2] | CH3 | CH3 |
| 3-SO2N(CH3)[CH(CH3)2] | OCH3 | CH3 |
| 3-SO2N(CH3)[CH(CH3)2] | OCH3 | OCH3 |
| 3-SO2N(OCH3)CH3 | CH3 | CH3 |
| 3-SO2N(OCH3)CH3 | OCH3 | CH3 |
| 3-SO2N(OCH3)CH3 | OCH3 | OCH3 |
| 3-CH2CH=CH2 | CH3 | CH3 |
| 3-CH2CH=CH2 | OCH3 | CH3 |
| 3-CH2CH=CH2 | OCH3 | OCH3 |
| 3-CH3 | H | CH3 |
| 3-CH3 | Cl | CH3 |
| 3-CH3 | Br | CH3 |
| 3-CH3 | CH2CH3 | CH3 |
| 3-CH3 | OCH2CH3 | CH3 |
| 3-CH3 | OCH2CH2CH3 | CH3 |
| 3-CH3 | CF3 | CH3 |
| 3-CH3 | SCH3 | CH3 |
| 3-CH3 | CH2OCH3 | CH3 |
| 3-Cl | CH2OCH3 | CH3 |
| 3-Br | CH2OCH3 | CH3 |
| 3-NO2 | CH2OCH3 | CH3 |
| 3-SO2N(CH3)2 | CH2OCH3 | CH3 |
| 3-CH3 | CH2OCH3 | OCH3 |
| 3-Cl | CH2OCH3 | OCH3 |
| 3-Br | CH2OCH3 | OCH3 |
| 3-NO2 | CH2OCH3 | OCH3 |
| 3-SO2N(CH3)2 | CH2OCH3 | OCH3 |
| 3-CH3 | OCH2CH=CH2 | CH3 |
| 3-CH3 | OCH2C≡CH | CH3 |
| 3-NO2 | OCH2CH=CH2 | CH3 |
| 3-SO2N(CH3)2 | OCH2CH=CH2 | CH3 |
| 3-Cl | OCH2CH=CH2 | CH3 |
| 3-Br | OCH2CH=CH2 | CH3 |
| 4-CH3 | CH3 | CH3 |
| 4-CH3 | OCH3 | CH3 |
| 4-CH3 | OCH3 | OCH3 |
| 4-Cl | CH3 | CH3 |
| 4-Cl | OCH3 | CH3 |
| 4-Cl | OCH3 | OCH3 |
| 4-Br | CH3 | CH3 |
| 4-Br | OCH3 | CH3 |
| 4-Br | OCH3 | OCH3 |
| 4-NO2 | CH3 | CH3 |
| 4-NO2 | OCH3 | CH3 |
| 4-NO2 | OCH3 | OCH3 |
| 4-SO2N(CH3)2 | CH3 | CH3 |
| 4-SO2N(CH3)2 | OCH3 | CH3 |
| 4-SO2N(CH3)2 | OCH3 | OCH3 |
| 4-OCH3 | CH3 | CH3 |
| 4-OCH3 | OCH3 | CH3 |
| 4-OCH3 | OCH3 | OCH3 |
| 4-CH2CH3 | CH3 | CH3 |
| 4-CH2CH3 | OCH3 | CH3 |
| 4-CH2CH3 | OCH3 | OCH3 |
| 4-CH(CH3)2 | CH3 | CH3 |
| 4-CH(CH3)2 | OCH3 | CH3 |
| 4-CH(CH3)2 | OCH3 | OCH3 |

TABLE III-continued

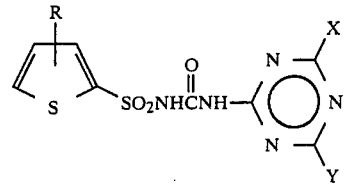

| R | X | Y |
|---|---|---|
| 4-CH2CH(CH3)2 | CH3 | CH3 |
| 4-CH2CH(CH3)2 | OCH3 | CH3 |
| 4-CH2CH(CH3)2 | OCH3 | OCH3 |
| 4-SO2N(CH3)[CH(CH3)2] | CH3 | CH3 |
| 4-SO2N(CH3)[CH(CH3)2] | OCH3 | CH3 |
| 4-SO2N(CH3)[CH(CH3)2] | OCH3 | OCH3 |
| 4-SO2N(OCH3)CH3 | CH3 | CH3 |
| 4-SO2N(OCH3)CH3 | OCH3 | CH3 |
| 4-SO2N(OCH3)CH3 | OCH3 | OCH3 |
| 4-CH2CH=CH2 | CH3 | CH3 |
| 4-CH2CH=CH2 | OCH3 | CH3 |
| 4-CH2CH=CH2 | OCH3 | OCH3 |
| 4-CH3 | H | CH3 |
| 4-CH3 | Cl | CH3 |
| 4-CH3 | Br | CH3 |
| 4-CH3 | CH2CH3 | CH3 |
| 4-CH3 | OCH2CH3 | CH3 |
| 4-CH3 | OCH2CH2CH3 | CH3 |
| 4-CH3 | CF3 | CH3 |
| 4-CH3 | SCH3 | CH3 |
| 4-CH3 | CH2OCH3 | CH3 |
| 4-Cl | CH2OCH3 | CH3 |
| 4-Br | CH2OCH3 | CH3 |
| 4-NO2 | CH2OCH3 | CH3 |
| 4-SO2N(CH3)2 | CH2OCH3 | CH3 |
| 4-CH3 | CH2OCH3 | OCH3 |
| 4-Cl | CH2OCH3 | OCH3 |
| 4-Br | CH2OCH3 | OCH3 |
| 4-NO2 | CH2OCH3 | OCH3 |
| 4-SO2N(CH3)2 | CH2OCH3 | OCH3 |
| 4-CH3 | OCH2CH=CH2 | CH3 |
| 4-CH3 | OCH2C≡CH | CH3 |
| 4-NO2 | OCH2CH=CH2 | CH3 |
| 4-SO2N(CH3)2 | OCH2CH=CH2 | CH3 |
| 4-Cl | OCH2CH=CH2 | CH3 |
| 4-Br | OCH2CH=CH2 | CH3 |

TABLE III-a

| R | R3 | R4 | X | Y |
|---|---|---|---|---|
| 3-CH3 | H | CH3 | CH3 | CH3 |
| 3-CH3 | H | CH3 | OCH3 | CH3 |
| 3-CH3 | H | CH3 | OCH3 | OCH3 |
| 3-CH3 | CH3 | CH3 | CH3 | OCH3 |
| 3-Cl | H | CH3 | CH3 | CH3 |
| 3-Cl | H | CH3 | CH3 | OCH3 |
| 3-Cl | H | CH3 | OCH3 | OCH3 |
| 3-Cl | CH3 | CH3 | OCH3 | OCH3 |
| 3-Br | H | CH3 | CH3 | CH3 |
| 3-Br | H | CH3 | OCH3 | CH3 |
| 3-Br | H | CH3 | OCH3 | OCH3 |
| 3-Br | CH3 | CH3 | OCH3 | OCH3 |
| 3-NO2 | H | CH3 | CH3 | CH3 |
| 3-NO2 | H | CH3 | OCH3 | CH3 |
| 3-NO2 | H | CH3 | OCH3 | OCH3 |
| 3-NO2 | CH3 | CH3 | OCH3 | OCH3 |
| 3-SO2N(CH3)2 | H | CH3 | OCH3 | OCH3 |
| 3-SO2N(CH3)2 | H | CH3 | OCH3 | CH3 |
| 3-SO2N(CH3)2 | CH3 | CH3 | OCH3 | OCH3 |
| 3-CH(CH3)2 | H | CH3 | CH3 | CH3 |

TABLE III-a-continued

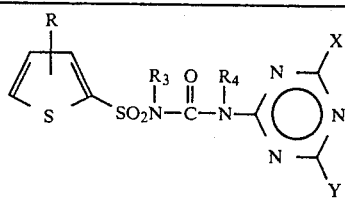

| R | R₃ | R₄ | X | Y |
|---|---|---|---|---|
| 3-CH(CH₃)₂ | H | CH₃ | OCH₃ | CH₃ |
| 3-CH(CH₃)₂ | H | CH₃ | OCH₃ | OCH₃ |
| 3-(CH₂)₃CH₃ | H | CH₃ | CH₃ | OCH₃ |
| 3-(CH₂)₃CH₃ | H | CH₃ | OCH₃ | OCH₃ |
| 3-(CH₂)₃CH₃ | CH₃ | CH₃ | OCH₃ | OCH₃ |
| 3-SO₂N(CH₃)(C₂H₅) | H | CH₃ | CH₃ | OCH₃ |
| 3-SO₂N(CH₃)(C₂H₅) | H | CH₃ | CH₃ | CH₃ |
| 3-SO₂N(CH₃)(C₂H₅) | H | CH₃ | OCH₃ | OCH₃ |
| 3-SO₂N(OCH₃)CH₃ | H | CH₃ | CH₃ | CH₃ |
| 3-SO₂N(OCH₃)CH₃ | H | CH₃ | OCH₃ | CH₃ |
| 3-SO₂N(OCH₃)CH₃ | H | C₃ | OCH₃ | OCH₃ |
| 3-CH₃ | H | OCH₃ | CH₃ | CH₃ |
| 3-CH₃ | H | OCH₃ | OCH₃ | CH₃ |
| 3-CH₃ | H | OCH₃ | CH₃ | OCH₃ |
| 3-CH₃ | CH₃ | OCH₃ | OCH₃ | CH₃ |
| 3-CH₃ | H | OCH₃ | Cl | CH₃ |
| 3-CH₃ | H | OCH₃ | Br | CH₃ |
| 3-CH₃ | H | OCH₃ | CH₂CH₃ | CH₃ |
| 3-CH₃ | H | OCH₃ | OCH₂CH₃ | CH₃ |
| 3-CH₃ | H | OCH₃ | OCH₂CH₂CH₃ | CH₃ |
| 3-CH₃ | H | OCH₃ | CF₃ | CH₃ |
| 3-CH₃ | H | OCH₃ | SCH₃ | CH₃ |
| 3-CH₃ | H | OCH₃ | CH₂OCH₃ | CH₃ |
| 3-Cl | H | OCH₃ | CH₂OCH₃ | OCH₃ |
| 3-Br | H | OCH₃ | CH₂OCH₃ | OCH₃ |
| 3-NO₂ | H | OCH₃ | CH₂OCH₃ | OCH₃ |
| 3-SO₂N(CH₃)₂ | H | OCH₃ | CH₂OCH₃ | OCH₃ |
| 3-OCH₃ | H | OCH₃ | CH₂OCH₃ | OCH₃ |
| 3-CH₂CH=CH₂ | H | CH₃ | OCH₃ | CH₃ |
| 3-NO₂ | H | CH₃ | OCH₂CH=CH₂ | CH₃ |
| 3-Br | H | CH₃ | OCH₂CH=CH₂ | CH₃ |
| 3-SO₂N(CH₃)₂ | H | CH₃ | OCH₂C≡CH | CH₃ |
| 4-CH₃ | H | CH₃ | CH₃ | CH₃ |
| 4-CH₃ | H | CH₃ | OCH₃ | CH₃ |
| 4-CH₃ | H | CH₃ | OCH₃ | OCH₃ |
| 4-CH₃ | CH₃ | CH₃ | CH₃ | OCH₃ |
| 4-Cl | H | CH₃ | CH₃ | CH₃ |
| 4-Cl | H | CH₃ | CH₃ | OCH₃ |
| 4-Cl | H | CH₃ | OCH₃ | OCH₃ |
| 4-Br | H | CH₃ | CH₃ | CH₃ |
| 4-Br | H | CH₃ | OCH₃ | CH₃ |
| 4-Br | H | CH₃ | OCH₃ | OCH₃ |
| 4-Br | CH₃ | CH₃ | OCH₃ | OCH₃ |
| 4-NO₂ | H | CH₃ | CH₃ | CH₃ |
| 4-NO₂ | H | CH₃ | OCH₃ | CH₃ |
| 4-NO₂ | H | CH₃ | OCH₃ | OCH₃ |
| 4-NO₂ | CH₃ | CH₃ | OCH₃ | OCH₃ |
| 4-SO₂N(CH₃)₂ | H | CH₃ | CH₃ | CH₃ |
| 4-SO₂N(CH₃)₂ | H | CH₃ | OCH₃ | CH₃ |
| 4-SO₂N(CH₃)₂ | CH₃ | CH₃ | OCH₃ | CH₃ |
| 4-CH(CH₃)₂ | H | CH₃ | CH₃ | CH₃ |
| 4-CH(CH₃)₂ | H | CH₃ | OCH₃ | CH₃ |
| 4-CH(CH₃)₂ | H | CH₃ | OCH₃ | OCH₃ |
| 4-(CH₂)₃CH₃ | H | CH₃ | CH₃ | OCH₃ |
| 4-(CH₂)₃CH₃ | H | CH₃ | OCH₃ | OCH₃ |
| 4-(CH₂)₃CH₃ | CH₃ | CH₃ | OCH₃ | OCH₃ |

TABLE III-a-continued

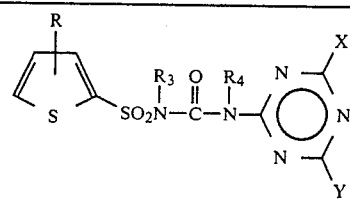

| R | R₃ | R₄ | X | Y |
|---|---|---|---|---|
| 4-SO₂N(CH₃)(C₂H₅) | H | CH₃ | CH₃ | OCH₃ |
| 4-SO₂N(CH₃)(C₂H₅) | H | CH₃ | CH₃ | CH₃ |
| 4-SO₂N(CH₃)(C₂H₅) | H | CH₃ | OCH₃ | OCH₃ |
| 4-SO₂N(OCH₃)CH₃ | H | CH₃ | CH₃ | CH₃ |
| 4-SO₂N(OCH₃)CH₃ | H | CH₃ | OCH₃ | CH₃ |
| 4-SO₂N(OCH₃)CH₃ | H | CH₃ | OCH₃ | OCH₃ |
| 4-CH₃ | H | OCH₃ | CH₃ | CH₃ |
| 4-CH₃ | H | OCH₃ | OCH₃ | OCH₃ |
| 4-CH₃ | H | OCH₃ | CH₃ | OCH₃ |
| 4-CH₃ | CH₃ | OCH₃ | OCH₃ | CH₃ |
| 4-CH₃ | H | OCH₃ | Cl | CH₃ |
| 4-CH₃ | H | OCH₃ | Br | CH₃ |
| 4-CH₃ | H | OCH₃ | CH₂CH₃ | CH₃ |
| 4-CH₃ | H | OCH₃ | OCH₂CH₃ | CH₃ |
| 4-CH₃ | H | OCH₃ | OCH₂CH₂CH₃ | CH₃ |
| 4-CH₃ | H | OCH₃ | CF₃ | CH₃ |
| 4-CH₃ | H | OCH₃ | SCH₃ | CH₃ |
| 4-CH₃ | H | OCH₃ | CH₂OCH₃ | CH₃ |
| 4-Cl | H | OCH₃ | CH₂OCH₃ | OCH₃ |
| 4-Br | H | OCH₃ | CH₂OCH₃ | OCH₃ |
| 4-NO₂ | H | OCH₃ | CH₂OCH₃ | OCH₃ |
| 4-SO₂N(CH₃)₂ | H | OCH₃ | CH₂OCH₃ | OCH₃ |
| 4-OCH₃ | H | OCH₃ | CH₂OCH₃ | OCH₃ |
| 4-CH₂CH=CH₂ | H | CH₃ | OCH₃ | CH₃ |
| 4-NO₂ | H | CH₃ | OCH₂CH=CH₂ | CH₃ |
| 4-Br | H | CH₃ | OCH₂CH=CH₂ | CH₃ |
| 4-SO₂N(CH₃)₂ | H | CH₃ | OCH₂C≡CH | CH₃ |

TABLE IV

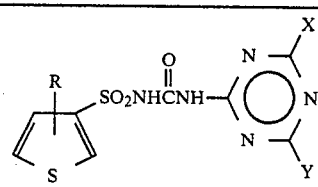

| R | X | Y |
|---|---|---|
| 2-NO₂ | CH₃ | CH₃ |
| 2-NO₂ | OCH₃ | CH₃ |
| 2-NO₂ | OCH₃ | OCH₃ |
| 2-SO₂N(CH₃)₂ | CH₃ | CH₃ |
| 2-SO₂N(CH₃)₂ | OCH₃ | CH₃ |
| 2-SO₂N(CH₃)₂ | OCH₃ | OCH₃ |
| 2-OCH₃ | CH₃ | CH₃ |
| 2-OCH₃ | OCH₃ | CH₃ |
| 2-OCH₃ | OCH₃ | OCH₃ |
| 2-CH₂CH₃ | CH₃ | CH₃ |
| 2-CH₂CH₃ | OCH₃ | CH₃ |
| 2-CH₂CH₃ | OCH₃ | OCH₃ |
| 2-CH(CH₃)₂ | CH₃ | CH₃ |
| 2-CH(CH₃)₂ | OCH₃ | CH₃ |

TABLE IV-continued

[Structure: thiophene with R substituent, SO2NHCNH-C(=O)-pyrimidine with X and Y substituents]

| R | X | Y |
|---|---|---|
| 2-CH(CH₃)₂ | OCH₃ | OCH₃ |
| 2-CH₂CH(CH₃)₂ | CH₃ | CH₃ |
| 2-CH₂CH(CH₃)₂ | OCH₃ | CH₃ |
| 2-CH₂CH(CH₃)₂ | OCH₃ | OCH₃ |
| 2-SO₂N(CH₃)[CH(CH₃)₂] | CH₃ | CH₃ |
| 2-SO₂N(CH₃)[CH(CH₃)₂] | OCH₃ | CH₃ |
| 2-SO₂N(CH₃)[CH(CH₃)₂] | OCH₃ | OCH₃ |
| 2-SO₂N(OCH₃)CH₃ | CH₃ | CH₃ |
| 2-SO₂N(OCH₃)CH₃ | OCH₃ | CH₃ |
| 2-SO₂N(OCH₃)CH₃ | OCH₃ | OCH₃ |
| 2-CH₂CH=CH₂ | CH₃ | CH₃ |
| 2-CH₂CH=CH₂ | OCH₃ | CH₃ |
| 2-CH₂CH=CH₂ | OCH₃ | OCH₃ |
| 2-CH(CH₃)₂ | H | CH₃ |
| 2-CH(CH₃)₂ | Cl | CH₃ |
| 2-CH(CH₃)₂ | Br | CH₃ |
| 2-CH(CH₃)₂ | CH₂CH₃ | CH₃ |
| 2-CH(CH₃)₂ | OCH₂CH₃ | CH₃ |
| 2-CH(CH₃)₂ | OCH₂CH₂CH₃ | CH₃ |
| 2-CH(CH₃)₂ | CF₃ | CH₃ |
| 2-CH(CH₃)₂ | SCH₃ | CH₃ |
| 2-NO₂ | CH₂OCH₃ | CH₃ |
| 2-SO₂N(CH₃)₂ | CH₂OCH₃ | CH₃ |
| 2-NO₂ | CH₂OCH₃ | OCH₃ |
| 2-SO₂N(CH₃)₂ | CH₂OCH₃ | OCH₃ |
| 2-NO₂ | OCH₂CH=CH₂ | CH₃ |
| 2-SO₂N(CH₃)₂ | OCH₂CH=CH₂ | CH₃ |
| 4-CH₃ | CH₃ | CH₃ |
| 4-CH₃ | OCH₃ | CH₃ |
| 4-CH₃ | OCH₃ | OCH₃ |
| 4-Cl | CH₃ | CH₃ |
| 4-Cl | OCH₃ | CH₃ |
| 4-Cl | OCH₃ | OCH₃ |
| 4-Br | CH₃ | CH₃ |
| 4-Br | OCH₃ | CH₃ |
| 4-Br | OCH₃ | OCH₃ |
| 4-NO₂ | CH₃ | CH₃ |
| 4-NO₂ | OCH₃ | CH₃ |
| 4-NO₂ | OCH₃ | OCH₃ |
| 4-SO₂N(CH₃)₂ | CH₃ | CH₃ |
| 4-SO₂N(CH₃)₂ | OCH₃ | CH₃ |
| 4-SO₂N(CH₃)₂ | OCH₃ | OCH₃ |
| 4-OCH₃ | CH₃ | CH₃ |
| 4-OCH₃ | OCH₃ | CH₃ |
| 4-OCH₃ | OCH₃ | OCH₃ |
| 4-CH₂CH₃ | CH₃ | CH₃ |
| 4-CH₂CH₃ | OCH₃ | CH₃ |
| 4-CH₂CH₃ | OCH₃ | OCH₃ |
| 4-CH(CH₃)₂ | CH₃ | CH₃ |
| 4-CH(CH₃)₂ | OCH₃ | CH₃ |
| 4-CH(CH₃)₂ | OCH₃ | OCH₃ |
| 4-CH₂CH(CH₃)₂ | CH₃ | CH₃ |
| 4-CH₂CH(CH₃)₂ | OCH₃ | CH₃ |
| 4-CH₂CH(CH₃)₂ | OCH₃ | OCH₃ |
| 4-SO₂N(CH₃)[CH(CH₃)₂] | CH₃ | CH₃ |
| 4-SO₂N(CH₃)[CH(CH₃)₂] | OCH₃ | CH₃ |
| 4-SO₂N(CH₃)[CH(CH₃)₂] | OCH₃ | OCH₃ |
| 4-SO₂N(OCH₃)CH₃ | CH₃ | CH₃ |
| 4-SO₂N(OCH₃)CH₃ | OCH₃ | CH₃ |
| 4-SO₂N(OCH₃)CH₃ | OCH₃ | OCH₃ |
| 4-CH₂CH=CH₂ | CH₃ | CH₃ |
| 4-CH₂CH=CH₂ | OCH₃ | CH₃ |
| 4-CH₂CH=CH₂ | OCH₃ | OCH₃ |
| 4-CH₃ | H | CH₃ |
| 4-CH₃ | Cl | CH₃ |
| 4-CH₃ | Br | CH₃ |
| 4-CH₃ | CH₂CH₃ | CH₃ |
| 4-CH₃ | OCH₂CH₃ | CH₃ |
| 4-CH₃ | OCH₂CH₂CH₃ | CH₃ |
| 4-CH₃ | CF₃ | CH₃ |
| 4-CH₃ | SCH₃ | CH₃ |
| 4-CH₃ | CH₂OCH₃ | CH₃ |
| 4-Cl | CH₂OCH₃ | CH₃ |
| 4-Br | CH₂OCH₃ | CH₃ |
| 4-NO₂ | CH₂OCH₃ | CH₃ |
| 4-SO₂N(CH₃)₂ | CH₂OCH₃ | CH₃ |
| 4-CH₃ | CH₂OCH₃ | OCH₃ |
| 4-Cl | CH₂OCH₃ | OCH₃ |
| 4-Br | CH₂OCH₃ | OCH₃ |
| 4-NO₂ | CH₂OCH₃ | OCH₃ |
| 4-SO₂N(CH₃)₂ | CH₂OCH₃ | OCH₃ |
| 4-CH₃ | OCH₂CH=CH₂ | CH₃ |
| 4-CH₃ | OCH₂C≡CH | CH₃ |
| 4-NO₂ | OCH₂CH=CH₂ | CH₃ |
| 4-SO₂N(CH₃)₂ | OCH₂CH=CH₂ | CH₃ |
| 4-Cl | OCH₂CH=CH₂ | CH₃ |
| 4-Br | OCH₂CH=CH₂ | CH₃ |

TABLE IV-a

[Structure: thiophene with R substituent, SO₂N(R₃)-C(=O)-N(R₄)-pyrimidine with X and Y]

| R | R₃ | R₄ | X | Y |
|---|---|---|---|---|
| 2-CH₃ | H | CH₃ | CH₃ | CH₃ |
| 2-CH₃ | H | CH₃ | OCH₃ | CH₃ |
| 2-CH₃ | H | CH₃ | OCH₃ | OCH₃ |
| 2-CH₃ | CH₃ | CH₃ | CH₃ | OCH₃ |
| 2-Cl | H | CH₃ | CH₃ | CH₃ |
| 2-Cl | H | CH₃ | OCH₃ | CH₃ |
| 2-Cl | H | CH₃ | OCH₃ | OCH₃ |
| 2-Br | H | CH₃ | CH₃ | CH₃ |
| 2-Br | H | CH₃ | OCH₃ | CH₃ |
| 2-Br | H | CH₃ | OCH₃ | OCH₃ |
| 2-Br | CH₃ | CH₃ | OCH₃ | CH₃ |
| 2-NO₂ | H | CH₃ | CH₃ | CH₃ |
| 2-NO₂ | H | CH₃ | OCH₃ | CH₃ |
| 2-NO₂ | H | CH₃ | OCH₃ | OCH₃ |
| 2-NO₂ | CH₃ | CH₃ | CH₃ | CH₃ |
| 2-SO₂N(CH₃)₂ | H | CH₃ | CH₃ | CH₃ |
| 2-SO₂N(CH₃)₂ | H | CH₃ | OCH₃ | CH₃ |
| 2-SO₂N(CH₃)₂ | H | CH₃ | OCH₃ | OCH₃ |
| 2-CH(CH₃)₂ | H | CH₃ | CH₃ | CH₃ |
| 2-CH(CH₃)₂ | H | CH₃ | OCH₃ | CH₃ |
| 2-CH(CH₃)₂ | H | CH₃ | OCH₃ | OCH₃ |
| 2-(CH₂)₃CH₃ | H | CH₃ | CH₃ | CH₃ |
| 2-(CH₂)₃CH₃ | H | CH₃ | OCH₃ | OCH₃ |
| 2-(CH₂)₃CH₃ | CH₃ | CH₃ | OCH₃ | OCH₃ |
| 2-SO₂N(CH₃)(C₂H₅) | H | CH₃ | CH₃ | OCH₃ |
| 2-SO₂N(CH₃)(C₂H₅) | H | CH₃ | CH₃ | CH₃ |
| 2-SO₂N(CH₃)(C₂H₅) | H | CH₃ | OCH₃ | OCH₃ |

TABLE IV-a-continued

Structure: thiophene-R with SO2N(R3)-C(O)-N(R4)-pyrimidine(X,Y)

| R | R3 | R4 | X | Y |
|---|---|---|---|---|
| 2-SO2N(OCH3)CH3 | H | CH3 | CH3 | CH3 |
| 2-SO2N(OCH3)CH3 | H | CH3 | OCH3 | CH3 |
| 2-SO2N(OCH3)CH3 | H | CH3 | OCH3 | OCH3 |
| 2-CH3 | H | OCH3 | CH3 | CH3 |
| 2-CH3 | H | OCH3 | OCH3 | OCH3 |
| 2-CH3 | H | OCH3 | CH3 | OCH3 |
| 2-CH3 | CH3 | OCH3 | OCH3 | CH3 |
| 2-CH3 | H | OCH3 | Cl | CH3 |
| 2-CH3 | H | OCH3 | Br | CH3 |
| 2-CH3 | H | OCH3 | CH2CH3 | CH3 |
| 2-CH3 | H | OCH3 | OCH2CH3 | CH3 |
| 2-CH3 | H | OCH3 | OCH2CH2CH3 | CH3 |
| 2-CH3 | H | OCH3 | CF3 | CH3 |
| 2-CH3 | H | OCH3 | SCH3 | CH3 |
| 2-CH3 | H | OCH3 | CH2OCH3 | CH3 |
| 2-Cl | H | OCH3 | CH2OCH3 | OCH3 |
| 2-Br | H | OCH3 | CH2OCH3 | OCH3 |
| 2-NO2 | H | OCH3 | CH2OCH3 | OCH3 |
| 2-SO2N(CH3)2 | H | OCH3 | CH2OCH3 | OCH3 |
| 2-OCH3 | H | OCH3 | CH2OCH3 | OCH3 |
| 2-CH2CH=CH2 | H | CH3 | OCH3 | CH3 |
| 2-NO2 | H | CH3 | OCH2CH=CH2 | CH3 |
| 2-Br | H | CH3 | OCH2CH=CH2 | CH3 |
| 2-SO2N(CH3)2 | H | CH3 | OCH2C≡CH | CH3 |
| 4-CH3 | H | CH3 | CH3 | CH3 |
| 4-CH3 | H | CH3 | OCH3 | CH3 |
| 4-CH3 | H | CH3 | OCH3 | OCH3 |
| 4-CH3 | CH3 | CH3 | CH3 | OCH3 |
| 4-Cl | H | CH3 | CH3 | CH3 |
| 4-Cl | H | CH3 | CH3 | OCH3 |
| 4-Cl | H | CH3 | OCH3 | OCH3 |
| 4-Br | H | CH3 | CH3 | CH3 |
| 4-Br | H | CH3 | OCH3 | CH3 |
| 4-Br | H | CH3 | OCH3 | OCH3 |
| 4-Br | CH3 | CH3 | OCH3 | CH3 |
| 4-NO2 | H | CH3 | CH3 | CH3 |
| 4-NO2 | H | CH3 | OCH3 | CH3 |
| 4-NO2 | H | CH3 | OCH3 | OCH3 |
| 4-NO2 | CH3 | CH3 | OCH3 | CH3 |
| 4-SO2N(CH3)2 | H | CH3 | CH3 | CH3 |
| 4-SO2N(CH3)2 | H | CH3 | OCH3 | CH3 |
| 4-SO2N(CH3)2 | H | CH3 | OCH3 | OCH3 |
| 4-CH(CH3)2 | H | CH3 | CH3 | CH3 |
| 4-CH(CH3)2 | H | CH3 | OCH3 | CH3 |
| 4-CH(CH3)2 | H | CH3 | OCH3 | OCH3 |
| 4-(CH2)3CH3 | H | CH3 | CH3 | OCH3 |
| 4-(CH2)3CH3 | H | CH3 | OCH3 | OCH3 |
| 4-(CH2)3CH3 | CH3 | CH3 | OCH3 | OCH3 |
| 4-SO2N(CH3)(C2H5) | H | CH3 | CH3 | OCH3 |
| 4-SO2N(CH3)(C2H5) | H | CH3 | CH3 | CH3 |
| 4-SO2N(CH3)(C2H5) | H | CH3 | OCH3 | OCH3 |
| 4-SO2N(OCH3)CH3 | H | CH3 | CH3 | CH3 |
| 4-SO2N(OCH3)CH3 | H | CH3 | OCH3 | CH3 |
| 4-SO2N(OCH3)CH3 | H | CH3 | OCH3 | OCH3 |
| 4-CH3 | H | OCH3 | CH3 | CH3 |
| 4-CH3 | H | OCH3 | OCH3 | OCH3 |
| 4-CH3 | H | OCH3 | CH3 | OCH3 |
| 4-CH3 | CH3 | OCH3 | OCH3 | CH3 |
| 4-CH3 | H | OCH3 | Cl | CH3 |
| 4-CH3 | H | OCH3 | Br | CH3 |
| 4-CH3 | H | OCH3 | CH2CH3 | CH3 |
| 4-CH3 | H | OCH3 | OCH2CH3 | CH3 |
| 4-CH3 | H | OCH3 | OCH2CH2CH3 | CH3 |
| 4-CH3 | H | OCH3 | CF3 | CH3 |
| 4-CH3 | H | OCH3 | SCH3 | CH3 |
| 4-CH3 | H | OCH3 | CH2OCH3 | CH3 |
| 4-Cl | H | OCH3 | CH2OCH3 | OCH3 |
| 4-Br | H | OCH3 | CH2OCH3 | OCH3 |
| 4-NO2 | H | OCH3 | CH2OCH3 | OCH3 |
| 4-SO2N(CH3)2 | H | OCH3 | CH2OCH3 | OCH3 |
| 4-OCH3 | H | OCH3 | CH2OCH3 | OCH3 |
| 4-CH2CH=CH2 | H | CH3 | OCH3 | CH3 |
| 4-NO2 | H | CH3 | OCH2CH=CH2 | CH3 |
| 4-Br | H | CH3 | OCH2CH=CH2 | CH3 |
| 4-SO2N(CH3)2 | H | CH3 | OCH2C≡CH | CH3 |

TABLE V

Structure: 3-substituted thiophene with SO2-N(R3)-C(O)-N(R4)-pyrimidine(X,Y,Z)

| R | R3 | R4 | X | Y | Z |
|---|---|---|---|---|---|
| 3-NO2 | H | H | CH3 | CH3 | C—Cl |
| 3-CH3 | H | H | CH3 | CH3 | C—Cl |
| 3-Cl | H | H | CH3 | CH3 | C—Cl |
| 3-NO2 | H | H | CH3 | CH3 | C—Br |
| 3-CH3 | H | H | CH3 | CH3 | C—Br |
| 3-Cl | H | H | CH3 | CH3 | C—Br |
| 3-NO2 | H | H | CH3 | CH3 | C—CN |
| 3-CH3 | H | H | CH3 | CH3 | C—CN |
| 3-Cl | H | H | CH3 | CH3 | C—CN |
| 3-NO2 | H | H | CH3 | CH3 | C—CH3 |

TABLE V-continued

| R | $R_3$ | $R_4$ | X | Y | Z |
|---|---|---|---|---|---|
| 3-CH$_3$ | H | H | CH$_3$ | CH$_3$ | C—CH$_3$ |
| 3-Cl | H | H | CH$_3$ | CH$_3$ | C—CH$_3$ |
| 3-NO$_2$ | H | H | CH$_3$ | CH$_3$ | C—CH$_2$CH$_3$ |
| 3-CH$_3$ | H | H | CH$_3$ | CH$_3$ | C—CH$_2$CH$_3$ |
| 3-Cl | H | H | CH$_3$ | CH$_3$ | C—CH$_2$CH$_3$ |
| 3-CH$_3$ | H | H | CH$_3$ | CH$_3$ | C—CH$_2$CH$_2$Cl |
| 3-Cl | H | H | CH$_3$ | CH$_3$ | C—CH$_2$CH$_2$Cl |
| 3-CH$_3$ | H | H | CH$_3$ | CH$_3$ | C—CH$_2$CH=CH$_2$ |
| 3-Cl | H | H | CH$_3$ | CH$_3$ | C—CH$_2$CH=CH$_2$ |
| 3-CH$_3$ | H | H | H | CH$_3$ | CCH$_3$ |
| 3-CH$_3$ | H | H | H | OCH$_3$ | CCH$_3$ |
| 3-CH$_3$ | H | H | H | CH$_3$ | CCl |
| 3-Br | H | H | H | CH$_3$ | CBr |
| 3-CH$_3$ | H | H | H | CH$_3$ | CCN |
| 3-CH$_3$ | H | H | H | CH$_3$ | CBr |
| 3-SO$_2$N(CH$_3$)$_2$ | H | H | CH$_3$ | CH$_3$ | CCl |
| 3-SO$_2$N(CH$_3$)$_2$ | H | H | CH$_3$ | CH$_3$ | CBr |
| 3-SO$_2$N(CH$_3$)$_2$ | H | H | CH$_3$ | CH$_3$ | CCN |
| 3-SO$_2$N(CH$_3$)$_2$ | H | H | CH$_3$ | CH$_3$ | CCH$_3$ |
| 3-SO$_2$N(CH$_3$)$_2$ | H | H | CH$_3$ | CH$_3$ | CCH$_2$CH$_3$ |
| 3-SO$_2$N(CH$_3$)$_2$ | H | H | CH$_3$ | CH$_3$ | CCH$_2$CH$_2$Cl |
| 3-SO$_2$N(CH$_3$)$_2$ | H | H | OCH$_3$ | OCH$_3$ | CCH$_3$ |
| 3-SO$_2$N(CH$_3$)(CH(CH$_3$)$_2$) | H | H | OCH$_3$ | CH$_3$ | CBr |
| 3-SO$_2$N(CH$_3$)(CH(CH$_3$)$_2$) | H | H | CH$_3$ | CH$_3$ | CCl |
| 3-SO$_2$N(CH$_3$)(CH(CH$_3$)$_2$) | H | H | CH$_3$ | CH$_3$ | CCH$_2$CH$_2$Cl |
| 3-SO$_2$N(CH$_3$)(CH(CH$_3$)$_2$) | H | H | CH$_3$ | CH$_3$ | CCH$_2$CH$_3$ |
| 3-NO$_2$ | H | H | OCH$_2$CH=CH$_2$ | CH$_3$ | CCH$_3$ |
| 3-NO$_2$ | H | H | OCH$_3$ | CH$_3$ | CCl |
| 3-NO$_2$ | H | H | CH$_3$ | CH$_3$ | CCl |
| 3-OCH$_3$ | H | H | OCH$_3$ | CH$_3$ | CCl |
| 3-OCH$_3$ | H | H | OCH$_3$ | CH$_3$ | CCl |
| 3-CH$_3$ | CH$_3$ | H | Cl | OCH$_3$ | CCH$_3$ |
| 3-CH$_3$ | H | CH$_3$ | Br | OCH$_3$ | CCH$_3$ |
| 3-CH$_3$ | H | CH$_3$ | OC$_2$H$_5$ | CH$_3$ | CCH$_3$ |
| 3-CH$_3$ | H | CH$_3$ | CH$_3$ | OCH$_3$ | CCH$_2$CH$_3$ |
| 3-CH$_3$ | H | CH$_3$ | OCH$_3$ | OCH$_3$ | CCH$_2$CH$_2$Cl |
| 3-CH$_3$ | H | OCH$_3$ | OCH$_3$ | CH$_3$ | CCl |
| 3-NO$_2$ | H | CH$_3$ | OCH$_3$ | CH$_3$ | CCl |
| 3-Cl | CH$_3$ | H | OCH$_3$ | CH$_3$ | CCH$_3$ |
| 3-Br | H | OCH$_3$ | OCH$_3$ | CH$_3$ | CCl |
| 3-OCH$_3$ | H | CH$_3$ | CH$_3$ | CH$_3$ | CCl |
| 3-SO$_2$N(CH$_3$)$_2$ | H | CH$_3$ | H | CH$_3$ | CCl |
| 3-SO$_2$N(CH$_3$)(OCH$_3$) | H | CH$_3$ | H | CH$_3$ | CCl |
| 3-CH(CH$_3$)$_2$ | H | CH$_3$ | H | CH$_3$ | CCl |
| 3-CH$_2$CH$_3$ | H | CH$_3$ | H | CH$_3$ | CCl |

TABLE V-continued

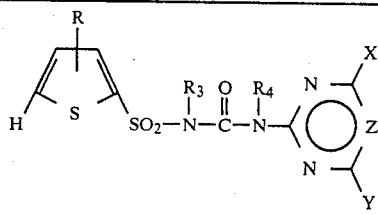

| R | R3 | R4 | X | Y | Z |
|---|---|---|---|---|---|
| 3-CH2CH=CH2 | H | CH3 | H | CH3 | CCl |
| 3-SO2N(C2H5)2 | H | CH3 | OCH2CH=CH2 | CH3 | CCl |
| 3-SO2N(CH3)2 | H | CH3 | OCH2C≡CH | CH3 | CCl |
| 3-SO2N(CH3)2 | H | CH3 | OCH2CH=CH2 | CH3 | CCN |
| 3-SO2N(CH3)2 | H | CH3 | OCH3 | CH3 | CCH2CH=CH2 |

TABLE V-a

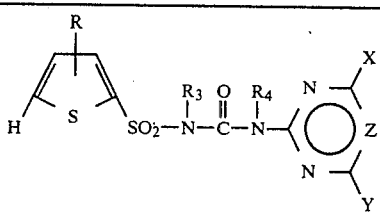

| R | R3 | R4 | X | Y | Z |
|---|---|---|---|---|---|
| 4-NO2 | H | H | CH3 | CH3 | C—Cl |
| 4-CH3 | H | H | CH3 | CH3 | C—Cl |
| 4-Cl | H | H | CH3 | CH3 | C—Cl |
| 4-NO2 | H | H | CH3 | CH3 | C—Br |
| 4-CH3 | H | H | CH3 | CH3 | C—Br |
| 4-Cl | H | H | CH3 | CH3 | C—Br |
| 4-NO2 | H | H | CH3 | CH3 | C—CN |
| 4-CH3 | H | H | CH3 | CH3 | C—CN |
| 4-Cl | H | H | CH3 | CH3 | C—CN |
| 4-NO2 | H | H | CH3 | CH3 | C—CH3 |
| 4-CH3 | H | H | CH3 | CH3 | C—CH3 |
| 4-Cl | H | H | CH3 | CH3 | C—CH3 |
| 4-NO2 | H | H | CH3 | CH3 | C—CH2CH3 |
| 4-CH3 | H | H | CH3 | CH3 | C—CH2CH3 |
| 4-Cl | H | H | CH3 | CH3 | C—CH2CH3 |
| 4-CH3 | H | H | CH3 | CH3 | C—CH2CH2Cl |
| 4-Cl | H | H | CH3 | CH3 | C—CH2CH2Cl |
| 4-CH3 | H | H | CH3 | CH3 | C—CH2CH=CH2 |
| 4-Cl | H | H | CH3 | CH3 | C—CH2CH=CH2 |
| 4-CH3 | H | H | H | CH3 | CCH3 |
| 4-CH3 | H | H | H | OCH3 | CCH3 |
| 4-CH3 | H | H | H | CH3 | CCl |
| 4-Br | H | H | H | CH3 | CBr |
| 4-CH3 | H | H | H | CH3 | CCN |
| 4-CH3 | H | H | H | CH3 | CBr |
| 4-SO2N(CH3)2 | H | H | CH3 | CH3 | CCl |
| 4-SO2N(CH3)2 | H | H | CH3 | CH3 | CBr |
| 4-SO2N(CH3)2 | H | H | CH3 | CH3 | CCN |
| 4-SO2N(CH3)2 | H | H | CH3 | CH3 | CCH3 |
| 4-SO2N(CH3)2 | H | H | CH3 | CH3 | CCH2CH3 |
| 4-SO2N(CH3)2 | H | H | CH3 | CH3 | CCH2CH2Cl |
| 4-SO2N(CH3)2 | H | H | OCH3 | OCH3 | CCH3 |
| 4-SO2N(CH3)(CH(CH3)2) | H | H | OCH3 | CH3 | CBr |
| 4-SO2N(CH3)(CH(CH3)2) | H | H | CH3 | CH3 | CCl |
| 4-SO2N(CH3)(CH(CH3)2) | H | H | CH3 | CH3 | CCH2CH2Cl |

TABLE V-a-continued

| R | R₃ | R₄ | X | Y | Z |
|---|---|---|---|---|---|
| 4-SO₂N(CH₃)(CH(CH₃)₂) | H | H | CH₃ | CH₃ | CCH₂CH₃ |
| 4-NO₂ | H | H | OCH₂CH=CH₂ | CH₃ | CCH₃ |
| 4-NO₂ | H | H | OCH₃ | CH₃ | CCl |
| 4-NO₂ | H | H | CH₃ | CH₃ | CCl |
| 4-OCH₃ | H | H | OCH₃ | CH₃ | CCl |
| 4-OCH₃ | H | H | OCH₃ | CH₃ | CCl |
| 4-CH₃ | CH₃ | H | Cl | OCH₃ | CCH₃ |
| 4-CH₃ | H | CH₃ | Br | OCH₃ | CCH₃ |
| 4-CH₃ | H | CH₃ | OC₂H₅ | CH₃ | CCH₃ |
| 4-CH₃ | H | CH₃ | CH₃ | OCH₃ | CCH₂CH₃ |
| 4-CH₃ | H | CH₃ | OCH₃ | OCH₃ | CCH₂CH₂Cl |
| 4-CH₃ | H | OCH₃ | OCH₃ | CH₃ | CCl |
| 4-NO₂ | H | CH₃ | OCH₃ | CH₃ | CCl |
| 4-Cl | CH₃ | H | OCH₃ | CH₃ | CCH₃ |
| 4-Br | H | OCH₃ | OCH₃ | CH₃ | CCl |
| 4-OCH₃ | H | CH₃ | CH₃ | CH₃ | CCl |
| 4-SO₂N(CH₃)₂ | H | CH₃ | H | CH₃ | CCl |
| 4-SO₂N(CH₃)(OCH₃) | H | CH₃ | H | CH₃ | CCl |
| 4-CH(CH₃)₂ | H | CH₃ | H | CH₃ | CCl |
| 4-CH₂CH₃ | H | CH₃ | H | CH₃ | CCl |
| 4-CH₂CH=CH₂ | H | CH₃ | H | CH₃ | CCl |
| 4-SO₂N(C₂H₅)₂ | H | CH₃ | OCH₂CH=CH₂ | CH₃ | CCl |
| 4-SO₂N(CH₃)₂ | H | CH₃ | OCH₂C≡CH | CH₃ | CCl |
| 4-SO₂N(CH₃)₂ | H | CH₃ | OCH₂CH=CH₂ | CH₃ | CCN |
| 4-SO₂N(CH₃)₂ | H | CH₃ | OCH₃ | CH₃ | CCH₂CH=CH₂ |

TABLE VI

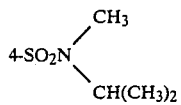

| R | R₃ | R₄ | X | Y | Z |
|---|---|---|---|---|---|
| 2-NO₂ | H | H | CH₃ | CH₃ | C—Cl |
| 2-CH₃ | H | H | CH₃ | CH₃ | C—Cl |
| 2-Cl | H | H | CH₃ | CH₃ | C—Cl |
| 2-NO₂ | H | H | CH₃ | CH₃ | C—Br |
| 2-CH₃ | H | H | CH₃ | CH₃ | C—Br |
| 2-Cl | H | H | CH₃ | CH₃ | C—Br |
| 2-NO₂ | H | H | CH₃ | CH₃ | C—CN |
| 2-CH₃ | H | H | CH₃ | CH₃ | C—CN |
| 2-Cl | H | H | CH₃ | CH₃ | C—CN |
| 2-NO₂ | H | H | CH₃ | CH₃ | C—CH₃ |
| 2-CH₃ | H | H | CH₃ | CH₃ | C—CH₃ |
| 2-Cl | H | H | CH₃ | CH₃ | C—CH₃ |
| 2-NO₂ | H | H | CH₃ | CH₃ | C—CH₂CH₃ |
| 2-CH₃ | H | H | CH₃ | CH₃ | C—CH₂CH₃ |
| 2-Cl | H | H | CH₃ | CH₃ | C—CH₂CH₃ |
| 2-CH₃ | H | H | CH₃ | CH₃ | C—CH₂CH₂Cl |
| 2-Cl | H | H | CH₃ | CH₃ | C—CH₂CH₂Cl |
| 2-CH₃ | H | H | CH₃ | CH₃ | C—CH₂CH=CH₂ |
| 2-Cl | H | H | CH₃ | CH₃ | C—CH₂CH=CH₂ |

TABLE VI-continued

Structure: R/H-thiophene-SO₂-N(R₃)-C(=O)-N(R₄)-[pyrimidine with X, Y, Z]

| R | R₃ | R₄ | X | Y | Z |
|---|---|---|---|---|---|
| 2-CH₃ | H | H | H | CH₃ | CCH₃ |
| 2-CH₃ | H | H | H | OCH₃ | CCH₃ |
| 2-CH₃ | H | H | H | CH₃ | CCl |
| 2-Br | H | H | H | CH₃ | CBr |
| 2-CH₃ | H | H | H | CH₃ | CCN |
| 2-CH₃ | H | H | H | CH₃ | CBr |
| 2-SO₂N(CH₃)₂ | H | H | CH₃ | CH₃ | CCl |
| 2-SO₂N(CH₃)₂ | H | H | CH₃ | CH₃ | CBr |
| 2-SO₂N(CH₃)₂ | H | H | CH₃ | CH₃ | CCN |
| 2-SO₂N(CH₃)₂ | H | H | CH₃ | CH₃ | CCH₃ |
| 2-SO₂N(CH₃)₂ | H | H | CH₃ | CH₃ | CCH₂CH₃ |
| 2-SO₂N(CH₃)₂ | H | H | CH₃ | CH₃ | CCH₂CH₂Cl |
| 2-SO₂N(CH₃)₂ | H | H | OCH₃ | OCH₃ | CCH₃ |
| 2-SO₂N(CH₃)(CH(CH₃)₂) | H | H | OCH₃ | CH₃ | CBr |
| 2-SO₂N(CH₃)(CH(CH₃)₂) | H | H | CH₃ | CH₃ | CCl |
| 2-SO₂N(CH₃)(CH(CH₃)₂) | H | H | CH₃ | CH₃ | CCH₂CH₂Cl |
| 2-SO₂N(CH₃)(CH(CH₃)₂) | H | H | CH₃ | CH₃ | CCH₂CH₃ |
| 2-NO₂ | H | H | OCH₂CH=CH₂ | CH₃ | CCH₃ |
| 2-NO₂ | H | H | OCH₃ | CH₃ | CCl |
| 2-NO₂ | H | H | CH₃ | CH₃ | CCl |
| 2-OCH₃ | H | H | OCH₃ | CH₃ | CCl |
| 2-OCH₃ | H | H | OCH₃ | CH₃ | CCl |
| 2-CH₃ | CH₃ | H | Cl | OCH₃ | CCH₃ |
| 2-CH₃ | H | CH₃ | Br | OCH₃ | CCH₃ |
| 2-CH₃ | H | CH₃ | OC₂H₅ | CH₃ | CCH₃ |
| 2-CH₃ | H | CH₃ | CH₃ | OCH₃ | CCH₂CH₃ |
| 2-CH₃ | H | CH₃ | OCH₃ | OCH₃ | CCH₂CH₂Cl |
| 2-CH₃ | H | OCH₃ | OCH₃ | CH₃ | CCl |
| 2-NO₂ | H | CH₃ | OCH₃ | CH₃ | CCl |
| 2-Cl | CH₃ | H | OCH₃ | CH₃ | CCH₃ |
| 2-Br | H | OCH₃ | OCH₃ | CH₃ | CCl |
| 2-OCH₃ | H | CH₃ | CH₃ | CH₃ | CCl |
| 2-SO₂N(CH₃)₂ | H | CH₃ | H | CH₃ | CCl |
| 2-SO₂N(CH₃)(OCH₃) | H | CH₃ | H | CH₃ | CCl |
| 2-CH(CH₃)₂ | H | CH₃ | H | CH₃ | CCl |
| 2-CH₂CH₃ | H | CH₃ | H | CH₃ | CCl |
| 2-CH₂CH=CH₂ | H | CH₃ | H | CH₃ | CCl |
| 2-SO₂N(C₂H₅)₂ | H | CH₃ | OCH₂CH=CH₂ | CH₃ | CCl |
| 2-SO₂N(CH₃)₂ | H | CH₃ | OCH₂C≡CH | CH₃ | CCl |
| 2-SO₂N(CH₃)₂ | H | CH₃ | OCH₂CH=CH₂ | CH₃ | CCN |
| 2-SO₂N(CH₃)₂ | H | CH₃ | OCH₃ | CH₃ | CCH₂CH=CH₂ |

TABLE VI-a

| R | R₃ | R₄ | X | Y | Z |
|---|---|---|---|---|---|
| 4-NO₂ | H | H | CH₃ | CH₃ | C—Cl |
| 4-CH₃ | H | H | CH₃ | CH₃ | C—Cl |
| 4-Cl | H | H | CH₃ | CH₃ | C—Cl |
| 4-NO₂ | H | H | CH₃ | CH₃ | C—Br |
| 4-CH₃ | H | H | CH₃ | CH₃ | C—Br |
| 4-Cl | H | H | CH₃ | CH₃ | C—Br |
| 4-NO₂ | H | H | CH₃ | CH₃ | C—CN |
| 4-CH₃ | H | H | CH₃ | CH₃ | C—CN |
| 4-Cl | H | H | CH₃ | CH₃ | C—CN |
| 4-NO₂ | H | H | CH₃ | CH₃ | C—CH₃ |
| 4-CH₃ | H | H | CH₃ | CH₃ | C—CH₃ |
| 4-Cl | H | H | CH₃ | CH₃ | C—CH₃ |
| 4-NO₂ | H | H | CH₃ | CH₃ | C—CH₂CH₃ |
| 4-CH₃ | H | H | CH₃ | CH₃ | C—CH₂CH₃ |
| 4-Cl | H | H | CH₃ | CH₃ | C—CH₂CH₃ |
| 4-CH₃ | H | H | CH₃ | CH₃ | C—CH₂CH₂Cl |
| 4-Cl | H | H | CH₃ | CH₃ | C—CH₂CH₂Cl |
| 4-CH₃ | H | H | CH₃ | CH₃ | C—CH₂CH=CH₂ |
| 4-Cl | H | H | CH₃ | CH₃ | C—CH₂CH=CH₂ |
| 4-CH₃ | H | H | H | CH₃ | CCH₃ |
| 4-CH₃ | H | H | H | OCH₃ | CCH₃ |
| 4-CH₃ | H | H | H | CH₃ | CCl |
| 4-Br | H | H | H | CH₃ | CBr |
| 4-CH₃ | H | H | H | CH₃ | CCN |
| 4-CH₃ | H | H | H | CH₃ | CBr |
| 4-SO₂N(CH₃)₂ | H | H | CH₃ | CH₃ | CCl |
| 4-SO₂N(CH₃)₂ | H | H | CH₃ | CH₃ | CBr |
| 4-SO₂N(CH₃)₂ | H | H | CH₃ | CH₃ | CCN |
| 4-SO₂N(CH₃)₂ | H | H | CH₃ | CH₃ | CCH₃ |
| 4-SO₂N(CH₃)₂ | H | H | CH₃ | CH₃ | CCH₂CH₃ |
| 4-SO₂N(CH₃)₂ | H | H | CH₃ | CH₃ | CCH₂CH₂Cl |
| 4-SO₂N(CH₃)₂ | H | H | OCH₃ | OCH₃ | CCH₃ |
| 4-SO₂N(CH₃)(CH(CH₃)₂) | H | H | OCH₃ | CH₃ | CBr |
| 4-SO₂N(CH₃)(CH(CH₃)₂) | H | H | CH₃ | CH₃ | CCl |
| 4-SO₂N(CH₃)(CH(CH₃)₂) | H | H | CH₃ | CH₃ | CCH₂CH₂Cl |
| 4-SO₂N(CH₃)(CH(CH₃)₂) | H | H | CH₃ | CH₃ | CCH₂CH₃ |
| 4-NO₂ | H | H | OCH₂CH=CH₂ | CH₃ | CCH₃ |
| 4-NO₂ | H | H | OCH₃ | CH₃ | CCl |
| 4-NO₂ | H | H | CH₃ | CH₃ | CCl |
| 4-OCH₃ | H | H | OCH₃ | CH₃ | CCl |
| 4-OCH₃ | H | H | OCH₃ | CH₃ | CCl |
| 4-CH₃ | CH₃ | H | Cl | OCH₃ | CCH₃ |
| 4-CH₃ | H | CH₃ | Br | OCH₃ | CCH₃ |
| 4-CH₃ | H | CH₃ | OC₂H₅ | CH₃ | CCH₃ |
| 4-CH₃ | H | CH₃ | CH₃ | OCH₃ | CCH₂CH₃ |
| 4-CH₃ | H | CH₃ | OCH₃ | OCH₃ | CCH₂CH₂Cl |
| 4-CH₃ | H | OCH₃ | OCH₃ | CH₃ | CCl |
| 4-NO₂ | H | CH₃ | OCH₃ | CH₃ | CCl |
| 4-Cl | CH₃ | H | OCH₃ | CH₃ | CCH₃ |
| 4-Br | H | OCH₃ | OCH₃ | CH₃ | CCl |
| 4-OCH₃ | H | CH₃ | CH₃ | CH₃ | CCl |
| 4-SO₂N(CH₃)₂ | H | CH₃ | H | CH₃ | CCl |

TABLE VI-a-continued

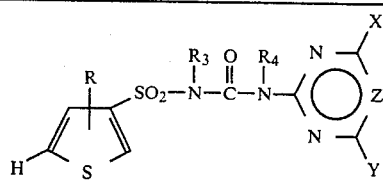

| R | R₃ | R₄ | X | Y | Z |
|---|---|---|---|---|---|
| 4-SO₂N(CH₃)(OCH₃) | H | CH₃ | H | CH₃ | CCl |
| 4-CH(CH₃)₂ | H | CH₃ | H | CH₃ | CCl |
| 4-CH₂CH₃ | H | CH₃ | H | CH₃ | CCl |
| 4-CH₂CH=CH₂ | H | CH₃ | H | CH₃ | CCl |
| 4-SO₂N(C₂H₅)₂ | H | CH₃ | OCH₂CH=CH₂ | CH₃ | CCl |
| 4-SO₂N(CH₃)₂ | H | CH₃ | OCH₂C≡CH | CH₃ | CCl |
| 4-SO₂N(CH₃)₂ | H | CH₃ | OCH₂CH=CH₂ | CH₃ | CCN |
| 4-SO₂N(CH₃)₂ | H | CH₃ | OCH₃ | CH₃ | CCH₂CH=CH₂ |

TABLE VII

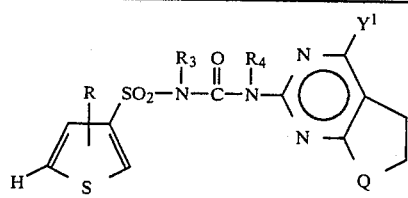

| R | R₃ | R₄ | Y¹ | Q |
|---|---|---|---|---|
| 2-CH₃ | H | H | H | O |
| 2-CH₃ | H | H | CH₃ | O |
| 2-CH₃ | H | H | OCH₃ | O |
| 2-CH₃ | H | H | Cl | O |
| 2-CH₃ | H | CH₃ | CH₃ | O |
| 2-CH₃ | H | OCH₃ | OCH₃ | O |
| 2-CH₃ | CH₃ | H | OCH₃ | O |
| 2-NO₂ | CH₃ | H | CH₃ | O |
| 2-NO₂ | H | CH₃ | CH₃ | O |
| 2-NO₂ | H | OCH₃ | CH₃ | O |
| 2-NO₂ | H | H | CH₃ | O |
| 2-NO₂ | H | H | OCH₃ | O |
| 2-Cl | CH₃ | H | OCH₃ | O |
| 2-Cl | H | CH₃ | OCH₃ | O |
| 2-Cl | H | H | OCH₃ | O |
| 2-Cl | H | H | CH₃ | O |
| 2-Br | CH₃ | H | CH₃ | O |
| 2-Br | H | CH₃ | CH₃ | O |
| 2-Br | H | H | OCH₃ | O |
| 2-Br | H | H | CH₃ | O |
| 2-OCH₃ | H | H | OCH₃ | O |
| 2-CH(CH₃)₂ | H | H | CH₃ | O |
| 2-(CH₂)₃CH₃ | H | H | CH₃ | O |
| 2-CH₂CH=CH₂ | H | H | CH₃ | O |
| 2-SO₂N(CH₃)₂ | H | H | CH₃ | O |
| 2-SO₂N(CH₃)₂ | H | H | OCH₃ | O |
| 2-SO₂N(CH₃)₂ | H | CH₃ | OCH₃ | O |
| 2-SO₂N(CH₃)₂ | H | H | Cl | O |
| 2-SO₂N(CH₃)₂ | H | H | H | O |
| 2-SO₂N(CH₃)(OCH₃) | H | H | CH₃ | O |
| 2-NO₂ | H | H | OCH₃ | CH₂ |
| 2-NO₂ | H | CH₃ | OCH₃ | CH₂ |
| 2-NO₂ | H | OCH₃ | OCH₃ | CH₂ |
| 2-NO₂ | H | H | CH₃ | CH₂ |
| 2-NO₂ | CH₃ | H | OCH₃ | CH₂ |
| 2-SO₂N(CH₃)₂ | H | H | OCH₃ | CH₂ |

TABLE VII-continued

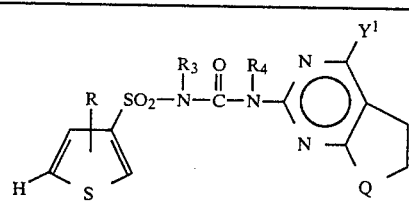

| R | R₃ | R₄ | Y¹ | Q |
|---|---|---|---|---|
| 2-SO₂N(CH₃)₂ | H | CH₃ | OCH₃ | CH₂ |
| 2-SO₂N(CH₃)₂ | CH₃ | H | OCH₃ | CH₂ |
| 2-SO₂N(CH₃)₂ | CH₃ | CH₃ | OCH₃ | CH₂ |
| 2-Cl | CH₃ | H | OCH₃ | CH₂ |
| 2-Cl | H | CH₃ | OCH₃ | CH₂ |
| 2-Cl | H | H | OCH₃ | CH₂ |
| 2-Cl | H | H | CH₃ | CH₂ |
| 2-Br | CH₃ | H | OCH₃ | CH₂ |
| 2-Br | H | OCH₃ | OCH₃ | CH₂ |
| 2-Br | H | H | H | CH₂ |
| 2-Br | H | H | CH₃ | CH₂ |
| 2-OCH₃ | H | H | OCH₃ | CH₂ |
| 2-SO₂N(CH₃)₂ | H | H | Cl | CH₂ |
| 2-SO₂N(CH₃)₂ | H | H | H | CH₂ |
| 4-CH₃ | H | H | H | O |
| 4-CH₃ | H | H | CH₃ | O |
| 4-CH₃ | H | H | OCH₃ | O |
| 4-CH₃ | H | H | Cl | O |
| 4-CH₃ | H | CH₃ | CH₃ | O |
| 4-CH₃ | H | OCH₃ | OCH₃ | O |
| 4-CH₃ | CH₃ | H | OCH₃ | O |
| 4-NO₂ | CH₃ | H | CH₃ | O |
| 4-NO₂ | H | CH₃ | CH₃ | O |
| 4-NO₂ | H | OCH₃ | CH₃ | O |
| 4-NO₂ | H | H | CH₃ | O |
| 4-NO₂ | H | H | OCH₃ | O |
| 4-Cl | CH₃ | H | OCH₃ | O |
| 4-Cl | H | CH₃ | OCH₃ | O |
| 4-Cl | H | H | OCH₃ | O |
| 4-Cl | H | H | CH₃ | O |
| 4-Br | CH₃ | H | CH₃ | O |
| 4-Br | H | CH₃ | CH₃ | O |
| 4-Br | H | H | OCH₃ | O |
| 4-Br | H | H | CH₃ | O |
| 4-OCH₃ | H | H | OCH₃ | O |
| 4-CH(CH₃)₂ | H | H | CH₃ | O |
| 4-(CH₂)₃CH₃ | H | H | CH₃ | O |
| 4-CH₂CH=CH₂ | H | H | CH₃ | O |
| 4-SO₂N(CH₃)₂ | H | H | OCH₃ | O |
| 4-SO₂N(CH₃)₂ | H | H | OCH₃ | O |
| 4-SO₂N(CH₃)₂ | H | CH₃ | OCH₃ | O |
| 4-SO₂N(CH₃)₂ | H | H | Cl | O |

TABLE VII-continued

![Structure: thiophene with R substituent, SO2-N(R3)-C(O)-N(R4) linked to fused bicyclic pyrimidine with Y1 and Q]

| R | R3 | R4 | Y1 | Q |
|---|----|----|----|----|
| 4-SO₂N(CH₃)₂ | H | H | H | O |
| 4-SO₂N(CH₃)(OCH₃) | H | H | CH₃ | O |
| 4-NO₂ | H | H | OCH₃ | CH₂ |
| 4-NO₂ | H | CH₃ | OCH₃ | CH₂ |
| 4-NO₂ | H | OCH₃ | OCH₃ | CH₂ |
| 4-NO₂ | H | H | CH₃ | CH₂ |
| 4-NO₂ | CH₃ | H | OCH₃ | CH₂ |
| 4-SO₂N(CH₃)₂ | H | H | OCH₃ | CH₂ |
| 4-SO₂N(CH₃)₂ | H | CH₃ | OCH₃ | CH₂ |
| 4-SO₂N(CH₃)₂ | CH₃ | H | OCH₃ | CH₂ |
| 4-SO₂N(CH₃)₂ | CH₃ | CH₃ | OCH₃ | CH₂ |
| 4-Cl | CH₃ | H | OCH₃ | CH₂ |
| 4-Cl | H | CH₃ | OCH₃ | CH₂ |
| 4-Cl | H | H | OCH₃ | CH₂ |
| 4-Cl | H | H | CH₃ | CH₂ |
| 4-Br | CH₃ | H | OCH₃ | CH₂ |
| 4-Br | H | OCH₃ | OCH₃ | CH₂ |
| 4-Br | H | H | H | CH₂ |
| 4-Br | H | H | CH₃ | CH₂ |
| 4-OCH₃ | H | H | OCH₃ | CH₂ |
| 4-SO₂N(CH₃)₂ | H | H | Cl | CH₂ |
| 4-SO₂N(CH₃)₂ | H | H | H | CH₂ |

TABLE VII-a

![Structure: thiophene with R substituent, SO2-N(R3)-C(O)-N(R4) linked to fused bicyclic pyrimidine with Y1 and Q]

| R | R3 | R4 | Y1 | Q |
|---|----|----|----|----|
| 3-CH₃ | H | H | H | O |
| 3-CH₃ | H | H | CH₃ | O |
| 3-CH₃ | H | H | OCH₃ | O |
| 3-CH₃ | H | H | Cl | O |
| 3-CH₃ | H | CH₃ | CH₃ | O |
| 3-CH₃ | H | OCH₃ | OCH₃ | O |
| 3-CH₃ | CH₃ | H | OCH₃ | O |
| 3-NO₂ | CH₃ | H | CH₃ | O |
| 3-NO₂ | H | CH₃ | CH₃ | O |
| 3-NO₂ | H | OCH₃ | CH₃ | O |
| 3-NO₂ | H | H | CH₃ | O |
| 3-NO₂ | H | H | OCH₃ | O |
| 3-Cl | CH₃ | H | OCH₃ | O |
| 3-Cl | H | CH₃ | OCH₃ | O |
| 3-Cl | H | H | OCH₃ | O |
| 3-Cl | H | H | CH₃ | O |
| 3-Br | CH₃ | H | CH₃ | O |
| 3-Br | H | CH₃ | CH₃ | O |
| 3-Br | H | H | OCH₃ | O |
| 3-Br | H | H | CH₃ | O |
| 3-OCH₃ | H | H | OCH₃ | O |
| 3-CH(CH₃)₂ | H | H | CH₃ | O |
| 3-(CH₂)₃CH₃ | H | H | CH₃ | O |
| 3-CH₂CH=CH₂ | H | H | CH₃ | O |
| 3-SO₂N(CH₃)₂ | H | H | CH₃ | O |
| 3-SO₂N(CH₃)₂ | H | H | OCH₃ | O |

TABLE VII-a-continued

![Structure: thiophene with R substituent, SO2-N(R3)-C(O)-N(R4) linked to fused bicyclic pyrimidine with Y1 and Q]

| R | R3 | R4 | Y1 | Q |
|---|----|----|----|----|
| 3-SO₂N(CH₃)₂ | H | CH₃ | OCH₃ | O |
| 3-SO₂N(CH₃)₂ | H | H | Cl | O |
| 3-SO₂N(CH₃)₂ | H | H | H | O |
| 3-SO₂N(CH₃)(OCH₃) | H | H | CH₃ | O |
| 3-NO₂ | H | H | OCH₃ | CH₂ |
| 3-NO₂ | H | CH₃ | OCH₃ | CH₂ |
| 3-NO₂ | H | OCH₃ | OCH₃ | CH₂ |
| 3-NO₂ | H | H | CH₃ | CH₂ |
| 3-NO₂ | CH₃ | H | OCH₃ | CH₂ |
| 3-SO₂N(CH₃)₂ | H | H | OCH₃ | CH₂ |
| 3-SO₂N(CH₃)₂ | H | CH₃ | OCH₃ | CH₂ |
| 3-SO₂N(CH₃)₂ | CH₃ | H | OCH₃ | CH₂ |
| 3-SO₂N(CH₃)₂ | CH₃ | CH₃ | OCH₃ | CH₂ |
| 3-Cl | CH₃ | H | OCH₃ | CH₂ |
| 3-Cl | H | CH₃ | OCH₃ | CH₂ |
| 3-Cl | H | H | OCH₃ | CH₂ |
| 3-Cl | H | H | CH₃ | CH₂ |
| 3-Br | CH₃ | H | OCH₃ | CH₂ |
| 3-Br | H | OCH₃ | OCH₃ | CH₂ |
| 3-Br | H | H | H | CH₂ |
| 3-Br | H | H | CH₃ | CH₂ |
| 3-OCH₃ | H | H | OCH₃ | CH₂ |
| 3-SO₂N(CH₃)₂ | H | H | Cl | CH₂ |
| 3-SO₂N(CH₃)₂ | H | H | H | CH₂ |
| 4-CH₃ | H | H | H | O |
| 4-CH₃ | H | H | CH₃ | O |
| 4-CH₃ | H | H | OCH₃ | O |
| 4-CH₃ | H | H | Cl | O |
| 4-CH₃ | H | CH₃ | CH₃ | O |
| 4-CH₃ | H | OCH₃ | OCH₃ | O |
| 4-CH₃ | CH₃ | H | OCH₃ | O |
| 4-NO₂ | CH₃ | H | CH₃ | O |
| 4-NO₂ | H | CH₃ | CH₃ | O |
| 4-NO₂ | H | OCH₃ | CH₃ | O |
| 4-NO₂ | H | H | CH₃ | O |
| 4-NO₂ | H | H | OCH₃ | O |
| 4-Cl | CH₃ | H | OCH₃ | O |
| 4-Cl | H | CH₃ | OCH₃ | O |
| 4-Cl | H | H | OCH₃ | O |
| 4-Cl | H | H | CH₃ | O |
| 4-Br | CH₃ | H | CH₃ | O |
| 4-Br | H | CH₃ | CH₃ | O |
| 4-Br | H | H | OCH₃ | O |
| 4-Br | H | H | CH₃ | O |
| 4-OCH₃ | H | H | OCH₃ | O |
| 4-CH(CH₃)₂ | H | H | CH₃ | O |
| 4-(CH₂)₃CH₃ | H | H | CH₃ | O |
| 4-CH₂CH=CH₂ | H | H | CH₃ | O |
| 4-SO₂N(CH₃)₂ | H | H | CH₃ | O |
| 4-SO₂N(CH₃)₂ | H | H | OCH₃ | O |
| 4-SO₂N(CH₃)₂ | H | CH₃ | OCH₃ | O |
| 4-SO₂N(CH₃)₂ | H | H | Cl | O |
| 4-SO₂N(CH₃)₂ | H | H | H | O |
| 4-SO₂N(CH₃)(OCH₃) | H | H | CH₃ | O |
| 4-NO₂ | H | H | OCH₃ | CH₂ |
| 4-NO₂ | H | CH₃ | OCH₃ | CH₂ |
| 4-NO₂ | H | OCH₃ | OCH₃ | CH₂ |
| 4-NO₂ | H | H | CH₃ | CH₂ |

TABLE VII-a-continued

| R | R3 | R4 | Y1 | Q |
|---|---|---|---|---|
| 4-NO2 | CH3 | H | OCH3 | CH2 |
| 4-SO2N(CH3)2 | H | H | OCH3 | CH2 |
| 4-SO2N(CH3)2 | H | CH3 | OCH3 | CH2 |
| 4-SO2N(CH3)2 | CH3 | H | OCH3 | CH2 |
| 4-SO2N(CH3)2 | CH3 | CH3 | OCH3 | CH2 |
| 4-Cl | CH3 | H | OCH3 | CH2 |
| 4-Cl | H | CH3 | OCH3 | CH2 |
| 4-Cl | H | H | OCH3 | CH2 |
| 4-Cl | H | H | CH3 | CH2 |
| 4-Br | CH3 | H | OCH3 | CH2 |
| 4-Br | H | OCH3 | OCH3 | CH2 |
| 4-Br | H | H | H | CH2 |
| 4-Br | H | H | CH3 | CH2 |
| 4-OCH3 | H | H | OCH3 | CH2 |
| 4-SO2N(CH3)2 | H | H | Cl | CH2 |
| 4-SO2N(CH3)2 | H | H | H | CH2 |

TABLE VIII

| R | R3 | R4 | Y1 | Q |
|---|---|---|---|---|
| 2-CH3 | H | H | H | O |
| 2-CH3 | H | H | CH3 | O |
| 2-CH3 | H | H | OCH3 | O |
| 2-CH3 | H | H | Cl | O |
| 2-CH3 | H | CH3 | CH3 | O |
| 2-CH3 | H | OCH3 | OCH3 | O |
| 2-CH3 | CH3 | H | OCH3 | O |
| 2-NO2 | CH3 | H | CH3 | O |
| 2-NO2 | H | CH3 | CH3 | O |
| 2-NO2 | H | OCH3 | CH3 | O |
| 2-NO2 | H | H | CH3 | O |
| 2-NO2 | H | H | OCH3 | O |
| 2-Cl | CH3 | H | OCH3 | O |
| 2-Cl | H | CH3 | OCH3 | O |
| 2-Cl | H | H | OCH3 | O |
| 2-Cl | H | H | CH3 | O |
| 2-Br | CH3 | H | CH3 | O |
| 2-Br | H | CH3 | CH3 | O |
| 2-Br | H | H | OCH3 | O |
| 2-Br | H | H | CH3 | O |
| 2-OCH3 | H | H | OCH3 | O |
| 2-CH(CH3)2 | H | H | CH3 | O |
| 2-(CH2)3CH3 | H | H | CH3 | O |
| 2-CH2CH=CH2 | H | H | CH3 | O |
| 2-SO2N(CH3)2 | H | H | CH3 | O |
| 2-SO2N(CH3)2 | H | H | OCH3 | O |
| 2-SO2N(CH3)2 | H | CH3 | OCH3 | O |
| 2-SO2N(CH3)2 | H | H | Cl | O |
| 2-SO2N(CH3)2 | H | H | H | O |
| 2-SO2N(CH3)(OCH3) | H | H | CH3 | O |
| 2-NO2 | H | H | OCH3 | CH2 |
| 2-NO2 | H | CH3 | OCH3 | CH2 |

TABLE VIII-continued

| R | R3 | R4 | Y1 | Q |
|---|---|---|---|---|
| 2-NO2 | H | OCH3 | OCH3 | CH2 |
| 2-NO2 | H | H | CH3 | CH2 |
| 2-NO2 | CH3 | H | OCH3 | CH2 |
| 2-SO2N(CH3)2 | H | H | OCH3 | CH2 |
| 2-SO2N(CH3)2 | H | CH3 | OCH3 | CH2 |
| 2-SO2N(CH3)2 | CH3 | H | OCH3 | CH2 |
| 2-SO2N(CH3)2 | CH3 | CH3 | OCH3 | CH2 |
| 2-Cl | CH3 | H | OCH3 | CH2 |
| 2-Cl | H | CH3 | OCH3 | CH2 |
| 2-Cl | H | H | OCH3 | CH2 |
| 2-Cl | H | H | CH3 | CH2 |
| 2-Br | CH3 | H | OCH3 | CH2 |
| 2-Br | H | OCH3 | OCH3 | CH2 |
| 2-Br | H | H | H | CH2 |
| 2-Br | H | H | CH3 | CH2 |
| 2-OCH3 | H | H | OCH3 | CH2 |
| 2-SO2N(CH3)2 | H | H | Cl | CH2 |
| 2-SO2N(CH3)2 | H | H | H | CH2 |
| 4-CH3 | H | H | H | O |
| 4-CH3 | H | H | CH3 | O |
| 4-CH3 | H | H | OCH3 | O |
| 4-CH3 | H | H | Cl | O |
| 4-CH3 | H | CH3 | CH3 | O |
| 4-CH3 | H | OCH3 | OCH3 | O |
| 4-CH3 | CH3 | H | OCH3 | O |
| 4-NO2 | CH3 | H | CH3 | O |
| 4-NO2 | H | CH3 | CH3 | O |
| 4-NO2 | H | OCH3 | CH3 | O |
| 4-NO2 | H | H | CH3 | O |
| 4-NO2 | H | H | OCH3 | O |
| 4-Cl | CH3 | H | OCH3 | O |
| 4-Cl | H | CH3 | OCH3 | O |
| 4-Cl | H | H | OCH3 | O |
| 4-Cl | H | H | CH3 | O |
| 4-Br | CH3 | H | CH3 | O |
| 4-Br | H | CH3 | CH3 | O |
| 4-Br | H | H | OCH3 | O |
| 4-Br | H | H | CH3 | O |
| 4-OCH3 | H | H | OCH3 | O |
| 4-CH(CH3)2 | H | H | CH3 | O |
| 4-(CH2)3CH3 | H | H | CH3 | O |
| 4-CH2CH=CH2 | H | H | CH3 | O |
| 4-SO2N(CH3)2 | H | H | CH3 | O |
| 4-SO2N(CH3)2 | H | H | OCH3 | O |
| 4-SO2N(CH3)2 | H | CH3 | OCH3 | O |
| 4-SO2N(CH3)2 | H | H | Cl | O |
| 4-SO2N(CH3)2 | H | H | H | O |
| 4-SO2N(CH3)(OCH3) | H | H | CH3 | O |
| 4-NO2 | H | H | OCH3 | CH2 |
| 4-NO2 | H | CH3 | OCH3 | CH2 |
| 4-NO2 | H | OCH3 | OCH3 | CH2 |
| 4-NO2 | H | H | CH3 | CH2 |
| 4-NO2 | CH3 | H | OCH3 | CH2 |
| 4-SO2N(CH3)2 | H | H | OCH3 | CH2 |
| 4-SO2N(CH3)2 | H | CH3 | OCH3 | CH2 |
| 4-SO2N(CH3)2 | CH3 | H | OCH3 | CH2 |
| 4-SO2N(CH3)2 | CH3 | CH3 | OCH3 | CH2 |
| 4-Cl | CH3 | H | OCH3 | CH2 |
| 4-Cl | H | CH3 | OCH3 | CH2 |
| 4-Cl | H | H | OCH3 | CH2 |
| 4-Cl | H | H | CH3 | CH2 |
| 4-Br | CH3 | H | OCH3 | CH2 |
| 4-Br | H | OCH3 | OCH3 | CH2 |
| 4-Br | H | H | H | CH2 |
| 4-Br | H | H | CH3 | CH2 |

TABLE VIII-continued

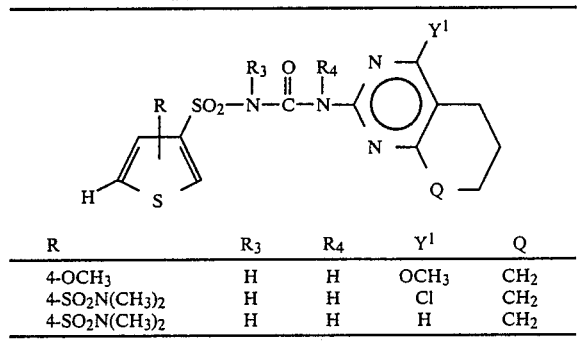

| R | R₃ | R₄ | Y¹ | Q |
|---|----|----|----|---|
| 4-OCH₃ | H | H | OCH₃ | CH₂ |
| 4-SO₂N(CH₃)₂ | H | H | Cl | CH₂ |
| 4-SO₂N(CH₃)₂ | H | H | H | CH₂ |

TABLE VIII-a

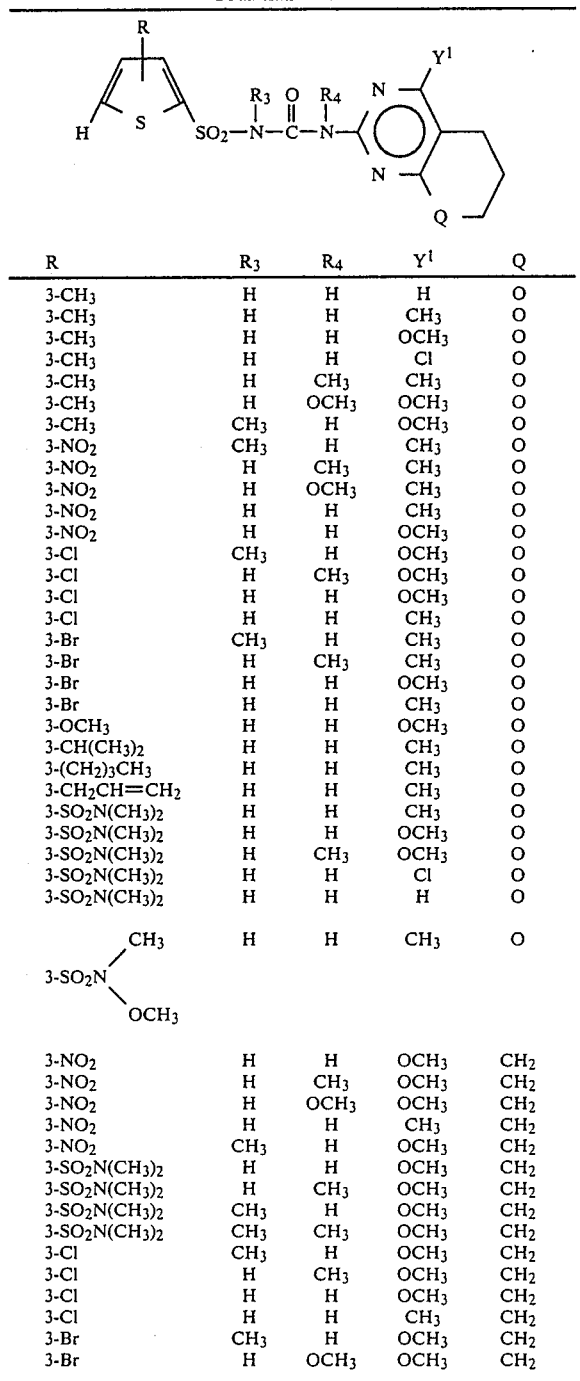

| R | R₃ | R₄ | Y¹ | Q |
|---|----|----|----|---|
| 3-CH₃ | H | H | H | O |
| 3-CH₃ | H | H | CH₃ | O |
| 3-CH₃ | H | H | OCH₃ | O |
| 3-CH₃ | H | H | Cl | O |
| 3-CH₃ | H | CH₃ | CH₃ | O |
| 3-CH₃ | H | OCH₃ | OCH₃ | O |
| 3-CH₃ | CH₃ | H | OCH₃ | O |
| 3-NO₂ | CH₃ | H | CH₃ | O |
| 3-NO₂ | H | CH₃ | CH₃ | O |
| 3-NO₂ | H | OCH₃ | CH₃ | O |
| 3-NO₂ | H | H | CH₃ | O |
| 3-NO₂ | H | H | OCH₃ | O |
| 3-Cl | CH₃ | H | OCH₃ | O |
| 3-Cl | H | CH₃ | OCH₃ | O |
| 3-Cl | H | H | OCH₃ | O |
| 3-Cl | H | H | CH₃ | O |
| 3-Br | CH₃ | H | CH₃ | O |
| 3-Br | H | CH₃ | CH₃ | O |
| 3-Br | H | H | OCH₃ | O |
| 3-Br | H | H | CH₃ | O |
| 3-OCH₃ | H | H | OCH₃ | O |
| 3-CH(CH₃)₂ | H | H | CH₃ | O |
| 3-(CH₂)₃CH₃ | H | H | CH₃ | O |
| 3-CH₂CH=CH₂ | H | H | CH₃ | O |
| 3-SO₂N(CH₃)₂ | H | H | CH₃ | O |
| 3-SO₂N(CH₃)₂ | H | H | OCH₃ | O |
| 3-SO₂N(CH₃)₂ | H | CH₃ | OCH₃ | O |
| 3-SO₂N(CH₃)₂ | H | H | Cl | O |
| 3-SO₂N(CH₃)₂ | H | H | H | O |
| 3-SO₂N(CH₃)(OCH₃) | H | H | CH₃ | O |
| 3-NO₂ | H | H | OCH₃ | CH₂ |
| 3-NO₂ | H | CH₃ | OCH₃ | CH₂ |
| 3-NO₂ | H | OCH₃ | OCH₃ | CH₂ |
| 3-NO₂ | H | H | CH₃ | CH₂ |
| 3-NO₂ | CH₃ | H | OCH₃ | CH₂ |
| 3-SO₂N(CH₃)₂ | H | H | OCH₃ | CH₂ |
| 3-SO₂N(CH₃)₂ | H | CH₃ | OCH₃ | CH₂ |
| 3-SO₂N(CH₃)₂ | CH₃ | H | OCH₃ | CH₂ |
| 3-SO₂N(CH₃)₂ | CH₃ | CH₃ | OCH₃ | CH₂ |
| 3-Cl | CH₃ | H | OCH₃ | CH₂ |
| 3-Cl | H | CH₃ | OCH₃ | CH₂ |
| 3-Cl | H | H | OCH₃ | CH₂ |
| 3-Cl | H | H | CH₃ | CH₂ |
| 3-Br | CH₃ | H | OCH₃ | CH₂ |
| 3-Br | H | OCH₃ | OCH₃ | CH₂ |

TABLE VIII-a-continued

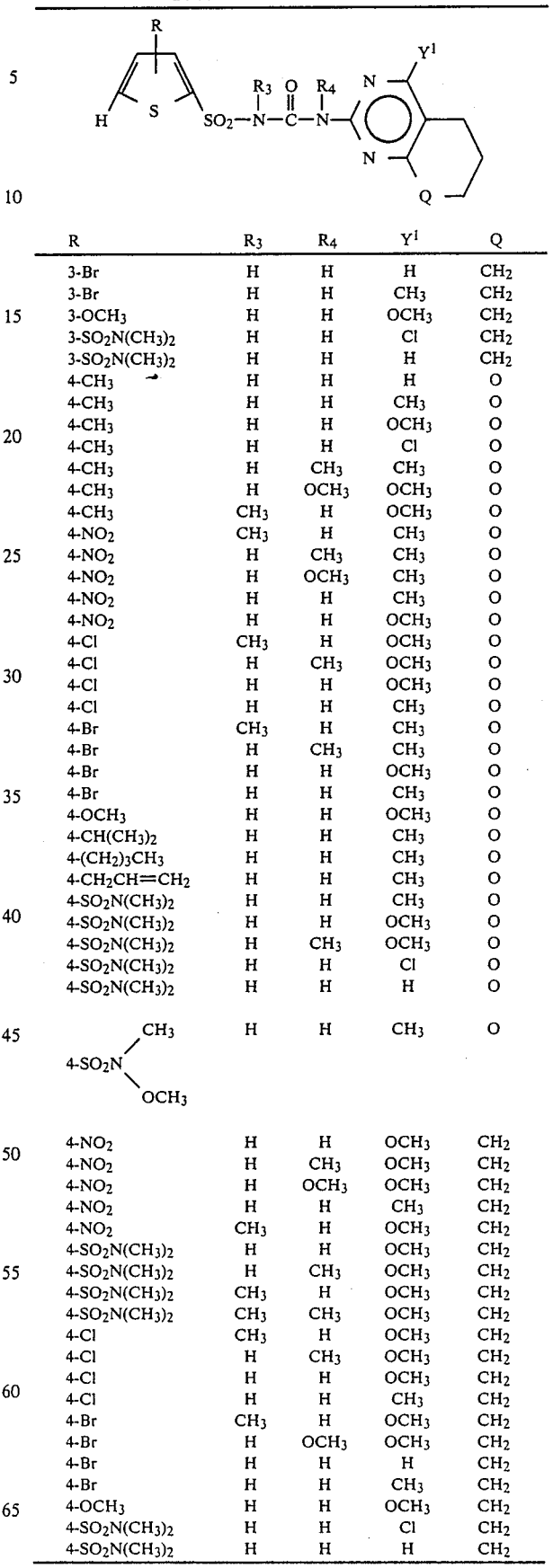

| R | R₃ | R₄ | Y¹ | Q |
|---|----|----|----|---|
| 3-Br | H | H | H | CH₂ |
| 3-Br | H | H | CH₃ | CH₂ |
| 3-OCH₃ | H | H | OCH₃ | CH₂ |
| 3-SO₂N(CH₃)₂ | H | H | Cl | CH₂ |
| 3-SO₂N(CH₃)₂ | H | H | H | CH₂ |
| 4-CH₃ | H | H | H | O |
| 4-CH₃ | H | H | CH₃ | O |
| 4-CH₃ | H | H | OCH₃ | O |
| 4-CH₃ | H | H | Cl | O |
| 4-CH₃ | H | CH₃ | CH₃ | O |
| 4-CH₃ | H | OCH₃ | OCH₃ | O |
| 4-CH₃ | CH₃ | H | OCH₃ | O |
| 4-NO₂ | CH₃ | H | CH₃ | O |
| 4-NO₂ | H | CH₃ | CH₃ | O |
| 4-NO₂ | H | OCH₃ | CH₃ | O |
| 4-NO₂ | H | H | CH₃ | O |
| 4-NO₂ | H | H | OCH₃ | O |
| 4-Cl | CH₃ | H | OCH₃ | O |
| 4-Cl | H | CH₃ | OCH₃ | O |
| 4-Cl | H | H | OCH₃ | O |
| 4-Cl | H | H | CH₃ | O |
| 4-Br | CH₃ | H | CH₃ | O |
| 4-Br | H | CH₃ | CH₃ | O |
| 4-Br | H | H | OCH₃ | O |
| 4-Br | H | H | CH₃ | O |
| 4-OCH₃ | H | H | OCH₃ | O |
| 4-CH(CH₃)₂ | H | H | CH₃ | O |
| 4-(CH₂)₃CH₃ | H | H | CH₃ | O |
| 4-CH₂CH=CH₂ | H | H | CH₃ | O |
| 4-SO₂N(CH₃)₂ | H | H | CH₃ | O |
| 4-SO₂N(CH₃)₂ | H | H | OCH₃ | O |
| 4-SO₂N(CH₃)₂ | H | CH₃ | OCH₃ | O |
| 4-SO₂N(CH₃)₂ | H | H | Cl | O |
| 4-SO₂N(CH₃)₂ | H | H | H | O |
| 4-SO₂N(CH₃)(OCH₃) | H | H | CH₃ | O |
| 4-NO₂ | H | H | OCH₃ | CH₂ |
| 4-NO₂ | H | CH₃ | OCH₃ | CH₂ |
| 4-NO₂ | H | OCH₃ | OCH₃ | CH₂ |
| 4-NO₂ | H | H | CH₃ | CH₂ |
| 4-NO₂ | CH₃ | H | OCH₃ | CH₂ |
| 4-SO₂N(CH₃)₂ | H | H | OCH₃ | CH₂ |
| 4-SO₂N(CH₃)₂ | H | CH₃ | OCH₃ | CH₂ |
| 4-SO₂N(CH₃)₂ | CH₃ | H | OCH₃ | CH₂ |
| 4-SO₂N(CH₃)₂ | CH₃ | CH₃ | OCH₃ | CH₂ |
| 4-Cl | CH₃ | H | OCH₃ | CH₂ |
| 4-Cl | H | CH₃ | OCH₃ | CH₂ |
| 4-Cl | H | H | OCH₃ | CH₂ |
| 4-Cl | H | H | CH₃ | CH₂ |
| 4-Br | CH₃ | H | CH₃ | CH₂ |
| 4-Br | H | OCH₃ | OCH₃ | CH₂ |
| 4-Br | H | H | H | CH₂ |
| 4-Br | H | H | CH₃ | CH₂ |
| 4-OCH₃ | H | H | OCH₃ | CH₂ |
| 4-SO₂N(CH₃)₂ | H | H | Cl | CH₂ |
| 4-SO₂N(CH₃)₂ | H | H | H | CH₂ |

TABLE IX

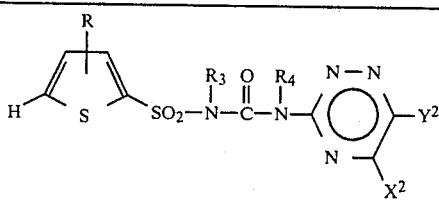

| R | $R_3$ | $R_4$ | $X^2$ | $Y^2$ |
|---|---|---|---|---|
| 3-CH$_3$ | H | H | CH$_3$ | CH$_3$ |
| 3-Cl | H | H | CH$_3$ | CH$_3$ |
| 3-Br | H | H | CH$_3$ | CH$_3$ |
| 3-NO$_2$ | H | H | CH$_3$ | CH$_3$ |
| 3-SO$_2$N(CH$_3$)$_2$ | H | H | CH$_3$ | CH$_3$ |
| 3-SO$_2$N(C$_2$H$_5$)$_2$ | H | H | CH$_3$ | CH$_3$ |
| 3-SO$_2$N(CH$_3$)CH(CH$_3$)$_2$ | H | H | CH$_3$ | CH$_3$ |
| 3-SO$_2$N(CH$_3$)CH$_2$CH$_2$CH$_3$ | H | H | CH$_3$ | CH$_3$ |
| 3-OCH$_3$ | H | H | CH$_3$ | CH$_3$ |
| 3-CH$_2$CH$_3$ | H | H | CH$_3$ | CH$_3$ |
| 3-CH(CH$_3$)$_2$ | H | H | CH$_3$ | CH$_3$ |
| 3-CH$_2$CH(CH$_3$)$_2$ | H | H | CH$_3$ | CH$_3$ |
| 3-CH$_2$CH=CH$_2$ | H | H | CH$_3$ | CH$_3$ |
| 3-(CH$_2$)$_3$CH$_3$ | H | H | CH$_3$ | CH$_3$ |
| 3-SO$_2$N(OCH$_3$)CH$_3$ | H | H | CH$_3$ | CH$_3$ |
| 3-NO$_2$ | CH$_3$ | H | CH$_3$ | CH$_3$ |
| 3-SO$_2$N(CH$_3$)$_2$ | CH$_3$ | H | CH$_3$ | CH$_3$ |
| 3-Br | H | CH$_3$ | CH$_3$ | CH$_3$ |
| 3-Cl | H | CH$_3$ | CH$_3$ | CH$_3$ |
| 4-CH$_3$ | H | H | CH$_3$ | CH$_3$ |
| 4-Cl | H | H | CH$_3$ | CH$_3$ |
| 4-Br | H | H | CH$_3$ | CH$_3$ |
| 4-NO$_2$ | H | H | CH$_3$ | CH$_3$ |
| 4-SO$_2$N(CH$_3$)$_2$ | H | H | CH$_3$ | CH$_3$ |
| 4-SO$_2$N(C$_2$H$_5$)$_2$ | H | H | CH$_3$ | CH$_3$ |
| 4-SO$_2$N(CH$_3$)CH(CH$_3$)$_2$ | H | H | CH$_3$ | CH$_3$ |
| 4-SO$_2$N(CH$_3$)CH$_2$CH$_2$CH$_3$ | H | H | CH$_3$ | CH$_3$ |
| 4-OCH$_3$ | H | H | CH$_3$ | CH$_3$ |
| 4-CH$_2$CH$_3$ | H | H | CH$_3$ | CH$_3$ |
| 4-CH(CH$_3$)$_2$ | H | H | CH$_3$ | CH$_3$ |
| 4-CH$_2$CH(CH$_3$)$_2$ | H | H | CH$_3$ | CH$_3$ |
| 4-CH$_2$CH=CH$_2$ | H | H | CH$_3$ | CH$_3$ |
| 4-(CH$_2$)$_3$CH$_3$ | H | H | CH$_3$ | CH$_3$ |
| 4-SO$_2$N(OCH$_3$)CH$_3$ | H | H | CH$_3$ | CH$_3$ |
| 4-NO$_2$ | CH$_3$ | H | CH$_3$ | CH$_3$ |
| 4-SO$_2$N(CH$_3$)$_2$ | CH$_3$ | H | CH$_3$ | CH$_3$ |
| 4-Br | H | CH$_3$ | CH$_3$ | CH$_3$ |
| 4-Cl | H | CH$_3$ | CH$_3$ | CH$_3$ |
| 3-CH$_3$ | H | H | OCH$_3$ | CH$_3$ |
| 3-Cl | H | H | OCH$_3$ | CH$_3$ |
| 3-Br | H | H | OCH$_3$ | CH$_3$ |
| 3-NO$_2$ | H | H | OCH$_3$ | CH$_3$ |
| 3-SO$_2$N(CH$_3$)$_2$ | H | H | OCH$_3$ | CH$_3$ |
| 3-SO$_2$N(C$_2$H$_5$)$_2$ | H | H | OCH$_3$ | CH$_3$ |
| 3-SO$_2$N(CH$_3$)CH(CH$_3$)$_2$ | H | H | OCH$_3$ | CH$_3$ |
| 3-SO$_2$N(CH$_3$)CH$_2$CH$_2$CH$_3$ | H | H | OCH$_3$ | CH$_3$ |
| 3-OCH$_3$ | H | H | OCH$_3$ | CH$_3$ |
| 3-CH$_2$CH$_3$ | H | H | OCH$_3$ | CH$_3$ |
| 3-CH(CH$_3$)$_2$ | H | H | OCH$_3$ | CH$_3$ |
| 3-CH$_2$CH(CH$_3$)$_2$ | H | H | OCH$_3$ | CH$_3$ |
| 3-CH$_2$CH=CH$_2$ | H | H | OCH$_3$ | CH$_3$ |
| 3-(CH$_2$)$_3$CH$_3$ | H | H | OCH$_3$ | CH$_3$ |
| 3-SO$_2$N(OCH$_3$)CH$_3$ | H | H | OCH$_3$ | CH$_3$ |
| 3-NO$_2$ | CH$_3$ | H | OCH$_3$ | CH$_3$ |
| 3-SO$_2$N(CH$_3$)$_2$ | CH$_3$ | H | OCH$_3$ | CH$_3$ |
| 3-Br | H | CH$_3$ | OCH$_3$ | CH$_3$ |
| 3-Cl | H | CH$_3$ | OCH$_3$ | CH$_3$ |
| 4-CH$_3$ | H | H | OCH$_3$ | CH$_3$ |
| 4-Cl | H | H | OCH$_3$ | CH$_3$ |
| 4-Br | H | H | OCH$_3$ | CH$_3$ |
| 4-NO$_2$ | H | H | OCH$_3$ | CH$_3$ |
| 4-SO$_2$N(CH$_3$)$_2$ | H | H | OCH$_3$ | CH$_3$ |
| 4-SO$_2$N(C$_2$H$_5$)$_2$ | H | H | OCH$_3$ | CH$_3$ |
| 4-SO$_2$N(CH$_3$)CH(CH$_3$)$_2$ | H | H | OCH$_3$ | CH$_3$ |
| 4-SO$_2$N(CH$_3$)CH$_2$CH$_2$CH$_3$ | H | H | OCH$_3$ | CH$_3$ |
| 4-OCH$_3$ | H | H | OCH$_3$ | CH$_3$ |
| 4-CH$_2$CH$_3$ | H | H | OCH$_3$ | CH$_3$ |
| 4-CH(CH$_3$)$_2$ | H | H | OCH$_3$ | CH$_3$ |
| 4-CH$_2$CH=CH$_2$ | H | H | OCH$_3$ | CH$_3$ |
| 4-(CH$_2$)$_3$CH$_3$ | H | H | OCH$_3$ | CH$_3$ |

TABLE IX-continued

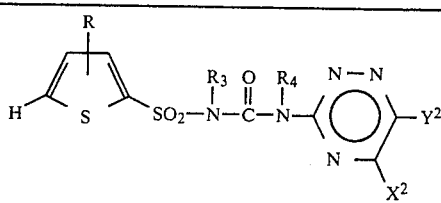

| R | $R_3$ | $R_4$ | $X^2$ | $Y^2$ |
|---|---|---|---|---|
| 4-SO$_2$N(OCH$_3$)CH$_3$ | H | H | OCH$_3$ | CH$_3$ |
| 4-NO$_2$ | CH$_3$ | H | OCH$_3$ | CH$_3$ |
| 4-SO$_2$N(CH$_3$)$_2$ | CH$_3$ | H | OCH$_3$ | CH$_3$ |
| 4-Br | H | CH$_3$ | OCH$_3$ | CH$_3$ |
| 4-Cl | H | CH$_3$ | OCH$_3$ | CH$_3$ |
| 3-CH$_3$ | H | H | CH$_3$ | OCH$_3$ |
| 3-Cl | H | H | CH$_3$ | OCH$_3$ |
| 3-Br | H | H | CH$_3$ | OCH$_3$ |
| 3-NO$_2$ | H | H | CH$_3$ | OCH$_3$ |
| 3-SO$_2$N(CH$_3$)$_2$ | H | H | CH$_3$ | OCH$_3$ |
| 3-SO$_2$N(C$_2$H$_5$)$_2$ | H | H | CH$_3$ | OCH$_3$ |
| 3-SO$_2$N(CH$_3$)CH(CH$_3$)$_2$ | H | H | CH$_3$ | OCH$_3$ |
| 3-SO$_2$N(CH$_3$)CH$_2$CH$_2$CH$_3$ | H | H | CH$_3$ | OCH$_3$ |
| 3-OCH$_3$ | H | H | CH$_3$ | OCH$_3$ |
| 3-CH$_2$CH$_3$ | H | H | CH$_3$ | OCH$_3$ |
| 3-CH(CH$_3$)$_2$ | H | H | CH$_3$ | OCH$_3$ |
| 3-CH$_2$CH(CH$_3$)$_2$ | H | H | CH$_3$ | OCH$_3$ |
| 3-CH$_2$CH=CH$_2$ | H | H | CH$_3$ | OCH$_3$ |
| 3-(CH$_2$)$_3$CH$_3$ | H | H | CH$_3$ | OCH$_3$ |
| 3-SO$_2$N(OCH$_3$)CH$_3$ | H | H | CH$_3$ | OCH$_3$ |
| 3-NO$_2$ | CH$_3$ | H | CH$_3$ | OCH$_3$ |
| 3-SO$_2$N(CH$_3$)$_2$ | CH$_3$ | H | CH$_3$ | OCH$_3$ |
| 3-Br | H | CH$_3$ | CH$_3$ | OCH$_3$ |
| 3-Cl | H | CH$_3$ | CH$_3$ | OCH$_3$ |
| 4-CH$_3$ | H | H | CH$_3$ | OCH$_3$ |
| 4-Cl | H | H | CH$_3$ | OCH$_3$ |
| 4-Br | H | H | CH$_3$ | OCH$_3$ |
| 4-NO$_2$ | H | H | CH$_3$ | OCH$_3$ |
| 4-SO$_2$N(CH$_3$)$_2$ | H | H | CH$_3$ | OCH$_3$ |
| 4-SO$_2$N(C$_2$H$_5$)$_2$ | H | H | CH$_3$ | OCH$_3$ |
| 4-SO$_2$N(CH$_3$)CH(CH$_3$)$_2$ | H | H | CH$_3$ | OCH$_3$ |
| 4-SO$_2$N(CH$_3$)CH$_2$CH$_2$CH$_3$ | H | H | CH$_3$ | OCH$_3$ |
| 4-OCH$_3$ | H | H | CH$_3$ | OCH$_3$ |
| 4-CH$_2$CH$_3$ | H | H | CH$_3$ | OCH$_3$ |
| 4-CH(CH$_3$)$_2$ | H | H | CH$_3$ | OCH$_3$ |
| 4-CH$_2$CH(CH$_3$)$_2$ | H | H | CH$_3$ | OCH$_3$ |
| 4-CH$_2$CH=CH$_2$ | H | H | CH$_3$ | OCH$_3$ |
| 4-(CH$_2$)$_3$CH$_3$ | H | H | CH$_3$ | OCH$_3$ |
| 4-SO$_2$N(OCH$_3$)CH$_3$ | H | H | CH$_3$ | OCH$_3$ |
| 4-NO$_2$ | CH$_3$ | H | CH$_3$ | OCH$_3$ |
| 4-SO$_2$N(CH$_3$)$_2$ | CH$_3$ | H | CH$_3$ | OCH$_3$ |
| 4-Br | H | CH$_3$ | CH$_3$ | OCH$_3$ |
| 4-Cl | H | CH$_3$ | CH$_3$ | OCH$_3$ |
| 3-CH$_3$ | H | H | OCH$_3$ | OCH$_3$ |
| 3-Cl | H | H | OCH$_3$ | OCH$_3$ |
| 3-Br | H | H | OCH$_3$ | OCH$_3$ |
| 3-NO$_2$ | H | H | OCH$_3$ | OCH$_3$ |
| 3-SO$_2$N(CH$_3$)$_2$ | H | H | OCH$_3$ | OCH$_3$ |
| 3-SO$_2$N(C$_2$H$_5$)$_2$ | H | H | OCH$_3$ | OCH$_3$ |
| 3-SO$_2$N(CH$_3$)CH(CH$_3$)$_2$ | H | H | OCH$_3$ | OCH$_3$ |
| 3-SO$_2$N(CH$_3$)CH$_2$CH$_2$CH$_3$ | H | H | OCH$_3$ | OCH$_3$ |
| 3-OCH$_3$ | H | H | OCH$_3$ | OCH$_3$ |
| 3-CH$_2$CH$_3$ | H | H | OCH$_3$ | OCH$_3$ |
| 3-CH(CH$_3$)$_2$ | H | H | OCH$_3$ | OCH$_3$ |
| 3-CH$_2$CH(CH$_3$)$_2$ | H | H | OCH$_3$ | OCH$_3$ |
| 3-CH$_2$CH=CH$_2$ | H | H | OCH$_3$ | OCH$_3$ |
| 3-(CH$_2$)$_3$CH$_3$ | H | H | OCH$_3$ | OCH$_3$ |
| 3-SO$_2$N(OCH$_3$)CH$_3$ | H | H | OCH$_3$ | OCH$_3$ |
| 3-NO$_2$ | CH$_3$ | H | OCH$_3$ | OCH$_3$ |
| 3-SO$_2$N(CH$_3$)$_2$ | CH$_3$ | H | OCH$_3$ | OCH$_3$ |
| 3-Br | H | CH$_3$ | OCH$_3$ | OCH$_3$ |
| 3-Cl | H | CH$_3$ | OCH$_3$ | OCH$_3$ |
| 4-CH$_3$ | H | H | OCH$_3$ | OCH$_3$ |
| 4-Cl | H | H | OCH$_3$ | OCH$_3$ |
| 4-Br | H | H | OCH$_3$ | OCH$_3$ |
| 4-NO$_2$ | H | H | OCH$_3$ | OCH$_3$ |
| 4-SO$_2$N(CH$_3$)$_2$ | H | H | OCH$_3$ | OCH$_3$ |
| 4-SO$_2$N(C$_2$H$_5$)$_2$ | H | H | OCH$_3$ | OCH$_3$ |
| 4-SO$_2$N(CH$_3$)CH(CH$_3$)$_2$ | H | H | OCH$_3$ | OCH$_3$ |
| 4-SO$_2$N(CH$_3$)CH$_2$CH$_2$CH$_3$ | H | H | OCH$_3$ | OCH$_3$ |
| 4-OCH$_3$ | H | H | OCH$_3$ | OCH$_3$ |

TABLE IX-continued

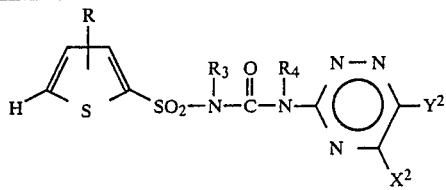

| R | R₃ | R₄ | X² | Y² |
|---|---|---|---|---|
| 4-CH₂CH₃ | H | H | OCH₃ | OCH₃ |
| 4-CH(CH₃)₂ | H | H | OCH₃ | OCH₃ |
| 4-CH₂CH(CH₃)₂ | H | H | OCH₃ | OCH₃ |
| 4-CH₂CH=CH₂ | H | H | OCH₃ | OCH₃ |
| 4-(CH₂)₃CH₃ | H | H | OCH₃ | OCH₃ |
| 4-SO₂N(OCH₃)CH₃ | H | H | OCH₃ | OCH₃ |
| 4-NO₂ | CH₃ | H | OCH₃ | OCH₃ |
| 4-SO₂N(CH₃)₂ | CH₃ | H | OCH₃ | OCH₃ |
| 4-Br | H | CH₃ | OCH₃ | OCH₃ |
| 4-Cl | H | CH₃ | OCH₃ | OCH₃ |

TABLE IX-a

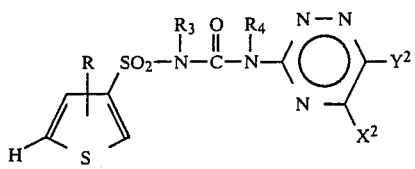

| R | R₃ | R₄ | X² | Y² |
|---|---|---|---|---|
| 2-NO₂ | H | H | CH₃ | CH₃ |
| 2-SO₂N(CH₃)₂ | H | H | CH₃ | CH₃ |
| 2-SO₂N(C₂H₅)₂ | H | H | CH₃ | CH₃ |
| 2-SO₂N(CH₃)CH(CH₃)₂ | H | H | CH₃ | CH₃ |
| 2-SO₂N(CH₃)CH₂CH₂CH₃ | H | H | CH₃ | CH₃ |
| 2-OCH₃ | H | H | CH₃ | CH₃ |
| 2-CH₂CH₃ | H | H | CH₃ | CH₃ |
| 2-CH(CH₃)₂ | H | H | CH₃ | CH₃ |
| 2-CH₂CH(CH₃)₂ | H | H | CH₃ | CH₃ |
| 2-CH₂CH=CH₂ | H | H | CH₃ | CH₃ |
| 2-(CH₂)₃CH₃ | H | H | CH₃ | CH₃ |
| 2-SO₂N(OCH₃)CH₃ | H | H | CH₃ | CH₃ |
| 2-NO₂ | CH₃ | H | CH₃ | CH₃ |
| 2-SO₂N(CH₃)₂ | CH₃ | H | CH₃ | CH₃ |
| 2-NO₂ | H | CH₃ | CH₃ | CH₃ |
| 2-SO₂N(CH₃)₂ | H | CH₃ | CH₃ | CH₃ |
| 4-CH₃ | H | H | CH₃ | CH₃ |
| 4-Cl | H | H | CH₃ | CH₃ |
| 4-Br | H | H | CH₃ | CH₃ |
| 4-NO₂ | H | H | CH₃ | CH₃ |
| 4-SO₂N(CH₃)₂ | H | H | CH₃ | CH₃ |
| 4-SO₂N(C₂H₅)₂ | H | H | CH₃ | CH₃ |
| 4-SO₂N(CH₃)CH(CH₃)₂ | H | H | CH₃ | CH₃ |
| 4-SO₂N(CH₃)CH₂CH₂CH₃ | H | H | CH₃ | CH₃ |
| 4-OCH₃ | H | H | CH₃ | CH₃ |
| 4-CH₂CH₃ | H | H | CH₃ | CH₃ |
| 4-CH(CH₃)₂ | H | H | CH₃ | CH₃ |
| 4-CH₂CH(CH₃)₂ | H | H | CH₃ | CH₃ |
| 4-CH₂CH=CH₂ | H | H | CH₃ | CH₃ |
| 4-(CH₂)₃CH₃ | H | H | CH₃ | CH₃ |
| 4-SO₂N(OCH₃)CH₃ | H | H | CH₃ | CH₃ |
| 4-NO₂ | CH₃ | H | CH₃ | CH₃ |
| 4-SO₂N(CH₃)₂ | CH₃ | H | CH₃ | CH₃ |
| 4-Br | H | CH₃ | CH₃ | CH₃ |
| 4-Cl | H | CH₃ | CH₃ | CH₃ |
| 2-NO₂ | H | H | OCH₃ | CH₃ |
| 2-SO₂N(CH₃)₂ | H | H | OCH₃ | CH₃ |
| 2-SO₂N(C₂H₅)₂ | H | H | OCH₃ | CH₃ |
| 2-SO₂N(CH₃)CH(CH₃)₂ | H | H | OCH₃ | CH₃ |
| 2-SO₂N(CH₃)CH₂CH₂CH₃ | H | H | OCH₃ | CH₃ |
| 2-OCH₃ | H | H | OCH₃ | CH₃ |
| 2-CH₂CH₃ | H | H | OCH₃ | CH₃ |
| 2-CH(CH₃)₂ | H | H | OCH₃ | CH₃ |
| 2-CH₂CH(CH₃)₂ | H | H | OCH₃ | CH₃ |
| 2-CH₂CH=CH₂ | H | H | OCH₃ | CH₃ |
| 2-(CH₂)₃CH₃ | H | H | OCH₃ | CH₃ |
| 2-SO₂N(OCH₃)CH₃ | H | H | OCH₃ | CH₃ |

TABLE IX-a-continued

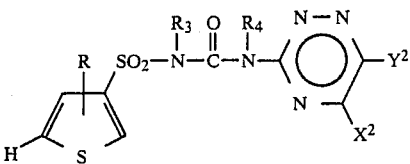

| R | R₃ | R₄ | X² | Y² |
|---|---|---|---|---|
| 2-NO₂ | CH₃ | H | OCH₃ | CH₃ |
| 2-SO₂N(CH₃)₂ | CH₃ | H | OCH₃ | CH₃ |
| 2-NO₂ | H | CH₃ | OCH₃ | CH₃ |
| 2-SO₂N(CH₃)₂ | H | CH₃ | OCH₃ | CH₃ |
| 4-CH₃ | H | H | OCH₃ | CH₃ |
| 4-Cl | H | H | OCH₃ | CH₃ |
| 4-Br | H | H | OCH₃ | CH₃ |
| 4-NO₂ | H | H | OCH₃ | CH₃ |
| 4-SO₂N(CH₃)₂ | H | H | OCH₃ | CH₃ |
| 4-SO₂N(C₂H₅)₂ | H | H | OCH₃ | CH₃ |
| 4-SO₂N(CH₃)CH(CH₃)₂ | H | H | OCH₃ | CH₃ |
| 4-SO₂N(CH₃)CH₂CH₂CH₃ | H | H | OCH₃ | CH₃ |
| 4-OCH₃ | H | H | OCH₃ | CH₃ |
| 4-CH₂CH₃ | H | H | OCH₃ | CH₃ |
| 4-CH(CH₃)₂ | H | H | OCH₃ | CH₃ |
| 4-CH₂CH(CH₃)₂ | H | H | OCH₃ | CH₃ |
| 4-CH₂CH=CH₂ | H | H | OCH₃ | CH₃ |
| 4-(CH₂)₃CH₃ | H | H | OCH₃ | CH₃ |
| 4-SO₂N(OCH₃)CH₃ | H | H | OCH₃ | CH₃ |
| 4-NO₂ | CH₃ | H | OCH₃ | CH₃ |
| 4-SO₂N(CH₃)₂ | CH₃ | H | OCH₃ | CH₃ |
| 4-Br | H | CH₃ | OCH₃ | CH₃ |
| 4-Cl | H | CH₃ | OCH₃ | CH₃ |
| 2-NO₂ | H | H | CH₃ | OCH₃ |
| 2-SO₂N(CH₃)₂ | H | H | CH₃ | OCH₃ |
| 2-SO₂N(C₂H₅)₂ | H | H | CH₃ | OCH₃ |
| 2-SO₂N(CH₃)CH(CH₃)₂ | H | H | CH₃ | OCH₃ |
| 2-SO₂N(CH₃)CH₂CH₂CH₃ | H | H | CH₃ | OCH₃ |
| 2-OCH₃ | H | H | CH₃ | OCH₃ |
| 2-CH₂CH₃ | H | H | CH₃ | OCH₃ |
| 2-CH(CH₃)₂ | H | H | CH₃ | OCH₃ |
| 2-CH₂CH(CH₃)₂ | H | H | CH₃ | OCH₃ |
| 2-CH₂CH=CH₂ | H | H | CH₃ | OCH₃ |
| 2-(CH₂)₃CH₃ | H | H | CH₃ | OCH₃ |
| 2-SO₂N(OCH₃)CH₃ | H | H | CH₃ | OCH₃ |
| 2-NO₂ | CH₃ | H | CH₃ | OCH₃ |
| 2-SO₂N(CH₃)₂ | CH₃ | H | CH₃ | OCH₃ |
| 2-NO₂ | H | CH₃ | CH₃ | OCH₃ |
| 2-SO₂N(CH₃)₂ | H | CH₃ | CH₃ | OCH₃ |
| 4-CH₃ | H | H | CH₃ | OCH₃ |
| 4-Cl | H | H | CH₃ | OCH₃ |
| 4-Br | H | H | CH₃ | OCH₃ |
| 4-NO₂ | H | H | CH₃ | OCH₃ |
| 4-SO₂N(CH₃)₂ | H | H | CH₃ | OCH₃ |
| 4-SO₂N(C₂H₅)₂ | H | H | CH₃ | OCH₃ |
| 4-SO₂N(CH₃)CH(CH₃)₂ | H | H | CH₃ | OCH₃ |
| 4-SO₂N(CH₃)CH₂CH₂CH₃ | H | H | CH₃ | OCH₃ |
| 4-OCH₃ | H | H | CH₃ | OCH₃ |
| 4-CH₂CH₃ | H | H | CH₃ | OCH₃ |
| 4-CH(CH₃)₂ | H | H | CH₃ | OCH₃ |
| 4-CH₂CH(CH₃)₂ | H | H | CH₃ | OCH₃ |
| 4-CH₂CH=CH₂ | H | H | CH₃ | OCH₃ |
| 4-(CH₂)₃CH₃ | H | H | CH₃ | OCH₃ |
| 4-SO₂N(OCH₃)CH₃ | H | H | CH₃ | OCH₃ |
| 4-NO₂ | CH₃ | H | CH₃ | OCH₃ |
| 4-SO₂N(CH₃)₂ | CH₃ | H | CH₃ | OCH₃ |
| 4-Br | H | CH₃ | CH₃ | OCH₃ |
| 4-Cl | H | CH₃ | CH₃ | OCH₃ |
| 2-NO₂ | H | H | OCH₃ | OCH₃ |
| 2-SO₂N(C₂H₅)₂ | H | H | OCH₃ | OCH₃ |
| 2-SO₂N(CH₃)CH(CH₃)₂ | H | H | OCH₃ | OCH₃ |
| 2-SO₂N(CH₃)CH₂CH₂CH₃ | H | H | OCH₃ | OCH₃ |
| 2-OCH₃ | H | H | OCH₃ | OCH₃ |
| 2-CH₂CH₃ | H | H | OCH₃ | OCH₃ |
| 2-CH(CH₃)₂ | H | H | OCH₃ | OCH₃ |
| 2-CH₂CH(CH₃)₂ | H | H | OCH₃ | OCH₃ |
| 2-CH₂CH=CH₂ | H | H | OCH₃ | OCH₃ |
| 2-(CH₂)₃CH₃ | H | H | OCH₃ | OCH₃ |
| 2-SO₂N(OCH₃)CH₃ | H | H | OCH₃ | OCH₃ |
| 2-NO₂ | CH₃ | H | OCH₃ | OCH₃ |
| 2-SO₂N(CH₃)₂ | CH₃ | H | OCH₃ | OCH₃ |

TABLE IX-a-continued

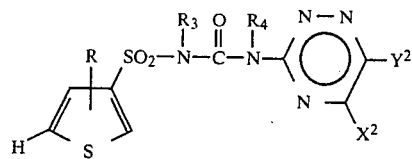

| R | R₃ | R₄ | X² | Y² |
|---|---|---|---|---|
| 2-NO₂ | H | CH₃ | OCH₃ | OCH₃ |
| 2-SO₂N(CH₃)₂ | H | CH₃ | OCH₃ | OCH₃ |
| 4-CH₃ | H | H | OCH₃ | OCH₃ |
| 4-Cl | H | H | OCH₃ | OCH₃ |
| 4-Br | H | H | OCH₃ | OCH₃ |
| 4-NO₂ | H | H | OCH₃ | OCH₃ |
| 4-SO₂N(CH₃)₂ | H | H | OCH₃ | OCH₃ |
| 4-SO₂N(C₂H₅)₂ | H | H | OCH₃ | OCH₃ |
| 4-SO₂N(CH₃)CH(CH₃)₂ | H | H | OCH₃ | OCH₃ |
| 4-SO₂N(CH₃)CH₂CH₂CH₃ | H | H | OCH₃ | OCH₃ |
| 4-OCH₃ | H | H | OCH₃ | OCH₃ |
| 4-CH₂CH₃ | H | H | OCH₃ | OCH₃ |
| 4-CH(CH₃)₂ | H | H | OCH₃ | OCH₃ |
| 4-CH₂CH(CH₃)₂ | H | H | OCH₃ | OCH₃ |
| 4-CH₂CH=CH₂ | H | H | OCH₃ | OCH₃ |
| 4-(CH₂)₃CH₃ | H | H | OCH₃ | OCH₃ |
| 4-SO₂N(OCH₃)CH₃ | H | H | OCH₃ | OCH₃ |
| 4-NO₂ | CH₃ | H | OCH₃ | OCH₃ |
| 4-SO₂N(CH₃)₂ | CH₃ | H | OCH₃ | OCH₃ |
| 4-Br | H | CH₃ | OCH₃ | OCH₃ |
| 4-Cl | H | CH₃ | OCH₃ | OCH₃ |

TABLE X

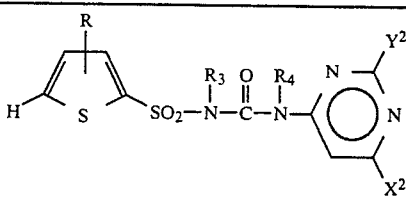

| R | R₃ | R₄ | X² | Y² |
|---|---|---|---|---|
| 3-CH₃ | H | H | CH₃ | CH₃ |
| 3-Cl | H | H | CH₃ | CH₃ |
| 3-Br | H | H | CH₃ | CH₃ |
| 3-NO₂ | H | H | CH₃ | CH₃ |
| 3-SO₂N(CH₃)₂ | H | H | CH₃ | CH₃ |
| 3-SO₂N(C₂H₅)₂ | H | H | CH₃ | CH₃ |
| 3-SO₂N(CH₃)CH(CH₃)₂ | H | H | CH₃ | CH₃ |
| 3-SO₂N(CH₃)CH₂CH₂CH₃ | H | H | CH₃ | CH₃ |
| 3-OCH₃ | H | H | CH₃ | CH₃ |
| 3-CH₂CH₃ | H | H | CH₃ | CH₃ |
| 3-CH(CH₃)₂ | H | H | CH₃ | CH₃ |
| 3-CH₂CH(CH₃)₂ | H | H | CH₃ | CH₃ |
| 3-CH₂CH=CH₂ | H | H | CH₃ | CH₃ |
| 3-(CH₂)₃CH₃ | H | H | CH₃ | CH₃ |
| 3-SO₂N(OCH₃)CH₃ | H | H | CH₃ | CH₃ |
| 3-NO₂ | CH₃ | H | CH₃ | CH₃ |
| 3-SO₂N(CH₃)₂ | CH₃ | H | CH₃ | CH₃ |
| 3-Br | H | CH₃ | CH₃ | CH₃ |
| 3-Cl | H | CH₃ | CH₃ | CH₃ |
| 4-CH₃ | H | H | CH₃ | CH₃ |
| 4-Cl | H | H | CH₃ | CH₃ |
| 4-Br | H | H | CH₃ | CH₃ |
| 4-NO₂ | H | H | CH₃ | CH₃ |
| 4-SO₂N(CH₃)₂ | H | H | CH₃ | CH₃ |
| 4-SO₂N(C₂H₅)₂ | H | H | CH₃ | CH₃ |
| 4-SO₂N(CH₃)CH(CH₃)₂ | H | H | CH₃ | CH₃ |
| 4-SO₂N(CH₃)CH₂CH₂CH₃ | H | H | CH₃ | CH₃ |
| 4-OCH₃ | H | H | CH₃ | CH₃ |
| 4-CH₂CH₃ | H | H | CH₃ | CH₃ |
| 4-CH(CH₃)₂ | H | H | CH₃ | CH₃ |
| 4-CH₂CH(CH₃)₂ | H | H | CH₃ | CH₃ |
| 4-CH₂CH=CH₂ | H | H | CH₃ | CH₃ |
| 4-(CH₂)₃CH₃ | H | H | CH₃ | CH₃ |
| 4-SO₂N(OCH₃)CH₃ | H | H | CH₃ | CH₃ |
| 4-NO₂ | CH₃ | H | CH₃ | CH₃ |
| 4-SO₂N(CH₃)₂ | CH₃ | H | CH₃ | CH₃ |

TABLE X-continued

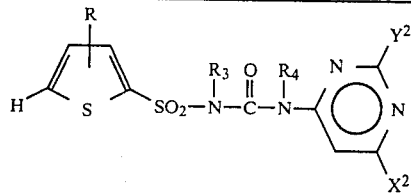

| R | R₃ | R₄ | X² | Y² |
|---|---|---|---|---|
| 4-Br | H | CH₃ | CH₃ | CH₃ |
| 4-Cl | H | CH₃ | CH₃ | CH₃ |
| 3-CH₃ | H | H | OCH₃ | CH₃ |
| 3-Cl | H | H | OCH₃ | CH₃ |
| 3-Br | H | H | OCH₃ | CH₃ |
| 3-NO₂ | H | H | OCH₃ | CH₃ |
| 3-SO₂N(CH₃)₂ | H | H | OCH₃ | CH₃ |
| 3-SO₂N(C₂H₅)₂ | H | H | OCH₃ | CH₃ |
| 3-SO₂N(CH₃)CH(CH₃)₂ | H | H | OCH₃ | CH₃ |
| 3-SO₂N(CH₃)CH₂CH₂CH₃ | H | H | OCH₃ | CH₃ |
| 3-OCH₃ | H | H | OCH₃ | CH₃ |
| 3-CH₂CH₃ | H | H | OCH₃ | CH₃ |
| 3-CH(CH₃)₂ | H | H | OCH₃ | CH₃ |
| 3-CH₂CH(CH₃)₂ | H | H | OCH₃ | CH₃ |
| 3-CH₂CH=CH₂ | H | H | OCH₃ | CH₃ |
| 3-(CH₂)₃CH₃ | H | H | OCH₃ | CH₃ |
| 3-SO₂N(OCH₃)CH₃ | H | H | OCH₃ | CH₃ |
| 3-NO₂ | CH₃ | H | OCH₃ | CH₃ |
| 3-SO₂N(CH₃)₂ | CH₃ | H | OCH₃ | CH₃ |
| 3-Br | H | CH₃ | OCH₃ | CH₃ |
| 3-Cl | H | CH₃ | OCH₃ | CH₃ |
| 4-CH₃ | H | H | OCH₃ | CH₃ |
| 4-Cl | H | H | OCH₃ | CH₃ |
| 4-Br | H | H | OCH₃ | CH₃ |
| 4-NO₂ | H | H | OCH₃ | CH₃ |
| 4-SO₂N(CH₃)₂ | H | H | OCH₃ | CH₃ |
| 4-SO₂N(C₂H₅)₂ | H | H | OCH₃ | CH₃ |
| 4-SO₂N(CH₃)CH(CH₃)₂ | H | H | OCH₃ | CH₃ |
| 4-SO₂N(CH₃)CH₂CH₂CH₃ | H | H | OCH₃ | CH₃ |
| 4-OCH₃ | H | H | OCH₃ | CH₃ |
| 4-CH₂CH₃ | H | H | OCH₃ | CH₃ |
| 4-CH(CH₃)₂ | H | H | OCH₃ | CH₃ |
| 4-CH₂CH=CH₂ | H | H | OCH₃ | CH₃ |
| 4-(CH₂)₃CH₃ | H | H | OCH₃ | CH₃ |
| 4-SO₂N(OCH₃)CH₃ | H | H | OCH₃ | CH₃ |
| 4-NO₂ | CH₃ | H | OCH₃ | CH₃ |
| 4-SO₂N(CH₃)₂ | CH₃ | H | OCH₃ | CH₃ |
| 4-Br | H | CH₃ | OCH₃ | CH₃ |
| 4-Cl | H | CH₃ | OCH₃ | CH₃ |
| 3-CH₃ | H | H | CH₃ | OCH₃ |
| 3-Cl | H | H | CH₃ | OCH₃ |
| 3-Br | H | H | CH₃ | OCH₃ |
| 3-NO₂ | H | H | CH₃ | OCH₃ |
| 3-SO₂N(CH₃)₂ | H | H | CH₃ | OCH₃ |
| 3-SO₂N(C₂H₅)₂ | H | H | CH₃ | OCH₃ |
| 3-SO₂N(CH₃)CH(CH₃)₂ | H | H | CH₃ | OCH₃ |
| 3-SO₂N(CH₃)CH₂CH₂CH₃ | H | H | CH₃ | OCH₃ |
| 3-OCH₃ | H | H | CH₃ | OCH₃ |
| 3-CH₂CH₃ | H | H | CH₃ | OCH₃ |
| 3-CH(CH₃)₂ | H | H | CH₃ | OCH₃ |
| 3-CH₂CH(CH₃)₂ | H | H | CH₃ | OCH₃ |
| 3-CH₂CH=CH₂ | H | H | CH₃ | OCH₃ |
| 3-(CH₂)₃CH₃ | H | H | CH₃ | OCH₃ |
| 3-SO₂N(OCH₃)CH₃ | H | H | CH₃ | OCH₃ |
| 3-NO₂ | CH₃ | H | CH₃ | OCH₃ |
| 3-SO₂N(CH₃)₂ | CH₃ | H | CH₃ | OCH₃ |
| 3-Br | H | CH₃ | CH₃ | OCH₃ |
| 3-Cl | H | CH₃ | CH₃ | OCH₃ |
| 4-CH₃ | H | H | CH₃ | OCH₃ |
| 4-Cl | H | H | CH₃ | OCH₃ |
| 4-Br | H | H | CH₃ | OCH₃ |
| 4-NO₂ | H | H | CH₃ | OCH₃ |
| 4-SO₂N(CH₃)₂ | H | H | CH₃ | OCH₃ |
| 4-SO₂N(C₂H₅)₂ | H | H | CH₃ | OCH₃ |
| 4-SO₂N(CH₃)CH(CH₃)₂ | H | H | CH₃ | OCH₃ |
| 4-SO₂N(CH₃)CH₂CH₂CH₃ | H | H | CH₃ | OCH₃ |
| 4-OCH₃ | H | H | CH₃ | OCH₃ |
| 4-CH₂CH₃ | H | H | CH₃ | OCH₃ |
| 4-CH(CH₃)₂ | H | H | CH₃ | OCH₃ |
| 4-CH₂CH(CH₃)₂ | H | H | CH₃ | OCH₃ |

TABLE X-continued

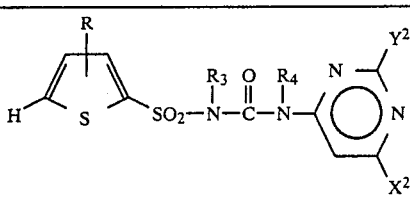

| R | $R_3$ | $R_4$ | $X^2$ | $Y^2$ |
|---|---|---|---|---|
| 4-CH$_2$CH=CH$_2$ | H | H | CH$_3$ | OCH$_3$ |
| 4-(CH$_2$)$_3$CH$_3$ | H | H | CH$_3$ | OCH$_3$ |
| 4-SO$_2$N(OCH$_3$)CH$_3$ | H | H | CH$_3$ | OCH$_3$ |
| 4-NO$_2$ | CH$_3$ | H | CH$_3$ | OCH$_3$ |
| 4-SO$_2$N(CH$_3$)$_2$ | CH$_3$ | H | CH$_3$ | OCH$_3$ |
| 4-Br | H | CH$_3$ | CH$_3$ | OCH$_3$ |
| 4-Cl | H | CH$_3$ | CH$_3$ | OCH$_3$ |
| 3-CH$_3$ | H | H | OCH$_3$ | OCH$_3$ |
| 3-Cl | H | H | OCH$_3$ | OCH$_3$ |
| 3-Br | H | H | OCH$_3$ | OCH$_3$ |
| 3-NO$_2$ | H | H | OCH$_3$ | OCH$_3$ |
| 3-SO$_2$N(CH$_3$)$_2$ | H | H | OCH$_3$ | OCH$_3$ |
| 3-SO$_2$N(C$_2$H$_5$)$_2$ | H | H | OCH$_3$ | OCH$_3$ |
| 3-SO$_2$N(CH$_3$)CH(CH$_3$)$_2$ | H | H | OCH$_3$ | OCH$_3$ |
| 3-SO$_2$N(CH$_3$)CH$_2$CH$_2$CH$_3$ | H | H | OCH$_3$ | OCH$_3$ |
| 3-OCH$_3$ | H | H | OCH$_3$ | OCH$_3$ |
| 3-CH$_2$CH$_3$ | H | H | OCH$_3$ | OCH$_3$ |
| 3-CH(CH$_3$)$_2$ | H | H | OCH$_3$ | OCH$_3$ |
| 3-CH$_2$CH(CH$_3$)$_2$ | H | H | OCH$_3$ | OCH$_3$ |
| 3-CH$_2$CH=CH$_2$ | H | H | OCH$_3$ | OCH$_3$ |
| 3-(CH$_2$)$_3$CH$_3$ | H | H | OCH$_3$ | OCH$_3$ |
| 3-SO$_2$N(OCH$_3$)CH$_3$ | H | H | OCH$_3$ | OCH$_3$ |
| 3-NO$_2$ | CH$_3$ | H | OCH$_3$ | OCH$_3$ |
| 3-SO$_2$N(CH$_3$)$_2$ | CH$_3$ | H | OCH$_3$ | OCH$_3$ |
| 3-Br | H | CH$_3$ | OCH$_3$ | OCH$_3$ |
| 3-Cl | H | CH$_3$ | OCH$_3$ | OCH$_3$ |
| 4-CH$_3$ | H | H | OCH$_3$ | OCH$_3$ |
| 4-Cl | H | H | OCH$_3$ | OCH$_3$ |
| 4-Br | H | H | OCH$_3$ | OCH$_3$ |
| 4-NO$_2$ | H | H | OCH$_3$ | OCH$_3$ |
| 4-SO$_2$N(CH$_3$)$_2$ | H | H | OCH$_3$ | OCH$_3$ |
| 4-SO$_2$N(C$_2$H$_5$)$_2$ | H | H | OCH$_3$ | OCH$_3$ |
| 4-SO$_2$N(CH$_3$)CH(CH$_3$)$_2$ | H | H | OCH$_3$ | OCH$_3$ |
| 4-SO$_2$N(CH$_3$)CH$_2$CH$_2$CH$_3$ | H | H | OCH$_3$ | OCH$_3$ |
| 4-OCH$_3$ | H | H | OCH$_3$ | OCH$_3$ |
| 4-CH$_2$CH$_3$ | H | H | OCH$_3$ | OCH$_3$ |
| 4-CH(CH$_3$)$_2$ | H | H | OCH$_3$ | OCH$_3$ |
| 4-CH$_2$CH(CH$_3$)$_2$ | H | H | OCH$_3$ | OCH$_3$ |
| 4-CH$_2$CH=CH$_2$ | H | H | OCH$_3$ | OCH$_3$ |
| 4-(CH$_2$)$_3$CH$_3$ | H | H | OCH$_3$ | OCH$_3$ |
| 4-SO$_2$N(OCH$_3$)CH$_3$ | H | H | OCH$_3$ | OCH$_3$ |
| 4-NO$_2$ | CH$_3$ | H | OCH$_3$ | OCH$_3$ |
| 4-SO$_2$N(CH$_3$)$_2$ | CH$_3$ | H | OCH$_3$ | OCH$_3$ |
| 4-Br | H | CH$_3$ | OCH$_3$ | OCH$_3$ |
| 4-Cl | H | CH$_3$ | OCH$_3$ | OCH$_3$ |

TABLE X-a

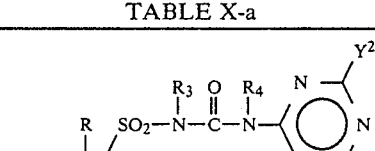

| R | $R_3$ | $R_4$ | $X^2$ | $Y^2$ |
|---|---|---|---|---|
| 2-CH$_3$ | H | H | CH$_3$ | CH$_3$ |
| 2-Cl | H | H | CH$_3$ | CH$_3$ |
| 2-Br | H | H | CH$_3$ | CH$_3$ |
| 2-NO$_2$ | H | H | CH$_3$ | CH$_3$ |
| 2-SO$_2$N(CH$_3$)$_2$ | H | H | CH$_3$ | CH$_3$ |
| 2-SO$_2$N(C$_2$H$_5$)$_2$ | H | H | CH$_3$ | CH$_3$ |
| 2-SO$_2$N(CH$_3$)CH(CH$_3$)$_2$ | H | H | CH$_3$ | CH$_3$ |
| 2-SO$_2$N(CH$_3$)CH$_2$CH$_2$CH$_3$ | H | H | CH$_3$ | CH$_3$ |
| 2-OCH$_3$ | H | H | CH$_3$ | CH$_3$ |
| 2-CH$_2$CH$_3$ | H | H | CH$_3$ | CH$_3$ |

TABLE X-a-continued

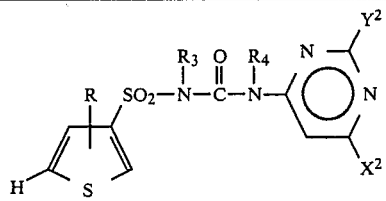

| R | $R_3$ | $R_4$ | $X^2$ | $Y^2$ |
|---|---|---|---|---|
| 2-CH(CH$_3$)$_2$ | H | H | CH$_3$ | CH$_3$ |
| 2-CH$_2$CH(CH$_3$)$_2$ | H | H | CH$_3$ | CH$_3$ |
| 2-CH$_2$CH=CH$_2$ | H | H | CH$_3$ | CH$_3$ |
| 2-(CH$_2$)$_3$CH$_3$ | H | H | CH$_3$ | CH$_3$ |
| 2-SO$_2$N(OCH$_3$)CH$_3$ | H | H | CH$_3$ | CH$_3$ |
| 2-NO$_2$ | CH$_3$ | H | CH$_3$ | CH$_3$ |
| 2-SO$_2$N(CH$_3$)$_2$ | CH$_3$ | H | CH$_3$ | CH$_3$ |
| 2-Br | H | CH$_3$ | CH$_3$ | CH$_3$ |
| 2-Cl | H | CH$_3$ | CH$_3$ | CH$_3$ |
| 4-CH$_3$ | H | H | CH$_3$ | CH$_3$ |
| 4-Cl | H | H | CH$_3$ | CH$_3$ |
| 4-Br | H | H | CH$_3$ | CH$_3$ |
| 4-NO$_2$ | H | H | CH$_3$ | CH$_3$ |
| 4-SO$_2$N(CH$_3$)$_2$ | H | H | CH$_3$ | CH$_3$ |
| 4-SO$_2$N(C$_2$H$_5$)$_2$ | H | H | CH$_3$ | CH$_3$ |
| 4-SO$_2$N(CH$_3$)CH(CH$_3$)$_2$ | H | H | CH$_3$ | CH$_3$ |
| 4-SO$_2$N(CH$_3$)CH$_2$CH$_2$CH$_3$ | H | H | CH$_3$ | CH$_3$ |
| 4-OCH$_3$ | H | H | CH$_3$ | CH$_3$ |
| 4-CH$_2$CH$_3$ | H | H | CH$_3$ | CH$_3$ |
| 4-CH(CH$_3$)$_2$ | H | H | CH$_3$ | CH$_3$ |
| 4-CH$_2$CH(CH$_3$)$_2$ | H | H | CH$_3$ | CH$_3$ |
| 4-CH$_2$CH=CH$_2$ | H | H | CH$_3$ | CH$_3$ |
| 4-(CH$_2$)$_3$CH$_3$ | H | H | CH$_3$ | CH$_3$ |
| 4-SO$_2$N(OCH$_3$)CH$_3$ | H | H | CH$_3$ | CH$_3$ |
| 4-NO$_2$ | CH$_3$ | H | CH$_3$ | CH$_3$ |
| 4-SO$_2$N(CH$_3$)$_2$ | CH$_3$ | H | CH$_3$ | CH$_3$ |
| 4-Br | H | CH$_3$ | CH$_3$ | CH$_3$ |
| 4-Cl | H | CH$_3$ | CH$_3$ | CH$_3$ |
| 2-CH$_3$ | H | H | OCH$_3$ | CH$_3$ |
| 2-Cl | H | H | OCH$_3$ | CH$_3$ |
| 2-Br | H | H | OCH$_3$ | CH$_3$ |
| 2-NO$_2$ | H | H | OCH$_3$ | CH$_3$ |
| 2-SO$_2$N(CH$_3$)$_2$ | H | H | OCH$_3$ | CH$_3$ |
| 2-SO$_2$N(C$_2$H$_5$)$_2$ | H | H | OCH$_3$ | CH$_3$ |
| 2-SO$_2$N(CH$_3$)CH(CH$_3$)$_2$ | H | H | OCH$_3$ | CH$_3$ |
| 2-SO$_2$N(CH$_3$)CH$_2$CH$_2$CH$_3$ | H | H | OCH$_3$ | CH$_3$ |
| 2-OCH$_3$ | H | H | OCH$_3$ | CH$_3$ |
| 2-CH$_2$CH$_3$ | H | H | OCH$_3$ | CH$_3$ |
| 2-CH(CH$_3$)$_2$ | H | H | OCH$_3$ | CH$_3$ |
| 2-CH$_2$CH(CH$_3$)$_2$ | H | H | OCH$_3$ | CH$_3$ |
| 2-CH$_2$CH=CH$_2$ | H | H | OCH$_3$ | CH$_3$ |
| 2-(CH$_2$)$_3$CH$_3$ | H | H | OCH$_3$ | CH$_3$ |
| 2-SO$_2$N(OCH$_3$)CH$_3$ | H | H | OCH$_3$ | CH$_3$ |
| 2-NO$_2$ | CH$_3$ | H | OCH$_3$ | CH$_3$ |
| 2-SO$_2$N(CH$_3$)$_2$ | CH$_3$ | H | OCH$_3$ | CH$_3$ |
| 2-Br | H | CH$_3$ | OCH$_3$ | CH$_3$ |
| 2-Cl | H | CH$_3$ | OCH$_3$ | CH$_3$ |
| 4-CH$_3$ | H | H | OCH$_3$ | CH$_3$ |
| 4-Cl | H | H | OCH$_3$ | CH$_3$ |
| 4-Br | H | H | OCH$_3$ | CH$_3$ |
| 4-NO$_2$ | H | H | OCH$_3$ | CH$_3$ |
| 4-SO$_2$N(CH$_3$)$_2$ | H | H | OCH$_3$ | CH$_3$ |
| 4-SO$_2$N(C$_2$H$_5$)$_2$ | H | H | OCH$_3$ | CH$_3$ |
| 4-SO$_2$N(CH$_3$)CH(CH$_3$)$_2$ | H | H | OCH$_3$ | CH$_3$ |
| 4-SO$_2$N(CH$_3$)CH$_2$CH$_2$CH$_3$ | H | H | OCH$_3$ | CH$_3$ |
| 4-OCH$_3$ | H | H | OCH$_3$ | CH$_3$ |
| 4-CH$_2$CH$_3$ | H | H | OCH$_3$ | CH$_3$ |
| 4-CH(CH$_3$)$_2$ | H | H | OCH$_3$ | CH$_3$ |
| 4-CH$_2$CH(CH$_3$)$_2$ | H | H | OCH$_3$ | CH$_3$ |
| 4-CH$_2$CH=CH$_2$ | H | H | OCH$_3$ | CH$_3$ |
| 4-(CH$_2$)$_3$CH$_3$ | H | H | OCH$_3$ | CH$_3$ |
| 4-SO$_2$N(OCH$_3$)CH$_3$ | H | H | OCH$_3$ | CH$_3$ |
| 4-NO$_2$ | CH$_3$ | H | OCH$_3$ | CH$_3$ |
| 4-SO$_2$N(CH$_3$)$_2$ | CH$_3$ | H | OCH$_3$ | CH$_3$ |
| 4-Br | H | CH$_3$ | OCH$_3$ | CH$_3$ |
| 4-Cl | H | CH$_3$ | OCH$_3$ | CH$_3$ |
| 2-CH$_3$ | H | H | CH$_3$ | OCH$_3$ |
| 2-Cl | H | H | CH$_3$ | OCH$_3$ |
| 2-Br | H | H | CH$_3$ | OCH$_3$ |
| 2-NO$_2$ | H | H | CH$_3$ | OCH$_3$ |
| 2-SO$_2$N(CH$_3$)$_2$ | H | H | CH$_3$ | OCH$_3$ |

TABLE X-a-continued $$R\text{-}SO_2\text{-}N(R_3)\text{-}C(O)\text{-}N(R_4)\text{-}\text{[pyrimidine with }X^2, Y^2\text{]}$$

(thiophene ring with H at position 5, SO₂ at R)

| R | $R_3$ | $R_4$ | $X^2$ | $Y^2$ |
|---|---|---|---|---|
| 2-SO₂N(C₂H₅)₂ | H | H | CH₃ | OCH₃ |
| 2-SO₂N(CH₃)CH(CH₃)₂ | H | H | CH₃ | OCH₃ |
| 2-SO₂N(CH₃)CH₂CH₂CH₃ | H | H | CH₃ | OCH₃ |
| 2-OCH₃ | H | H | CH₃ | OCH₃ |
| 2-CH₂CH₃ | H | H | CH₃ | OCH₃ |
| 2-CH(CH₃)₂ | H | H | CH₃ | OCH₃ |
| 2-CH₂CH(CH₃)₂ | H | H | CH₃ | OCH₃ |
| 2-CH₂CH=CH₂ | H | H | CH₃ | OCH₃ |
| 2-(CH₂)₃CH₃ | H | H | CH₃ | OCH₃ |
| 2-SO₂N(OCH₃)CH₃ | H | H | CH₃ | OCH₃ |
| 2-NO₂ | CH₃ | H | CH₃ | OCH₃ |
| 2-SO₂N(CH₃)₂ | CH₃ | H | CH₃ | OCH₃ |
| 2-Br | H | CH₃ | CH₃ | OCH₃ |
| 2-Cl | H | CH₃ | CH₃ | OCH₃ |
| 4-CH₃ | H | H | CH₃ | OCH₃ |
| 4-Cl | H | H | CH₃ | OCH₃ |
| 4-Br | H | H | CH₃ | OCH₃ |
| 4-NO₂ | H | H | CH₃ | OCH₃ |
| 4-SO₂N(CH₃)₂ | H | H | CH₃ | OCH₃ |
| 4-SO₂N(C₂H₅)₂ | H | H | CH₃ | OCH₃ |
| 4-SO₂N(CH₃)CH(CH₃)₂ | H | H | CH₃ | OCH₃ |
| 4-SO₂N(CH₃)CH₂CH₂CH₃ | H | H | CH₃ | OCH₃ |
| 4-OCH₃ | H | H | CH₃ | OCH₃ |
| 4-CH₂CH₃ | H | H | CH₃ | OCH₃ |
| 4-CH(CH₃)₂ | H | H | CH₃ | OCH₃ |
| 4-CH₂CH(CH₃)₂ | H | H | CH₃ | OCH₃ |
| 4-CH₂CH=CH₂ | H | H | CH₃ | OCH₃ |
| 4-(CH₂)₃CH₃ | H | H | CH₃ | OCH₃ |
| 4-SO₂N(OCH₃)CH₃ | H | H | CH₃ | OCH₃ |
| 4-NO₂ | CH₃ | H | CH₃ | OCH₃ |
| 4-SO₂N(CH₃)₂ | CH₃ | H | CH₃ | OCH₃ |
| 4-Br | H | CH₃ | CH₃ | OCH₃ |
| 4-Cl | H | CH₃ | CH₃ | OCH₃ |
| 2-CH₃ | H | H | OCH₃ | OCH₃ |
| 2-Cl | H | H | OCH₃ | OCH₃ |
| 2-Br | H | H | OCH₃ | OCH₃ |
| 2-NO₂ | H | H | OCH₃ | OCH₃ |
| 2-SO₂N(CH₃)₂ | H | H | OCH₃ | OCH₃ |
| 2-SO₂N(C₂H₅)₂ | H | H | OCH₃ | OCH₃ |
| 2-SO₂N(CH₃)CH(CH₃)₂ | H | H | OCH₃ | OCH₃ |
| 2-SO₂N(CH₃)CH₂CH₂CH₃ | H | H | OCH₃ | OCH₃ |
| 2-OCH₃ | H | H | OCH₃ | OCH₃ |
| 2-CH₂CH₃ | H | H | OCH₃ | OCH₃ |
| 2-CH(CH₃)₂ | H | H | OCH₃ | OCH₃ |
| 2-CH₂CH(CH₃)₂ | H | H | OCH₃ | OCH₃ |
| 2-CH₂CH=CH₂ | H | H | OCH₃ | OCH₃ |
| 2-(CH₂)₃CH₃ | H | H | OCH₃ | OCH₃ |
| 2-SO₂N(OCH₃)CH₃ | H | H | OCH₃ | OCH₃ |
| 2-NO₂ | CH₃ | H | OCH₃ | OCH₃ |
| 2-SO₂N(CH₃)₂ | CH₃ | H | OCH₃ | OCH₃ |
| 2-Br | H | CH₃ | OCH₃ | OCH₃ |
| 2-Cl | H | CH₃ | OCH₃ | OCH₃ |
| 4-CH₃ | H | H | OCH₃ | OCH₃ |
| 4-Cl | H | H | OCH₃ | OCH₃ |
| 4-Br | H | H | OCH₃ | OCH₃ |
| 4-NO₂ | H | H | OCH₃ | OCH₃ |
| 4-SO₂N(CH₃)₂ | H | H | OCH₃ | OCH₃ |
| 4-SO₂N(C₂H₅)₂ | H | H | OCH₃ | OCH₃ |
| 4-SO₂N(CH₃)CH(CH₃)₂ | H | H | OCH₃ | OCH₃ |
| 4-SO₂N(CH₃)CH₂CH₂CH₃ | H | H | OCH₃ | OCH₃ |
| 4-OCH₃ | H | H | OCH₃ | OCH₃ |
| 4-CH₂CH₃ | H | H | OCH₃ | OCH₃ |
| 4-CH(CH₃)₂ | H | H | OCH₃ | OCH₃ |
| 4-CH₂CH(CH₃)₂ | H | H | OCH₃ | OCH₃ |
| 4-CH₂CH=CH₂ | H | H | OCH₃ | OCH₃ |
| 4-(CH₂)₃CH₃ | H | H | OCH₃ | OCH₃ |
| 4-SO₂N(OCH₃)CH₃ | H | H | OCH₃ | OCH₃ |
| 4-NO₂ | CH₃ | H | OCH₃ | OCH₃ |
| 4-SO₂N(CH₃)₂ | CH₃ | H | OCH₃ | OCH₃ |
| 4-Br | H | CH₃ | OCH₃ | OCH₃ |
| 4-Cl | H | CH₃ | OCH₃ | OCH₃ |

Formulations

Useful formulations of the compounds of Formula I can be prepared in conventional ways. They include dusts, granules, pellets, suspensions, emulsions, wettable powders, emulsifiable concentrates and the like. Many of these may be applied directly. Sprayable formulations can be extended in suitable media and used at spray volumes of from a few liters to several hundred liters per hectare. The formulations, broadly, contain about 0.1% to 99% by weight of active ingredient(s) and at least one of (a) about 0.1% to 20% surfactant(s) and (b) about 1% to 99.9% solid or liquid diluent(s). More specifically, they will contain these ingredients in the following approximate proportions set forth in Table IX:

TABLE IX

| | Active Ingredient | Weight Percent* | |
|---|---|---|---|
| | | Diluent(s) | Surfactant(s) |
| Wettable Powders | 20-90 | 0-74 | 1-10 |
| Oil Suspensions, Emulsions, Solutions, (including Emulsifiable Concentrates) | 3-50 | 40-95 | 0-15 |
| Aqueous Suspension | 10-50 | 40-84 | 1-20 |
| Dusts | 1-25 | 70-99 | 0-5 |
| Granules and Pellets | 0.1-95 | 5-99.9 | 0-15 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook", 4th Ed., McGraw-Hill, New York, 1963, pp. 8-59ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, June 23, 1959, Col. 3, line 66 through Col. 5, line 17 and Examples 1–4;

G. C. Klingman, "Weed Control as a Science", John Wiley & Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

The disclosures of the above-cited references are herein incorporated by reference.

Unless indicated otherwise, all parts are by weight in the following examples.

EXAMPLE 14

Wettable Powder

N-[(4-methoxy-6-methyl-2-pyrimidinyl)aminocarbonyl]-3-bromo-2-thiophenesulfonamide: 40%
dioctyl sodium sulfosuccinate: 1.5%
sodium ligninsulfonate: 3%
low viscosity methyl cellulose: 1.5%
attapulgite: 54%

The ingredients are thoroughly blended, passed through an air mill, to produce an average particle size under 15 microns, reblended, and sifted through a U.S.S. No. 50 sieve (0.3 mm opening) before packaging.

EXAMPLE 15

Granule

Wettable Powder of Example 14: 10%
attapulgite granules (U.S.S. #20-40 mesh; 0.84–0.42 mm): 90%

A slurry of wettable powder containing 25% solids is sprayed on the surface of attapulgite granules in a double-cone blender. The granules are dried and packaged.

EXAMPLE 16

Wettable Powder

N-[(4-methoxy-6-methyl-1,3,5-triazin-2-yl))aminocarbonyl]-3-methyl-2-thiophenesulfonamide: 80%
sodium alkylnaphthalenesulfonate: 2%
sodium ligninsulfonate: 2%
synthetic amorphous silica: 3%
kaolinite: 13%

The ingredients are blended and ground in a hammer-milled to produce an average particle size under 100 microns. The material is reblended, sifted through a U.S.S. #50 sieve and packaged.

EXAMPLE 17

Granule

Wettable Powder of Example 16: 15%
gypsum: 69%
potassium sulfate: 16%

The ingredients are blended in a rotating mixer and sprayed on to accomplish granulation. When most of the material has reached the desired range of 1.0 to 0.42 mm (U.S.S. #18 to 40 sieves), the granules are removed, dried and screened. Oversize material is crushed to produce additional material in the desired range. These granules contain 12% active ingredient.

EXAMPLE 18

Wettable Powder

N-[(4-methoxy-6-methyl-2-pyrimidinyl)aminocarbonyl]-3-methyl-2-thiophenesulfonamide: 65%
dodecylphenol polyethylene glycol ether: 2%
sodium ligninsulfonate: 4%
sodium silicoaluminate: 6%
montmorillonite (calcined): 23%

The ingredients are thoroughly blended. The liquid surfactant is added by spraying upon the solid ingredients in the blender. After grinding in a hammer-mill to produce particles essentially all below 100 microns, the material is reblended, sifted through a U.S.S. No. 50 sieve (0.3 mm opening) and packaged.

EXAMPLE 19

High Strength Concentrate

N-[(4,6-dimethoxy-2-pyrimidinyl)aminocarbonyl]-3-bromo-2-thiophenesulfonamide: 98.5%
silica aerogel: 0.5%
synthetic amorphous fine silica: 1.0%

The ingredients are blended and ground in a hammer-mill to produce a high strength concentrate essentially all passing a U.S.S. No. 50 screen (0.3 mm opening). This material may then be formulated in a variety of ways.

EXAMPLE 20

Aqueous Suspension

N-[(4-methoxy-6-methyl-2-pyrimidinyl)aminocarbonyl]-3-methyl-2-thiophenesulfonamide: 25%
hydrated attapulgite: 3%
crude calcium ligninsulfonate: 10%
sodium dihydrogen phosphate: 0.5%
water: 61.5%

The ingredients are ground together in a ball or roller mill until the solid particles have been reduced to diameters under 10 microns.

EXAMPLE 21

Oil Suspension

N-[(4-methoxy-6-methyl-1,3,5-triazin-2-yl)aminocarbonyl]-3-methyl-2-thiophenesulfonamide: 25%
polyoxyethylene sorbitol hexaoleate: 5%
highly aliphatic hydrocarbon oil: 70%

The ingredients are ground together in a sand mill until the solid particles have been reduced to under about 5 microns. The resulting thick suspension may be applied directly, but preferably after being extended with oils or emulsified in water.

EXAMPLE 22

Extruded Pellet

N-[(4-methoxy-6-methyl-2-pyrimidinyl)aminocarbonyl]-3-bromo-2-thiophenesulfonamide: 25%
anhydrous sodium sulfate: 10%
crude calcium ligninsulfonate: 5%
sodium alkylnaphthalenesulfonate: 1%
calcium/magnesium bentonite: 59%

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 23

Granule

N-[(4,6-dimethoxy-2-pyrimidinyl)aminocarbonyl]-3-bromo-2-thiophenesulfonamide: 80%
dioctyl sodium sulfosuccinate: 1.0%
crude ligninsulfonate salt (containing 5-20% natural sugars): 10.0%
sugar: 9.0%

The ingredients are blended and milled to pass through a 100 mesh screen. This screened material is then added to a fluid bed granulator where the air flow is adjusted to gently fluidize the material and finally a fine mist of water is sprayed onto the fluidized material. The fluidization and spraying are continued until granules of the desired size range are made. The spraying is then stopped, but fluidization is continued optionally with heat, until the moisture in the material is reduced to the desired level, generally less than 1%. The material is discharged, screened to the desired product range, generally with a range of 10-100 mesh (2000-149 microns), and packaged for use.

Utility

The compounds of the present invention are active herbicides. They have utility for broad-spectrum pre- and/or post-emergence weed control in areas where complete control of all vegetation is desired, such as around fuel storage tanks, ammunition depots, industrial storage areas, oil-well sites, drive-in theaters, around billboards, highway and railroad structures. By properly selecting rate and time of application, compounds of this invention may also be used to modify plant growth beneficially, and also to selectively control weeds in crops such as wheat, barley and rice.

The precise amount of the compounds of Formula I to be used in any given situation will vary according to the particular end result desired, the amount of foliage present, the weeds to be controlled, the crop species involved, the soil type, the formulation and mode of application, weather conditions, etc. Since so many variables play a role, it is not possible to state a rate of application suitable for all situations. Broadly speaking, the compounds of this invention are used at levels of about 0.001 to 20 kg/ha with a preferred range of 0.03 to 10 kg/ha. In general, the higher rates of application from within this range will be selected for adverse conditions or where extended presistence in soil is desired.

The compounds of Formula I may be combined with other herbicides and are particularly useful in combination with the ureas: such as 3-(3,4-dichlorophenyl)-1,1-dimethylurea (diuron); the triazines: such as 2-chloro-4-(ethylamino)-6-(isopropylamino)-s-triazine (atrazine); the uracils: such as 5-bromo-3-sec-butyl-6-methyluracil (bromacil); N-(phosponomethyl)glycine (glyphosate); 3-cyclohexyl-1-methyl-6-dimethylamino-s-triazine-2,4(1H,3H)-dione (hexazinone); N,N-dimethyl-2,2-diphenylacetamide (diphenamid); 2,4-dichlorophenoxyacetic acid (2,4-D) (and closely related compounds); 4-chloro-2-butynyl-3-chlorophenylcarbamate (barban); S-(2,3-dichloroallyl)-diisopropylthiocarbamate (diallate); S-(2,3,3-trichloroallyl)-diisopropylthiocarbamate (triallate); 1,2-dimethyl-3,5-diphenyl-1H-pyrazolium methyl sulfate (difenzoquat methyl sulfate); methyl 2-[4-(2,4-dichlorophenoxy)phenoxy]propanoate (diclofop methyl); 4-amino-6-tert-butyl-3-(methylthio)-1,2,4-triazin-5(4H)-one (metribuzin); 3-(3,4-dichlorophenyl)-1-methoxy-1-methylurea (linuron); 3-isopropyl-1H-2,1,3-benzothiodiazin-4(3H)-one-2,2-dioxide (bentazon); α,α,α-trifluoro-2,6-dinitro-N,N-dipropyl-p-toluidine (trifluralin); 1,1'-dimethyl-4,4'-bipyridinium ion (paraquat); monosodium methanearsonate (MSMA); 2-chloro-2',6'-diethyl (methoxymethyl)acetanilide (alachlor); 1,1-dimethyl-3-(α,α,α-trifluoro-m-tolyl)urea (fluometuron); and 5-[2-chloro-4-(trifluoromethyl)phenoxy]-2-nitrobenzoic acid, methyl ester (acifluorfen-methyl).

The activity of these compounds was discovered in greenhouse tests. The tests are described and data resulting from them are shown below.

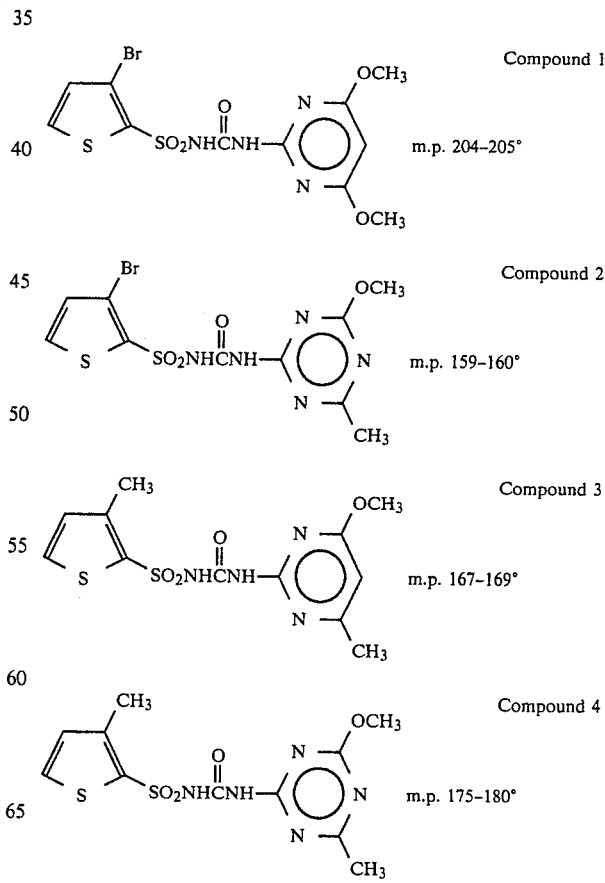

4,523,943
-continued
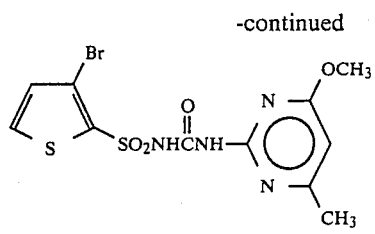 Compound 5
m.p. 189–190°
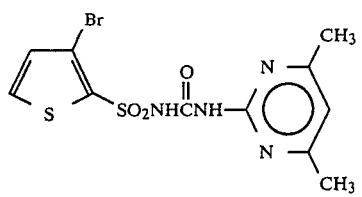 Compound 6
m.p. 204–207°
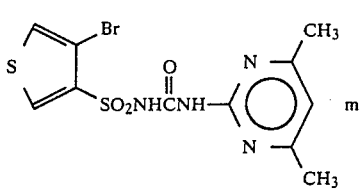 Compound 7
m.p. 214° (dec.)
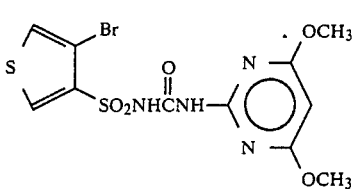 Compound 8
m.p. 198–200°
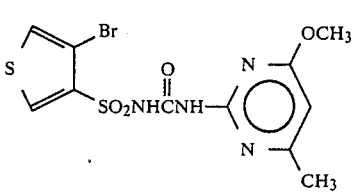 Compound 9
m.p. 200–203°
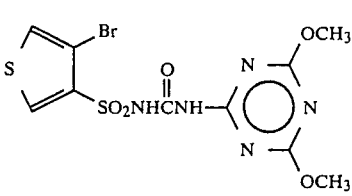 Compound 10
m.p. 180–184°
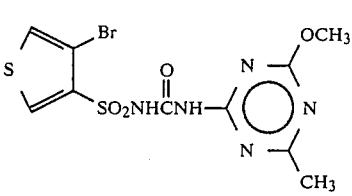 Compound 11
m.p. 180–183°
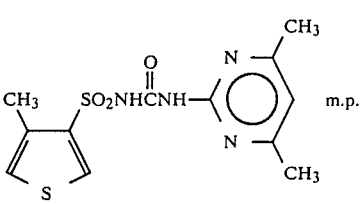 Compound 12
m.p. 186–191°
-continued
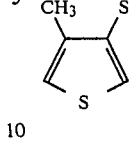 Compound 13
m.p. 175–178°
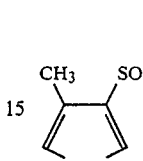 Compound 14
m.p. 145–152°
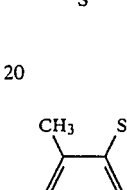 Compound 15
m.p. 154–156°
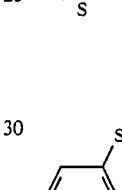 Compound 16
m.p. 147–149°
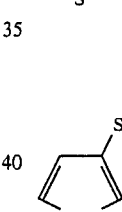 Compound 17
m.p. 212–213° (dec.)
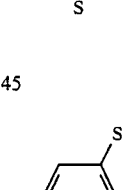 Compound 18
m.p. 210–212° (dec.)
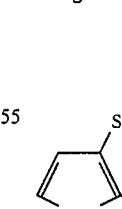 Compound 19
m.p. 178–190° (dec.)
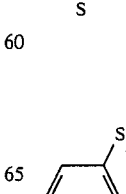 Compound 20
m.p. 187–193° (dec.)

-continued

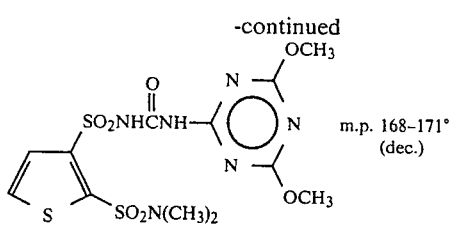

Compound 21 m.p. 168-171° (dec.)

Test A

Seeds of crabgrass (Digitaria spp.), barnyardgrass (*Echinochloa crusgalli*), wild oats (*Avena fatua*), cassia (*Cassia tora*), morningglory (Ipomoea sp.), cocklebur (Xanthium spp.), sorghum, corn, soybean, rice, wheat and nutsedge tubers (*Cyperus rotundus*) were planted in a growth medium and treated preemergence with the chemicals dissolved in a non-phytotoxic solvent. At the same time, cotton having five leaves (including cotyledonary ones), bush beans with the second trifoliate leaf expanding, crabgrass and barnyardgrass with two leaves, wild oats with one leaf, cassia with three leaves (including cotyledonary ones), morningglory and cocklebur with four leaves (including the cotyledonary ones), sorghum and corn with three leaves, soybean with two cotyledonary leaves, rice with two leaves, wheat with two leaves, and nutsedge with three to five leaves were sprayed. Treated plants and controls were maintained in a greenhouse for sixteen days, then all species were compared to controls and visually rated for response to treatment.

The ratings are based on a numerical scale extending from 0=no injury, to 10=complete kill. The accompanying descriptive symbols have the following menings:
C=chlorosis or necrosis;
E=emergence inhibition;
G=growth retardation;
H=formative effects;
U=unusual pigmentation; and
Y=flowering response.

TABLE A

| | Compound 7 | | Compound 8 | | Compound 9 | | Compound 10 | | Compound 11 | | Compound 6 | |
|---|---|---|---|---|---|---|---|---|---|---|---|---|
| Rate kg/ha | 0.4 | .05 | 0.4 | .05 | 0.4 | .05 | 0.4 | .05 | 0.4 | .05 | 0.4 | |
| POST-EMERGENCE | | | | | | | | | | | | |
| Bush bean | 9C | 9C | 8C | 8C | 9C | 9C | 6C,9G,6Y | 3C,9G,6Y | 10C | 9C | 9C | |
| Cotton | 6C,9G | 5C,9G | 6C,9G | 6C,9G | 6C,9G | 6C,9G | 9C | 5C,9G | 9C | 2U,5C,9G | 9C | |
| Morningglory | 5C,9G | 9C | 9C | 10C | 9C | 9C | 9C | 10C | 10C | 6C,9G | 10C | |
| Cocklebur | 10C | 9C | 10C | 10C | 9C | 9C | 9C | 10C | 9C | 10C | 8C | |
| Cassia | 9C | 5C,9G | 9C | 9C | 9C | 9C | 9C | 9C | 9C | 9C | 5C,7G | |
| Nutsedge | 9C | 3C,9G | 9C | 9C | 5C,8G | 9C | 5C,8G | 6C,9G | 9C | 4C,9G | 2C,7G | |
| Crabgrass | 6C,9G | 4C,8G | 4C,8G | 3C,8G | 6C,9G | 5C,9G | 9C | 1C,5G | 5C,8G | 2C,8G | 9C | |
| Barnyardgrass | 9C | 9C | 6C,9H | 6C,9H | 6C,9H | 5C,9H | 5C,9G | 9C | 9C | 9C | 1C,6G | |
| Wild Oats | 6C,9G | 6U,9C | 5C,9H | 5C,9G | 6U,9C | 5U,9G | 2C,9G | 3G | 2C,9G | 2C,7G | 1C,6G | |
| Wheat | 9C | 7U,9C | 3C,9G | 3C,9G | 1C,7G | 1C,9C | 5C,9G | 0 | 5C,9G | 5C,8G | 9C | |
| Corn | 7U,9C | 7U,9C | 3C,9G | 1C,8G | 7U,9C | 2U,9G | 6C,9G | 7U,9G | 7U,9C | 2C,7G | 10C | |
| Soybean | 6C,9G | 6C,9G | 6C,9G | 6C,9G | 7U,9G | 5U,9G | 6C,9G | 6C,9G | 6C,9G | 7U,9G | 6C,9G | |
| Rice | 6C,9G | 6C,9G | 5C,9G | 5C,9G | 6C,9G | 6C,9G | 6C,9G | 4C,7G | 5C,9G | 6C,9G | 6C,9G | |
| Sorghum | 9C | 9C | 5U,9G | 4U,9G | 4U,9C | 4U,9C | 2U,9G | 2U,9G | 9C | 2U,3C,9G | 9C | |
| PRE-EMERGENCE | | | | | | | | | | | | |
| Morningglory | 9H | 9H | 9G | 9G | 5C,9H | 5C,9G | 9H | 9H | 5C,9G | 9H | 9H | |
| Cocklebur | 9H | 9H | 9H | 9H | 9H | 9H | 9H | 9G | 9H | 9H | 9H | |
| Nutsedge | 9G | 8G | 9G | 9G | 9G | 9G | 9G | 9G | 9G | 9G | 8G | |
| Crabgrass | 10E | 10E | 10E | 10E | 10E | 10E | 10E | 10E | 10E | 10E | 2C,8G | |
| Barnyardgrass | 5C,9G | 2C,9G | 10E | 3C,8G | 3C,5G | 4C,9G | 1C,4G | 3C,9G | 3C,5G | 2C,7G | 6C,9H | |
| Wild Oats | 9H | 3C,9H | 4C,8G | 5C,9H | 4C,9H | 5C,9H | 5C,9G | 5C,9H | 2C,9H | 5C,9H | 3C,9H | |
| Wheat | 5C,9H | 4C,8G | 3C,9G | 3C,8G | 5C,9H | 5C,9H | 2C,8G | 2C,9H | 1C,8G | 2C,7G | 9H | |
| Corn | 10E | 2C,9G | 9G | 1C,8G | 9H | 9H | 2C,9G | 1C,5G | 9G | 3U,9H | 9H | |
| Soybean | 10E | 7G | 9G | 9G | 10E | 10E | 9H | 2U,9G | 7G | 9H | 9H | |
| Rice | 10E | 10H | 10E | 9G | 9H | 9H | 9H | 9H | 9H | 9H | 9H | |
| Sorghum | 10E | 10E | 10H | 9G | 10E | 10E | 6C,9H | 2C,8G | 6C,9H | 2C,9G | 6C,9H | |

| | Compound 1 | | Compound 2 | | Compound 3 | | Compound 4 | | Compound 5 | |
|---|---|---|---|---|---|---|---|---|---|---|
| | 0.1 | | 0.1 | | 0.4 | | 0.4 | | 0.1 | |
| Bush bean | 9C | | 9C | | 9C | | 8C | | 9C | |
| Cotton | 9C | | 9C | | 9C | | 9C | | 9C | |
| Morningglory | 10C | | 10C | | 10C | | 10C | | 10C | |
| Cocklebur | 10C | | 10C | | 9C | | 6C,9G | | 10C | |
| Cassia | 9C | | 9C | | 9C | | 6C,9G | | 9C | |
| Nutsedge | 10C | | 1C,2G | | 10C | | 5C,8G | | 3C,8G | |
| Crabgrass | 3C,6G | | 1C,4G | | 4C,9G | | 2C,8G | | 3C,8G | |
| Barnyardgrass | 5C,9H | | 5C,9H | | 10C | | 9C | | 9C | |
| Wild Oats | 1C,8G | | 0 | | 5H,9C | | 0 | | 1C,6G | |
| Wheat | 1C,8G | | 0 | | 5H,9C | | 1C | | 4C,9G | |
| Corn | 1C,9H | | 4C,9H | | 8U,9C | | 7U,9G | | 9C | |
| Soybean | 9C | | 9C | | 9C | | 9C | | 9C | |
| Rice | 5C,9G | | 4C,9G | | 8C | | 4C,9G | | 9C | |
| Sorghum | 3C,8G | | 2C,8G | | 9C | | 3C,8G | | 10C | |
| Morningglory | 9G | | 9H | | 9G | | 9G | | 9H | |
| Cocklebur | 9H | | 9H | | 9G | | 9G | | 10E | |
| Nutsedge | 5C,9G | | 5C,9G | | 8G | | 9C | | 6C,9G | |
| Crabgrass | 10E | | 5G | | 10E | | 8G | | 9G | |
| Barnyardgrass | 3C,5G | | 2C,5G | | 4C,9G | | 2C,8G | | 3C,8G | |
| Wild Oats | 2C,9H | | 5C,9H | | 5C,9H | | 3C,9H | | 5C,9H | |
| Wheat | 1C,8G | | 1C | | 4C,9H | | 5G | | 8G | |
| Corn | 7G | | 9G | | 9H | | 6G | | 9G | |
| Soybean | 9H | | 9H | | 9H | | 9H | | 10E | |
| Rice | 9H | | 8H | | 9H | | 9H | | 9H | |
| Sorghum | 1C,8G | | 2C,8G | | 10E | | 10E | | 7C,9H | |

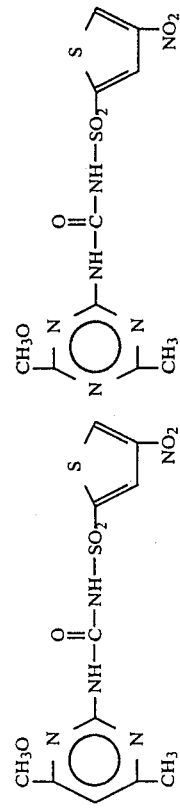

| | Compound No. | | | | | | | | | |
|---|---|---|---|---|---|---|---|---|---|---|
| | 12 | 13 | 14 | 15 | 17 | 18 | 19 | 20 | Compound 21 | |
| Rate kg/ha | 0.05 | 0.05 | 0.05 | 0.05 | 0.05 | 0.05 | 0.05 | 0.05 | 0.05 | |
| POST-EMERGENCE | | | | | | | | | | |
| Bush bean | 6C,9G, 6Y | 6C,9G, 6Y | 6C,9G, 6Y | 3C,7G, 6Y | 9C | 9C | 9C | 9C | 9C | |
| Cotton | 4C,4H, 7G | 4C,4H, 9G | 2U,5C, 9G | 5C,9G | 5C,9G | 6C,9G | 5C,9G | 6C,9G | 5C,9G | |
| Morningglory | 4C,8G | 2C,5H | 5C,9G | 5C,9G | 6C,9G | 9C | 6C,9G | 5C,9G | 6C,9G | |
| Cocklebur | 5C,9G | 2C,6G | 5C,9G | 3G | 4C,9G | 5C,9G | 9C | 9C | 9C | |
| Cassia | 2C,5G | 6C,9G | 5C,9G | 3C,7G | 2C,7G | 3C,9G | 6C,9G | 4C,8G | 4C,8G | |
| Nutsedge | 2C,7G | 5C,8G | 1C,5G | 7G | 8G | 9G | 2C,8G | 4G | 3G | |
| Crabgrass | 6G | 2C,4G | 2C,7G | 0 | 6C,9G | 5C,9G | 5C,9G | 3C,9G | 9C | |

TABLE A-continued

| | | | | | | | | | | | | | |
|---|---|---|---|---|---|---|---|---|---|---|---|---|---|
| Barnyardgrass | 9H | 2C,7H | 5C,9H | 2C,8H | 9C | 6H | 6C,9H | 9C | 9C | 9C | 9C | 9C |
| Wild Oats | 3C,8G | 0 | 2C,9H | 4G | 2C,9H | 0 | 1C,9G | 2C,9G | 3C,9G | 2C,9G | 1C,8G | 1C,8G |
| Wheat | 2C,8H | 3G | 9G | 2G | 2C,9G | 0 | 5C,9G | 3C,9G | 4U,9G | 3C,9G | 1C,9G | 2C,8G |
| Corn | 3C,9G | 2C,9G | 5U,9G | 2C,7H | 7U,9G | 2C,6H | 5U,9G | 4U,9G | 6C,9G | 4U,9C | 7U,9C | 7U,9G |
| Soybean | 9C | 5C,9G | 5C,9G | 5C,9G | 9C | 9C | 6C,9G | 5C,9G | 6C,9G | 9C | 6C,9G | 6C,9G |
| Rice | 6C,8G | 4C,9G | 6C,9G | 3C,9G | 6C,9G | 2G | 5C,9G | 6C,9G | 6C,9G | 5C,9G | 5C,9G | 6C,9G |
| Sorghum | 2C,9G | 5G | 2U,9G | 2C,7G | 3U,9G | 2C,6G | 5U,9G | 5U,9G | 5U,9G | 5U,9G | 5U,9G | 4C,9G |
| PRE-EMERGENCE | | | | | | | | | | | | |
| Morningglory | 9G | 9G | 9H | 9H | 2C,9G | 9H | 9H | 9G | 9C | 9C | 9C | 9C |
| Cocklebur | 9G | 8G | 9H | 9H | — | 9H | 9H | 9H | 9H | 9H | 9H | 9H |
| Cassia | 9G | 9G | 8G | 9G | 9G | 9G | 2C,9G | 9G | 9G | 3C,9G | 9G |
| Nutsedge | 8G | 0 | 8G | 10E | 8G | 5G | 10E | 4C,9G | 10E | 4G | 7G |
| Crabgrass | 1H | 6G | 2C,5G | 3C,6G | 2C,7G | 1C | 9G,3C | 5C,9G | 5C,9G | 3C,8G | 5C,8G |
| Barnyardgrass | 2C,7G | 9H | 2C,9H | 3C,8H | 3C,9H | 1C,2G | 9H | 5C,9H | 9H,5C | 6C,9H | 5C,9H |
| Wild Oats | 8G | 0 | 1C,9G | 3C,8G | 3C,9G | 2G | 2C,9G | 4C,9G | 3C,9G | 3C,9G | 4C,9G |
| Wheat | 8G | 0 | 1C,9G | 3C,8G | 2C,9G | 3G | 5C,9H | 4C,9G | 2U,9G | 2C,8G | 2C,8G |
| Corn | 9G | 9H | 8H | 9G | 10E | 3C,7G | 2C,9G | 2C,9G | 2C,9H | 9G | 9G | 10E |
| Soybean | 9H | 7H | 10E | 9H | 9H | 9H | 9H | 9H | 9H | 9H | 9H | 9H |
| Rice | 9H | 9H | 10E | 10E | 10E | 2G | 10E | 10E | 10E | 10E | 10E | 10E |
| Sorghum | 2C,9G | 7G | 10E | 4C,9H | 10E | 7G | 10E | 10H | 10E | 5C,9H | 5C,9H | 5C,9H |

Test B

Two plastic bulb pans were filled with fertilized and limed Fallsington silt loam soil. One pan was planted with corn, sorghum, Kentucky bluegrass and several grassy weeds. The other pan was planted with cotton, soybeans, purple nutsedge (*Cyperus rotundus*), and several broadleaf weeds. The following grass and broadleaf weeds were planted: crabgrass (*Digitaria sanguinalis*), barnyardgrass (*Echinochloa crusgalli*), wild oats (*Avena fatua*), johnsongrass (*Sorghum halepense*), dalligrass (*Paspalum dilatatum*), giant foxtail (*Setaria faberii*), cheatgrass (*Bromus secalinus*), mustard (*Brassica arvensis*), cocklebur (*Xanthium pensylvanicum*), pigweed (*Amaranthus retroflexus*), morningglory (*Ipomoea hederacea*), cassia (*Cassia tora*), teaweed (*Sida spinosa*), velvetleaf (*Abutilon theophrasti*), and jimsonweed (*Datura stramonium*). A 12.5 cm diameter plastic pot was also filled with prepared soil and planted with rice and wheat. Another 12.5 cm pot was planted with sugarbeets. The above four containers were treated pre-emergence with several test compounds within the scope of the invention.

Twenty-eight days after treatment, the plants were evaluated and visually rated for response to the chemical treatments utilizing the rating system described previously for Test A. The data are summarized in Table B. Note that compounds from within the scope of the invention are useful for pre-emergence weed control in wheat.

overall with the test chemical dissolved in a non-phytotoxic solvent. Two weeks after treatment, all species were compared to untreated controls and visually rated for response to treatment. The rating system was as described previously for Test A. The data are presented in Table C. The compound tested by this procedure is useful for the post-emergence control of weeds in wheat.

TABLE C

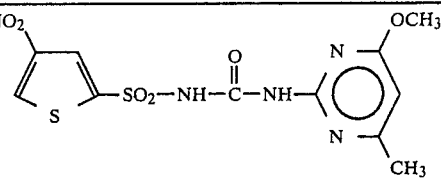

| Rate kg/ha | 0.06 | 0.25 | 1.0 |
| --- | --- | --- | --- |
| Soybeans | 10G,7C | 10G,7C | 10G,8C |
| Velvetleaf | 10C | 10C | 10C |
| Sesbania | 9G,6C | 10G,9C | 10G,9C |
| Cassia | 6G,2C | 10G,5C | 10G,6C |
| Cotton | 6G,3H | 6G,3H | 7G,3H |
| Morningglory | 7G | 10G,9C | 10C |
| Alfalfa | 8G,2C | 10G,7C | 10G,9C |
| Jimsonweed | 8G,6C | 8G,7C | 10C |
| Cocklebur | 6G | 8G | 10G,9C |
| Corn | 7G,2U | 7G,1U | 10G,7C |
| Crabgrass | 4G | 3G | 7G,2C |
| Rice | 8G,3C | 9G,4C | 10G,8C |
| Nutsedge | 0 | 0 | 0 |
| Barnyardgrass | 2G | 3G | 10G,3H |
| Wheat | 4G | 4G | 9G |

TABLE B

PRE-EMERGENCE ON FALLSINGTON SILT LOAM

| | Compound 1 | | Compound 2 | | Compound 3 | | | | Compound 4 | | Compound 5 | |
| --- | --- | --- | --- | --- | --- | --- | --- | --- | --- | --- | --- | --- |
| Rate kg/ha | 0.03 | 0.12 | 0.03 | 0.12 | 0.007 | 0.015 | 0.06 | 0.25 | 0.06 | 0.25 | 0.03 | 0.12 |
| Crabgrass | 6G | 7G,2C | 0 | 7G,2C | 0 | 6G | 6G | 7G,2C | 3G | 5G | 3G | 8G,3C |
| Barnyardgrass | 6G,3C | 7G,3H | 4G | 9G,9C | 6G,2H | 8G,5H | 10C | 10C | 7G,7H | 9G,8H | 8G,5H | 9G,8C |
| Sorghum | 6G,2H | 7G,5H | 6G,3H | 7G,5H | 8G,9C | 10C | 10C | 10C | 8G,3H | 8G,3H | 9G,9C | 10E |
| Wild Oats | 3G | 3G | 0 | 0 | 0 | 5G,2C | 8G,6C | 8G,9C | 0 | 2G | 2G | 4G |
| Johnsongrass | 5G | 5G,2H | 3G | 3G,2H | 5G | 8G,8C | 9G,8C | 10C | 3G | 7G,3H | 6G,3H | 8G,5H |
| Dallisgrass | — | — | — | — | 0 | 7G,2C | 8G,5H | 9G,5H | 0 | 3G | — | — |
| Giant foxtail | 4G,3C | 6G,4C | 4G,3C | 6G,3H | 4G,3H | 10C | 10C | 10C | 3G | 7G | 6G,5C | 7G,3C |
| Ky. bluegrass | 5G | 8G,5E | 5G | 5G | 6G | 10C | 10C | 10C | 7G | 8G | 7G,8C | 8G,9C |
| Cheatgrass | 3G | 7G,5E | 0 | 5G | 5G,2C | 8G,8C | 8G,7C | 10C | 0 | 5G | 10E | 8G,8C |
| Sugarbeets | 10C | 10C | 10C | 10C | 9G,9C | 10C | 10C | 10C | 9G,9C | 10C | 10C | 10C |
| Corn | 3G | 6G,3H | 6G,5H | 8G,5H | 9G,9C | 10C | 10C | 10C | 7G,5H | 8G,7C | 7G,5H | 9G,5H |
| Mustard | 10C | 10C | 10C | 10C | 10C | 10C | 10C | 10C | 10C | 10C | 10C | 10C |
| Cocklebur | 4G | 6G | 5G | 5G,3H | 7G | 10C | 7G | 8G | 7G | 8G | 5G | 6G |
| Pigweed | 10E | 10E | 10E | 10E | 10C | 10C | 10E | 10E | 10E | 10E | 10E | 10E |
| Nutsedge | 7G | 8G,3C | 0 | 7G | 6G | 7G | 7G | 8G | 4G | 7G | 0 | 0 |
| Cotton | 5G | 5G,2H | 8G,5C | 9G,7C | 5G,3H | 8G,5H | 8G | 8G,5C | 8G | 8G | 7G,5H | 8G,5C |
| Morningglory | 2G | 7G | 9G,8C | 9G | 6G | 7G | 8G,5C | 9G,8C | 8G | 8G,8C | 7G | 9G,9C |
| Cassia | 8G,5C | 8G,7C | 9G,5C | 9G,8C | 9G,8C | 9G,8C | 8G | 8G,5C | 7G | 8G,8C | 9G,8C | 9G,8C |
| Teaweed | 5G | 6G,3H | 8G,5C | 8G,7C | 6G,5C | 8G,3C | 10C | 10C | 8G,8C | 8G,8C | 6G | 7G,7C |
| Velvetleaf | 9G,7C | 10C | 10C | 10C | 10C | 10C | 10C | 10C | 9G,8C | 9G,9C | 9G,8C | 9G,9C |
| Jimsonweed | 6G,5E | 7G,5E | 10C | 8G | 3G | 5G,3C | 7G | 7G,5C | 6G,3C | 7G,7C | 8G,9C | 9G,8C |
| Soybean | 5G | 6G,3H | 9G,5H | 9G,8C | 6G,3H | 8G,5H | 8G,5H | 8G,5H | 8G,5H | 8G,5H | 6G,3H | 7G,7C |
| Rice | 6G | 10C | 4G | 6G | 9G,9C | 10C | 10E | 10E | 5G,3C | 7G,5H | 8G,5E | 10E |
| Wheat | 3G | 4G | 2G | 3G | 3G | 5G | 6G | 8G,5C | 0 | 0 | 5G | 5G |

Test C

Twenty-five cm diameter plastic pots filled with Fallsington silt loam were planted with soybeans, cotton, alfalfa, corn, rice, wheat, sorghum, velvetleaf (*Abutilon theophrasti*), sesbania (*Sesbania exaltata*), Cassia (*Cassia tora*), morningglory (*Ipomoea hederacea*), jimsonweed (*Datura stramonium*), cocklebur (*Xanthium pensylvanicum*), crabgrass (Digitaria spp.), nutsedge (*Cyperus rotundus*), barnyardgrass (*Echinochloa crusgalli*), giant foxtail (*Setaria faberii*) and wild oats (*Avena fatua*). Approximately 2½ weeks after planting, the young plants and the soil around them were sprayed

| Giant Foxtail | 0 | 0 | 7G,2H |
| --- | --- | --- | --- |
| Wild Oats | 5G | 4G | 10G |
| Sorghum | 8G,3H | 8G,3H | 7G,2H |

Test D

The high herbicidal activity and utility for pre-emergence weed control in wheat and barley of two of the compounds from within the scope of the invention is evident from the results obtained in this test. The experiment concerned pre-emergence applications on soil.

The containers used were 25 cm diameter plastic pots filled with Fallsington silt loam. One set of pots was planted to weeds, the seeds of which were uniformly mixed with the top 1.2 cm layer of soil. The species selected were: johnsongrass (*Sorghum halepense*), barnyardgrass (*Echinochloa crusgalli*), crabgrass (*Digitaria sanguinalis*), giant foxtail (*Setaria faberii*), velvetleaf (*Abutilon theophrasti*), jimsonweed (*Datura stramonium*), mustard (*Brassica arvensis*), and pigweed (*Amaranthus retroflexus*). Another set of pots was planted in the following crops with from one to four species per pot: corn (planting depth 3.7 cm), cotton, soybeans, sunflower, Clinton oats, wheat, Black Valentine beans, rice, sorghum, peas, flax, and peanuts (all at 2.5 cm depth), cucumbers, cabbage, alfalfa, safflower, sugarbeets, tomato, spinach, barley, and Kentucky bluegrass (all at 1.2 cm depth). Immediately after planting, the test chemicals were applied to the soil surfaces dissolved in a non-phytotoxic solvent. One pot from the weed phase and one of each of the crop species were left untreated for the purpose of comparison. The treated and untreated pots were promptly watered with approximately 4 mm of simulated rainfall and then held in a greenhouse for several weeks. Visual weed and crop response ratings were made 28 days after treatment utilizing the rating system as described above for test procedure A. The data are given in Table D.

(*Solanum nigrum*), yellow rocket (*Barbarea vulgaris*), wild mustard (*Brassica kaber*) and wild buckwheat (*Polygonum convolvulus*). The above two pans were treated pre-emergence. At the same time two pans in which the above plant species were growing were treated post-emergence. Plant height at the time of treatment ranged from 1–15 cm depending on plant species.

The compound applied was diluted with a non-phytotoxic solvent and sprayed over-the-top of the pans. An untreated control and a solvent alone control were included for comparison. All treatments were maintained in the greenhouse for 20 days at which time the treatments were compared to the controls and the effects visually rated. The recorded data are presented in Table E. The compound provides excellent selective pre- and/or post-emergence weed control in wheat and barley.

TABLE E

| | Compound 4 | | | |
|---|---|---|---|---|
| | Pre-Emergence | | Post-Emergence | |
| Rate kg/ha | 0.06 | 0.25 | 0.06 | 0.25 |
| Wheat | 0 | 0 | 0 | 0 |
| Barley | 0 | 2G | 0 | 0 |
| Wild Oats | 0 | 1C,2G | 0 | 0 |
| Downy brome | 3C,4G | 6C,7G | 2G | 3C,4G |
| Cheatgrass | 3C,6G | 5C,7G | 3G | 2C,7G |
| Blackgrass | 7C,7G | 8C,8G | 7C,5G | 7C,7G |

TABLE D

| | Compound 3 | | | | Compound 4 | | | |
|---|---|---|---|---|---|---|---|---|
| Rate kg/ha | 0.003 | 0.007 | 0.015 | 0.03 | 0.015 | 0.03 | 0.06 | 0.12 |
| Corn | | | | 9G,9C | | | | 9G,9C |
| Cotton | | | | 7G,5H | | | | 9G,5C |
| Soybean | | | | 7G,7H | | | | 8G,5C |
| Peanut | | | | 6G | | | | 7G,3C |
| Sunflower | | | | 7G,5H | | | | 9G,7C |
| Oats | | | | 6G | | | | 5G |
| Wheat | | | | 7G,3C | | | | 3G |
| Sorghum | | | | 8G,8C | | | | 7G,5H |
| Sugarbeet | | | | 8G,8C | | | | 10E |
| Pea | | | | 10E | | | | 10E |
| Flax | | | | 8G,5H | | | | 9G,9C |
| Alfalfa | | | | 7G,7C | | | | 8G,8C |
| Bean | | | | 5G,3H | | | | 8G,5H |
| Spinach | | | | 8G,5H | | | | 9G,8C |
| Cabbage | | | | 8G,8C | | | | 10E |
| Tomato | | | | 3G | | | | 10C |
| Rice | | | | 10E | | | | 6G,3C |
| Safflower | | | | 7G | | | | 7G |
| Cucumber | | | | 8G,5H | | | | 9G,8C |
| Ky. bluegrass | | | | 6G,3C | | | | 7G,5C |
| Barley | | | | — | | | | 4G |
| Tobacco | | | | — | | | | — |
| Broadleaves | 6G,4C | 7G,6C | 8G,8C | — | 8G,7C | 9G,8C | 8G,7C | — |
| Grasses | 4G | 5G,2C | 7G,2C | — | 2G | 3G | 4G | — |

Test E

Two ten-inch in diameter plastic pans lined with polyethylene liners were filled with prepared Fallsington silt loam soil. One pan was planted with seeds of wheat (*Triticum aestivum*), barley (*Hordeum vulgare*), wild oats (*Avena fatua*), downy brome (*Bromus tectorum*), cheatgrass (*Bromus secalinus*), blackgrass (*Alopecurus myosuroides*), annual bluegrass (*Poa annua*), green foxtail (*Setaria viridis*), quackgrass (*Agropyron repens*), Italian ryegrass (*Lolium multiflorum*) and ripgut brome (*Bromus rigidus*). The other pan was planted with seeds of Russian thistle (*Salsola kali*), tansy mustard (*Descuraina pinnata*), smartweed (*Polygonum pensylvanicum*), tumble mustard (*Sisymbrium altissium*) kochia (*Kochia scoparia*), shepherd's purse (*Capsella bursa-pastoris*), (*Matricaria inodora*, black nightshade

| Annual bluegrass | 3C,6G, | 4C,7G | 3C,5G | 7C,7G |
|---|---|---|---|---|
| Green foxtail | 2C,3G | 7C,7G | 6C,5G | 8C,8G |
| Quackgrass | 2C,2G | 4C,6G | 1G | 3C,4G |
| Italian ryegrass | 3C,7G | 5C,7G | 1C,3G | 6C,5G |
| Ripgut brome | 1G | 3C,4G | 1G | 1C,2G |
| Russian thistle | 7C,6G | 10C | 10C | 10C |
| Tansy mustard | 10C | 10C | 10C | 10C |
| Smartweed | — | — | — | — |
| Tumble mustard | 10C | 10C | 10C | 10C |
| Kochia | 9C,9G | 10C | 10C | 10C |
| Shepherd's purse | 10C | 10C | 10C | 10C |
| *Matricaria inodora* | 9C,9G | 10C | 10C | 10C |
| Black nightshade | 5C,8G | 6C,7G | 2C,3G | 10C |
| Yellow Rocket | 10C | 10C | 10C | 10C |
| Wild mustard | 10C | 10C | 10C | 10C |
| Wild buckwheat | 4C,7G | 7C,8G | 10C | 10C |

Test F

Test samples were formulated and applied directly to the water of paddies, three days after transplanting of rice. The paddies were maintained in a greenhouse and plant response ratings were taken at different times after application. See Table F.

TABLE F

| | | Compound 4 | | |
|---|---|---|---|---|
| Rate, kg/ha | Rice (2 weeks) | Rice (7 weeks) | Barnyard-grass* (7 weeks) | Water Chestnut** (7 weeks) |
| .01 | 0 | 2G | 9C | 0 |
| .04 | 0 | 7G,3C | 10C | 3G |
| | | Compound 1 | | |
| Rate, kg/ha | Rice (5 weeks) | Barnyard-grass (5 weeks) | Water Chestnut (5 weeks) | Arrowhead*** (5 weeks) |
| .01 | 0 | 5E,6G | 7G | 9G |
| .04 | 0 | 9E,7G | 9C | 10E |

*Echinochloa sp.
**Eleocharia sp.
***Sagittaria sp.

It may readily be seen that the compounds tested are useful for weed control in rice.

Test G

Purple nutsedge (*Cyperus rotundus*) tubers were planted about 2 cm deep in Fallsington silt loam soil contained in 10 cm diameter plastic pots. Five tubers were planted in each pot. A compound from the scope of this invention was dissolved in a non-phytotoxic diluent and sprayed at 560 l/ha in four methods of application: soil surface, tuber/soil, soil incorporated and post-emergence. The soil surface spray consisted of spraying the compound on the surface of the firmed covering soil. The tuber/soil spray consisted of spraying the compound on exposed tubers and subtending soil before adding the untreated covering soil. Soil incorporated treatment consisted in mixing the compound with the covering soil before using it to cover the tubers. The post-emergence treatment was sprayed on nutsedge foliage and the surrounding soil surface when nutsedge had emerged and grown to a height of about 12 cm. Pots receiving the post-emergence treatments were placed directly in the greenhouse. Pots receiving the other treatments were misted with about 0.3 cm water before being transferred to the greenhouse. Response ratings assessed after four weeks are recorded in Table G based on the same rating system as described in Test A.

TABLE G

| | NUTSEDGE TEST | | | |
|---|---|---|---|---|
| | Compound 3 Response Rating (After 4 Weeks) | | | |
| Rate kg/ha | Pre-Emergence Soil Surface | Tuber Spray | Soil Incorp. | Post-Emergence |
| 0.007 | 7G | 7G | 7G | 0 |
| 0.03 | 8G | 8G | 8G | 2C,5G |
| 0.12 | 8G | 8G | 9G | 4C,6G |

What is claimed is:

1. A compound of the formula:

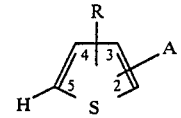

wherein
A is $SO_2N(R_3)C(O)N(R_4)R_5$;
R is $C_1$–$C_4$ alkyl, $C_3$ alkenyl, $OCH_3$, $NO_2$, Cl, Br, $SO_2NR_1R_2$ and $SO_2N(OCH_3)CH_3$;
$R_1$ and $R_2$ are independently $C_1$–$C_3$ alkyl;
$R_3$ is H or $CH_3$;
$R_4$ is H, $CH_3$ or $OCH_3$;
$R_5$ is

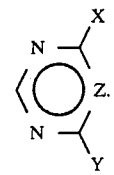

X is H, Cl, Br, $CH_3$, $CH_2CH_3$, $C_1$–$C_3$ alkoxy, $CF_3$, $SCH_3$, $CH_2OCH_3$, $OCH_2CH=CH_2$ or $OCH_2C\equiv CH$;
Y is $CH_3$ or $OCH_3$;
Z is N;
and their agricultural salts; provided that
(a) A cannot be in the 4-position of the thiophene ring; and
(b) one of $R_3$ or $R_4$ must be H; and
(c) when A is in the 3-position and R is in the 2-position, then R is other than Cl, Br or $CH_3$.

2. A compound of claim 1 wherein $R_3$ is H, and $R_4$ is H or $CH_3$.

3. A compound of claim 2 wherein Q is O.

4. A compound of claim 3 with the formula

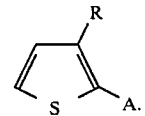

5. A compound of claim 3 with the formula

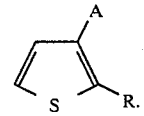

6. A compound of claim 3 with the formula

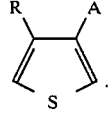

7. A compound of claim 4 wherein X is H, Cl, $CH_3$, $CH_2CH_3$, $OCH_3$ or $OCH_2CH_3$.

8. A compound of claim 5 wherein X is H, Cl, $CH_3$, $CH_2CH_3$, $OCH_3$ or $OCH_2CH_3$.

9. A compound of claim 6 wherein X is H, Cl, $CH_3$, $CH_2CH_3$, $OCH_3$ or $OCH_2CH_3$.

10. A compound of claim 7 wherein R is $CH_3$, $NO_2$, Cl, Br or $SO_2N(CH_3)_2$.

11. A compound of claim 8 wherein R is $CH_3$, $NO_2$, Cl, Br or $SO_2N(CH_3)_2$.

12. A compound of claim 9 wherein R is $CH_3$, Cl, Br or $SO_2N(CH_3)_2$.

13. The compound of claim 1 N-[(4-methoxy-6-methyl-1,3,5-triazin-2-yl)aminocarbonyl]-3-chloro-2-thiophenesulfonamide.

14. The compound of claim 1 N-[(4,6-dimethyl-1,3,5-triazin-2-yl)aminocarbonyl]-3-chloro-2-thiophenesulfonamide.

15. The compound of claim 1 N-[(4,6-dimethoxy-1,3,5-triazin-2-yl)aminocarbonyl]-3-chloro-2-thiophenesulfonamide.

16. The compound of claim 1 N-[(4-methoxy-6-methyl-1,3,5-triazin-2-yl)aminocarbonyl]-3-bromo-2-thiophenesulfonamide.

17. The compound of claim 1 N-[(4,6-dimethyl-1,3,5-triazin-2-yl)aminocarbonyl]-3-bromo-2-thiophenesulfonamide.

18. The compound of claim 1 N-[(4,6-dimethoxy-1,3,5-triazin-2-yl)aminocarbonyl]-3-bromo-2-thiophenesulfonamide.

19. A composition suitable for controlling the growth of undesired vegetation which comprises an effective amount of a compound of claim 1 and at least one of the following: surfactant, solid or liquid diluent.

20. A composition suitable for controlling the growth of undesired vegetation which comprises an effective amount of a compound of claim 2 and at least one of the following: surfactant, solid or liquid diluent.

21. A composition suitable for controlling the growth of undesired vegetation which comprises an effective amount of a compound of claim 3 and at least one of the following: surfactant, solid or liquid diluent.

22. A composition suitable for controlling the growth of undesired vegetation which comprises an effective amount of a compound of claim 4 and at least one of the following: surfactant, solid or liquid diluent.

23. A method for controlling the growth of undesired vegetation which comprises applying to the locus to be protected an effective amount of a compound of claim 1.

24. A method for controlling the growth of undesired vegetation which comprises applying to the locus to be protected an effective amount of a compound of claim 2.

25. A method for controlling the growth of undesired vegetation which comprises applying to the locus to be protected an effective amount of a compound of claim 3.

26. A method for controlling the growth of undesired vegetation which comprises applying to the locus to be protected an effective amount of a compound of claim 4.

* * * * *